(12) United States Patent
Van Berkel et al.

(10) Patent No.: US 7,927,834 B2
(45) Date of Patent: Apr. 19, 2011

(54) RECOMBINANT PRODUCTION OF MIXTURES OF ANTIBODIES

(75) Inventors: Patrick H. C. Van Berkel, Utrecht (NL); Ronald Hendrik Peter Brus, Voorschoten (NL); Ton Logtenberg, Driebergen (NL); Abraham Bout, Moerkapelle (NL)

(73) Assignee: Merus B.V., Utrecht (NL)

( * ) Notice: Subject to any disclaimer, the term of this patent is extended or adjusted under 35 U.S.C. 154(b) by 193 days.

(21) Appl. No.: 12/221,021

(22) Filed: Jul. 29, 2008

(65) Prior Publication Data

US 2009/0263864 A1    Oct. 22, 2009

Related U.S. Application Data

(60) Division of application No. 11/593,279, filed on Nov. 6, 2006, now Pat. No. 7,429,486, which is a division of application No. 11/039,767, filed on Jan. 18, 2005, now Pat. No. 7,262,028, which is a continuation of application No. PCT/EP03/07690, filed on Jul. 15, 2003.

(60) Provisional application No. 60/397,066, filed on Jul. 18, 2002.

(30) Foreign Application Priority Data

Jul. 18, 2002 (EP) .................................. 02077953

(51) Int. Cl.
| | |
|---|---|
| C12N 15/00 | (2006.01) |
| C12N 5/06 | (2006.01) |
| C12N 5/16 | (2006.01) |
| C12P 21/06 | (2006.01) |
| C12P 21/02 | (2006.01) |

(52) U.S. Cl. .................... 435/69.6; 435/69.1; 435/69.5; 435/325; 435/328

(58) Field of Classification Search ........................ None
See application file for complete search history.

(56) References Cited

U.S. PATENT DOCUMENTS

| | | |
|---|---|---|
| 4,399,216 A | 8/1983 | Axel et al. |
| 4,599,311 A | 7/1986 | Kawasaki |
| 4,634,665 A | 1/1987 | Axel et al. |
| 4,801,687 A | 1/1989 | Ngo |
| 4,816,567 A | 3/1989 | Cabilly et al. |
| 4,868,103 A | 9/1989 | Stavrianopoulos et al. |
| 4,937,190 A | 6/1990 | Palmenberg et al. |
| 5,137,809 A | 8/1992 | Loken et al. |
| 5,151,504 A | 9/1992 | Croze |
| 5,179,017 A | 1/1993 | Axel et al. |
| 5,223,409 A | 6/1993 | Ladner et al. |
| 5,627,037 A | 5/1997 | Ward et al. |
| 5,631,169 A | 5/1997 | Lakowicz et al. |
| 5,641,640 A | 6/1997 | Hanning |
| 5,667,988 A | 9/1997 | Barbas et al. |
| 5,733,779 A | 3/1998 | Reff |
| 5,772,997 A | 6/1998 | Hudziak et al. |
| 5,783,186 A | 7/1998 | Arakawa et al. |
| 5,789,208 A | 8/1998 | Sharon |
| 5,888,789 A | 3/1999 | Rodriguez |
| 5,965,371 A | 10/1999 | Marasco et al. |
| 6,004,940 A | 12/1999 | Marasco et al. |
| 6,080,560 A | 6/2000 | Russell et al. |
| 6,180,357 B1 | 1/2001 | Young et al. |
| 6,207,446 B1 | 3/2001 | Szostak et al. |
| 6,265,150 B1 | 7/2001 | Terstappen et al. |
| 6,291,740 B1 | 9/2001 | Bremel et al. |
| 6,303,341 B1 | 10/2001 | Hiatt et al. |
| 6,335,163 B1 | 1/2002 | Sharon |
| 7,067,284 B1 * | 6/2006 | Barbas et al. ................. 435/69.6 |
| 7,262,028 B2 | 8/2007 | Van Berkel et al. |
| 7,429,486 B2 | 9/2008 | Van Berkel et al. |
| 2003/0039958 A1 | 2/2003 | Holt et al. |
| 2003/0091561 A1 | 5/2003 | van de Winkel et al. |
| 2003/0194403 A1 | 10/2003 | van de Winkel et al. |
| 2003/0207346 A1 | 11/2003 | Arathoon et al. |
| 2003/0224408 A1 | 12/2003 | Hoogenboom et al. |
| 2007/0054362 A1 | 3/2007 | Van Berkel et al. |
| 2007/0059766 A1 | 3/2007 | Logtenberg |
| 2009/0263864 A1 | 10/2009 | Van Berkel et al. |

FOREIGN PATENT DOCUMENTS

| | | |
|---|---|---|
| CA | 2 405 961 | 11/2001 |
| CA | 1 341 364 | 6/2002 |
| CA | 2 445 255 | 10/2002 |
| CA | 2 114 353 | 1/2006 |
| EP | 0 120 694 | 10/1984 |
| EP | 0 314 161 | 5/1989 |
| EP | 0 402 029 | 12/1990 |
| EP | 0 445 625 | 9/1991 |
| EP | 0 481 790 | 4/1992 |
| EP | 0 523 949 | 1/1993 |

(Continued)

OTHER PUBLICATIONS

French, et al., Cancer Research, 1991, pp. 2353-2361, vol. 51.
Boel et al., Functional human monoclonal antibodies of all isotypes constructed from phage display library-derived single-chain Fv antibody fragments, Journal of Immunological Methods, 2000, pp. 153-166, vol. 239.
de Kruif et al., Selection and Application of Human Single Chain Fv Antibody Fragments from a Semi-synthetic Phage Antibody Display Library with Designed CDR3 Regions, Journal of Molecular Biology, 1995, pp. 97-105, vol. 248.
Figini et al., In Vitro Assembly of Repertoires of Antibody Chains on the Surface of Phage by Renaturation, Journal of Molecular Biology, 1994, pp. 68-78, vol. 239.

(Continued)

*Primary Examiner* — Anne M. Gussow
(74) *Attorney, Agent, or Firm* — TraskBritt, P.C.

(57) ABSTRACT

The invention provides methods for producing mixtures of antibodies from a single host cell clone, wherein, a nucleic acid sequence encoding a light chain and nucleic acid sequences encoding different heavy chains are expressed in a recombinant host cell. The recombinantly produced antibodies in the mixtures according to the invention suitably comprise identical light chains paired to different heavy chains capable of pairing to the light chain, thereby forming functional antigen-binding domains. Mixtures of the recombinantly produced antibodies are also provided by the invention. Such mixtures can be used in a variety of fields.

23 Claims, 31 Drawing Sheets

FOREIGN PATENT DOCUMENTS

| | | |
|---|---|---|
| EP | 0 724 639 | 1/2001 |
| EP | 1 325 932 B1 | 4/2005 |
| FR | 2817875 | 6/2002 |
| WO | WO 91/08216 | 6/1991 |
| WO | WO 91/17271 | 11/1991 |
| WO | WO 92/01047 | 1/1992 |
| WO | WO 92/09690 | 6/1992 |
| WO | WO 92/15679 | 9/1992 |
| WO | WO 92/18619 | 10/1992 |
| WO | WO 92/20791 | 11/1992 |
| WO | WO 93/01288 | 1/1993 |
| WO | WO 94/02610 | 2/1994 |
| WO | WO 94/25591 | 11/1994 |
| WO | WO 95/17085 | 6/1995 |
| WO | WO 95/17500 | 6/1995 |
| WO | WO 95/20401 | 8/1995 |
| WO | WO 96/27011 | 9/1996 |
| WO | WO 97/42313 | 11/1997 |
| WO | WO 97/47739 | 12/1997 |
| WO | WO 98/15627 | 4/1998 |
| WO | WO 98/15833 | 4/1998 |
| WO | WO 98/39416 | 9/1998 |
| WO | WO 98/41645 | 9/1998 |
| WO | WO 98/50431 | 11/1998 |
| WO | WO 99/20749 | 4/1999 |
| WO | WO 99/23221 | 5/1999 |
| WO | WO 99/26569 | 7/1999 |
| WO | WO 99/36569 | 7/1999 |
| WO | WO 99/64582 | 12/1999 |
| WO | WO 00/63403 | 10/2000 |
| WO | WO 00/70023 | 11/2000 |
| WO | WO 00/71694 A1 | 11/2000 |
| WO | WO 01/19394 | 3/2001 |
| WO | WO 01/27279 | 4/2001 |
| WO | WO 01/32901 | 5/2001 |
| WO | WO 01/48485 | 7/2001 |
| WO | WO 01/64929 | 9/2001 |
| WO | WO 01/88132 A2 | 11/2001 |
| WO | WO 02/18948 | 3/2002 |
| WO | WO 02/46233 A1 | 6/2002 |
| WO | WO 02/074969 A2 | 9/2002 |
| WO | WO 02/096948 A2 | 12/2002 |
| WO | WO 03/004704 | 1/2003 |
| WO | WO 03/016501 A2 | 2/2003 |
| WO | WO 03/048306 A2 | 6/2003 |
| WO | WO 03/102157 A2 | 12/2003 |
| WO | WO 2004/106375 A1 | 12/2004 |
| WO | WO 2005/068622 A2 | 7/2005 |

OTHER PUBLICATIONS

Franconi et al., Functional expression in bacteria and plants of an scFv antibody fragment against tospoviruses, Immunotechnology, 1999, pp. 189-201, vol. 4.
Lindhofer et al., Preferential Species-Restricted Heavy/Light Chain Pairing in Rat/Mouse Quadromas, 1995, pp. 219-225, vol. 155.
Merchant et al., An efficient route to human bispecific IgG, Nature Biotechnology, Jul. 1998, pp. 677-681, vol. 16.
Morrison, Sherie L., Transfectomas Provide Novel Chimeric Antibodies, Science, Sep. 20, 1985, pp. 1202-1207, vol. 229.
Pau et al, The human cell line PER.C6 provides a new manufacturing system for the production of influenza vaccines, Vaccine, 2001, pp. 2716-2712, vol. 19.
PCT International Preliminary Examination Report, PCT/EP03/07690, dated Nov. 11, 2004.
PCT International Search Report, PCT/EP03/07690, dated Apr. 16, 2004.
Vaughan et al., Human Antibodies with Sub-nanomolar Affinities Isolated from a Large Non-immunized Phage Display Library, Nature Biotechnology, Mar. 1996, pp. 309-314, vol. 14.
Ma et al., Assembly of monoclonal antibodies with IgG1 and IgA heavy chain domains in transgenic tabacco plants, Eur. J. Immunol., 1994, p. 131-38, vol. 24.
Sugita, et al., Int. J. Cancer, 1986, pp. 351-357, vol. 37.
Warnaar et al., Hybridoma, 1994, pp. 519-526, vol. 13, No. 6.
Burioni et al., Nonneutralizing Human Antibody Fragments against Hepatitis C Virus E2 Glycoprotein Modulate Neutralization of Binding Activity of Human Recombinant Fabs, Abstract, Virology, Sep. 2001, pp. 29-35, vol. 288, No. 1.
Champion et al., Abstract, The development of monoclonal human rabies virus-neutralizing antibodies as a substitute for pooled human immune globulin in the prophylactic treatment of rabies virus exposure, Abstract. Journal of Immunological Methods, Feb. 2000, pp. 81-90, vol. 235, No. 1-2, Elsevier Science Publishers B. V., Amsterdam, NL.
Chen et al., Abstract, Selection and analysis of an optimized anti-VEGF antibody: crystal structure of an affinity-matured Fab in complex with antigen, Journal of Molecular Biology, Nov. 5, 1999, pp. 865-881, vol. 293, No. 4.
De Kruif et al., Rapid selection of cell subpopulation-specific human monoclonal antibodies from a synthetic phage antibody library, Proc. Natl. Acad. Sci., USA, Apr. 1995, pp. 3938-3942, vol. 92.
Friedenson et al., Immunoglobulin G Antibodies from an Individual Rabbit in Which Several Heavy Chain Variants Are Paired with One Light Chain Sequence, The Journal of Biological Chemistry, 1973, pp. 7073-7079, vol. 248, No. 20.
Holliger et al., "Diabodies": Small bivalent and bispecific antibody fragments, Proc. Natl. Acad. Sci., Jul. 1993, pp. 6444-6448, vol. 90.
Hoogenboom et al., Antibody phage display technology and its applications, Immunotechnology, 1998, pp. 1-20, vol. 4.
Huse et al., Purification of antibodies by affinity chromatography, Journal of Biochemical and Biophysical Methods, 2002, pp. 217-231, vol. 51.
Kang et al., Linkage of recognition and replication functions by assembling combinatorial antibody Fab libraries along phage surfaces, Proc. Natl. Acad. Sci., May 1991, pp. 4363-4366, vol. 88.
Kortt et al., Dimeric and trimeric antibodies: high avidity scFvs for cancer targeting, Biomol. Eng., Oct. 15, 2001, pp. 95-108, vol. 18, No. 3.
Krebs et al., High-throughput generation and engineering of recombinant human antibodies, Journal of Immunological Methods, 2001, pp. 67-84, vol. 254.
Kwaks et al., Identification of anti-repressor elements that confer high and stable protein production in mammalian cells, Nature Biotechnology, 2003, pp. 553-558, vol. 21.
Lekkerkerker, Phage antibodies against human dendritic cell subpopulations obtained by flow cytometry-based selection on freshly isolated cells, Journal of Immunological Methods, 1999, pp. 53-63, vol. 231.
Lu et al., Selection of high affinity human neutralizing antibodies to VEGFR2 from a large antibody phage display library for antiangiogenesis therapy, Abstract, International Journal of Cancer, Jan. 20, 2002, pp. 393-399, vol. 97, No. 3.
Norderhaug et al., Balanced expression of single subunits in a multisubunit proteins, achieved by cell fusion of individual transfectants, European Journal of Biochemistry, 2002, pp. 3205-3210, vol. 269.
PCT International Search Report, PCT/NL2004/000386 dated Nov. 23, 2004.
PCT International Search Report, PCT/NL2005/000036, dated Jan. 19, 2005.
Sidhu et al., Phage-displayed antibody libraries of synthetic heavy chain complementarity determining regions, Abstract, Journal of Molecular Biology, Apr. 23, 2004, pp. 299-310, vol. 338, No. 2.
Vaughan et al., Human Antibodies with Sub-nanomolar Affinities Isolated from a Large Non-immunized Phage Display Library, Nature Biotechnology, Mar. 1996, pp. 309-314, vol. 14.
Ward et al., Nature, 1989, pp. 544-546, vol. 341.
Office Action for U.S. Appl. No. 11/490,545 dated Mar. 25, 2008.
Office Action for U.S. Appl. No. 11/490,545 dated Jul. 30, 2008.
Office Action for U.S. Appl. No. 11/490,545 dated May 29, 2009.
Office Action for U.S. Appl. No. 11/490,545 dated Jan. 13, 2010.

* cited by examiner

```
UBS54-VL    GAAATTGAGCTCACTCAGTCTCCACTCTCCCTGCCCGTCACCCCTGGAGAGCCGGCC
K53-VL      GAAATTGAGCTCACTCAGTCTCCACTCTCCCTGCCCGTCACCCCTGGAGAGCCGGCC
02-237-VL   GACATCGTGATGACTCAGTCTCCACTCTCCACTGCCCGTCACCCCTGGAGAGCCGGCC
            ** ** * *************** *********************************

UBS54-VL    TCCATCTCCTGCAGGTCTAGTCAGAGCCTCCTGCATAGTAATGGATACAACTATTTGGAT
K53-VL      TCCATCTCCTGCAGGTCTAGTCAGAGCCTCCTGCATAGTAATGGATACAACTATTTGGAT
02-237-VL   TCCATCTCCTGCAGGTCTAGTCAGAGCCTCCTGCATAGTAATGGATACAACTATTTGGAT
            ************************************************************

UBS54-VL    TGGTACCTGCAGAAGCCAGGGCAGTCTCCACAGCTCCTGATCTATTTGGGTTCTAATCGG
K53-VL      TGGTACCTGCAGAAGCCAGGGCAGTCTCCACAGCTCCTGATCTATTTGGGTTCTAATCGG
02-237-VL   TGGTACCTGCAGAAGCCAGGGCAGTCTCCACAGCTCCTGATCTATTTGGGTTCTAATCGG
            ************************************************************

UBS54-VL    GCCTCCGGGGTCCCTGACAGATTCAGTGGCAGTGGATCAGGCACAGATTTACACTGAAA
K53-VL      GCCTCCGGGGTCCCTGACAGATTCAGTGGCAGTGGATCAGGCACAGATTTACACTGAAA
02-237-VL   GCCTCCGGGGTCCCTGACAGATTCAGTGGCAGTGGATCAGGCACAGATTTACACTGAAA
            ***********************************************************

UBS54-VL    ATCAGCAGAGTGGAGGCTGAGGATGTTGGGGTTTATTACTGCATGCAAGCTCTACAAACT
K53-VL      ATCAGCAGAGTGGAGGCTGAGGATGTTGGGGTTTATTACTGCATGCAAGCTCTACAAACT
02-237-VL   ATCAGCAGAGTGGAGGCTGAGGATGTTGGGGTTTATTACTGCATGCAAGCTCTACAAACT
            ************************************************************

UBS54-VL    TTCACTTTCGGCCCTGGGACCAAGGTGGAGATCAAA
K53-VL      TTCACTTTCGGCCCTGGGACCAAGGTGGAGATCAAA
02-237-VL   TTCACTTTCGGCCCTGGGACCAAGGTGGAGATCAAA
            ************************************
```

FIG. 3A

```
K53-VH      CAGGTGCAGCTGGTGCAGTCTGGGGCTGAGGTGAAGAAGCCTGGGGCCTCAGTGAAGGTC
02-237-VH   CAGGTGCAGCTGGTGCAGTCTGGGGCTGAGGTGAAGAAGCCTGGGGCCTCAGTGAAGGTC
UBS54-VH    CAGGTGCAGCTGGTGCAGTCTGGGGCTGAGGTGAAGAAGCCTGGGTCCTCGGTGAGGGTC
            ******************************************** **** *** *****

K53-VH      TCCTGCAAGGCTTCTGGTTACACCTTTACCAGCTATGGTATCAGCTGGGTGCGACAGGCC
02-237-VH   TCCTGCAAGGCTTCTGGTTACACCTTTACCAGCTATGGTATCAGCTGGGTGCGACAGGCC
UBS54-VH    TCCTGCAAGGGCTTCTGGAGGCACCTTCAGCAGCTATGCTATCAGCTGGGTGCGACAGGCC
            ********** ******* * ****** *  ******* *********************

K53-VH      CCTGGACAAGGGCTTGAGTGGATGGATGGATCAGCGCTTACAATGTAACACAAACTAT
02-237-VH   CCTGGACAAGGGCTTGAGTGGATGGATGGATCAGCGCTTACAATGTAACACAAACTAT
UBS54-VH    CCTGGACAAGGGCTTGAGTGGATGGGAGGATCATCCCTATCTTTGGTACAGCAAACTAC
            *************************  ****** *   ** * *  * *** *******

K53-VH      GCACAGAAGTTCCAGGGCAGAGTCACCATGACCACAGACACATCCACGAGCACAGCCTAC
02-237-VH   GCACAGAAGTTCCAGGGCAGAGTCACCATGACCACAGACACATCCACGAGCACAGCCTAC
UBS54-VH    GCACAGAAGTTCCAGGGCAGAGTCACCATGACCGGAATCCACGAGCACAGCCTAC
            ********************************* *  **  ** **************

K53-VH      ATGGAGCTGAGGAGCCTGAGATCTGACGACACGGCCGTGTATTACTGTGCAAGGGGCATG
02-237-VH   ATGGAGCTGAGGAGCCTGAGATCTGACGACACGGCCGTGTATTACTGTGCAAGGGGCTTT
UBS54-VH    ATGGAGCTGAGCAGCCTGAGGACTGAGGACACGGCTGTGTATTACTGTGCAAGAGACC--
            *********** ******** * ** ******** **************** *  *

K53-VH      ATGAGGGGTGTGTTTGACTACTGGGGCCAAGTACCCCTGGTCACCGTCTCGACA
02-237-VH   CCGCGTACGTCGTTTGACTCCTGGGGGCCAGGCACCCTGGTGACCGTCTCCTCA
UBS54-VH    ------CGTTTCTTCACTATTGGGGCCAAGTACCCTGGTCACCGTCTCGACA
                  ** ******  **  ********   *** ** **********
```

FIG. 3B

Anti-CD22 V_H fragment (Phage B28)

```
            M  A  E  V  Q  L  V  E  S  G  G  G  V  V  R  P  G  G  S  L  R  L  S  C
  1   ATGGCCGAGGTGCAGCTGGTGGAGTCTGGGGGAGGTGTGGTACGGCCTGGAGGGTCCCTGAGACTCTCCTG
         A  A  S  G  F  T  F  D  D  Y  G  M  S  W  V  R  Q  A  P  G  K  G  L  E
 72   TGCAGCCTCTGGATTCACCTTTGATGATTATGGCATGAGCTGGGTCCGCCAAGCTCCAGGGAAGGGGCTGG
         W  V  S  G  I  N  W  N  G  G  S  T  G  Y  A  D  S  V  K  G  R  F  T
143   AGTGGGTCTCTGGTATTAATTGGAATGGTGGTAGCACAGGTTATGCAGACTCTGTGAAGGGCCGATTCACC
         I  S  R  D  N  A  K  N  S  L  Y  L  Q  M  N  S  L  R  A  E  D  T  A  V
214   ATCTCCAGAGACAACGCCAAGAACTCCCTGTATCTGCAAATGAACAGTCTGAGAGCCGAGGACACGGCCGT
         Y  Y  C  A  R  G  F  L  R  F  A  S  S  W  F  D  Y  W  G  Q  G  T  L  V
285   GTATTACTGTGCAAGAGGCTTTCTTCGTTTTGCTTCCTCCTGGTTTGACTACTATTGGGGCCAAGGTACCCTGG
         T  V  S  R
356   TCACCGTCTCGAGA
```

Anti-CD72 V_H fragment (Phage II-2)

```
            M  A  Q  V  Q  L  V  Q  S  G  A  E  V  K  K  P  G  A  S  V  K  V  S  C
  1   ATGGCCCAGGTGCAGCTGGTGCAGTCTGGGGCTGAGGTGAAGAAGCCTGGGGCCTCAGTGAAGGTTTCCTG
         K  A  S  G  Y  T  F  T  S  Y  Y  M  H  W  V  R  Q  A  P  G  Q  G  L  E
 72   CAAGGCATCTGGATACACCTTCACCAGCTACTATATGCACTGGGTGCGACAGGCCCCTGGACAAGGGCTTG
         W  M  G  I  I  N  P  S  G  G  S  T  S  Y  A  Q  K  F  Q  G  R  V  T
143   AGTGGATGGGAATAATCAACCCTAGTGGTGGCACAAGCTACGCACAGAAGTTCCAGGGCAGAGTCACC
         M  T  R  D  T  S  T  S  T  V  Y  M  E  L  S  S  L  R  S  E  D  T  A  V
214   ATGACCAGGGACACGTCCACGAGCACAGTCTACATGGAGCTGAGCAGCCTGAGATCTGAGGACACGGCCGT
         Y  Y  C  A  R  D  Y  Y  V  T  Y  D  S  W  F  D  S  W  G  Q  G  T  L  V
285   GTATTACTGTGCAAGAGATTACTACGTTACGTATGATTCCTGGTTTGACTCCTGGGGCCAAGGTACCCTGG
         T  V  S  R
356   TCACCGTCTCGAGA
```

FIG. 7A

Anti-Class II V_H fragment (Phage I-2)

```
      M  A  E  V  Q  L  V  E  S  G  G  G  L  V  Q  P  G  R  S  L  R  L  S  C
  1  ATGGCCGAGGTGCAGCTGGTGGAGTCTGGGGGAGGCTTGGTACAGCCTGGCAGGTCCCTGAGACTCTCCTG
      .  A  A  S  G  F  T  F  D  D  Y  A  M  H  W  V  R  Q  A  P  G  K  G  L  E
 72  TGCAGCCTCTGGATTCACCTTTGATGATTATGCCATGCACTGGGTCCGGCAAGCTCCAGGGAAGGGCCTGG
      .  W  V  S  G  I  S  W  N  S  G  S  I  G  Y  A  D  S  V  K  G  R  F  T
143  AGTGGGTCTCAGGTATTAGTTGGAATAGTGGTAGCATAGGCTATGCGGACTCTGTGAAGGGCCGATTCACC
      I  S  R  D  N  A  K  N  S  L  Y  L  Q  M  N  S  L  R  A  E  D  T  A  V
214  ATCTCCAGAGACAACGCCAAGAACTCCCTGTATCTGCAAATGAACAGTCTGAGAGCTGAGGACACGGCCGT
      .  Y  Y  C  A  R  D  L  Y  L  A  H  F  D  Y  W  G  Q  G  T  L  V  T  V  S
285  GTATTACTGTGCAAGGGACCTTTATCTTGCGCATTTTGACTACTGGGGCCAAGGTACCCTGGTCACCGTCT
      .  R
356  CGAGA
```

Shared V_L sequence of Phages I-2, II-2 and B28

```
      S  S  E  L  T  Q  D  P  A  V  S  V  A  L  G  Q  T  V  R  I  T  C  Q  G
  1  TCGTCTGAGCTGACTCAGGACCCTGCTGTGTCTGTGGCCTTGGGACAGACAGTCAGGATCACATGCCAAGG
      .  D  S  L  R  S  Y  Y  A  S  W  Y  Q  Q  K  P  G  Q  A  P  V  L  V  I  Y
 72  AGACAGCCTGAGAAGCTATTATGCAAGCTGGTACCAGCAGAAGCCAGGACAGGCCCCTGTACTTGTCATCT
      .  G  K  N  N  R  P  S  G  I  P  D  R  F  S  G  S  S  S  G  N  T  A  S
143  ATGGTAAAAACAACCGGCCCTCAGGGATCCCCAGACCGATTCTCTGGCTCCAGCTCAGGAAACACAGCTTCC
      L  T  I  T  G  A  Q  A  E  D  E  A  D  Y  Y  C  N  S  R  D  S  S  G  N
214  TTGACCATCACTGGGGCTCAGGCTGAAGATGAGGCTGACTATTACTGTAACTCCCGGACAGCAGTGGTAA
      .  H  V  F  G  G  G  T  K  L  T  V  L  G  A  A  A
285  CCATGTGGTATTCGGCGGAGGGACCAAGCTGACCGTCCTAGGTGCGGCCGCA
```

FIG. 7B

V_H sequence of K53 IgG

```
       Q   V   Q   L   V   Q   S   G   A   E   V   K   K   P   G   A   S   V   K   V
  1    CAGGTGCAGCTGGTGCAGTCTGGGGCTGAGGTGAAGAAGCCTGGGGCCTCAGTGAAGGTC

S   C   K   A   S   G   Y   T   F   T   S   Y   G   I   S   W   V   R   Q   A
 61    TCCTGCAAGGCTTCTGGTTACACCTTTACCAGCTATGGTATCAGCTGGGTGCGACAGGCC

P   G   Q   G   L   E   W   M   G   W   I   S   A   Y   N   G   N   T   N   Y
121    CCTGGACAAGGGCTTGAGTGGATGGGATGGATCAGCGCTTACAATGGTAACACAAACTAT

A   Q   K   L   Q   G   R   V   T   M   T   T   D   T   S   T   S   T   A   Y
181    GCACAGAAGCTCCAGGGCAGAGTCACCATGACCACAGACACATCCACGAGCACAGCCTAC

M   E   L   R   S   L   R   S   D   D   T   A   V   Y   Y   C   A   R   G   M
241    ATGGAGCTGAGGAGCCTGAGATCTGACGACACGGCCGTGTATTACTGTGCAAGGGGCATG

M   R   G   V   F   D   Y   W   G   Q   G   T   L   V   T   V   S   T
301    ATGAGGGGTGTGTTTGACTACTGGGGCCAAGGTACCCTGGTCACCGTCTCGACA
```

FIG. 12A

V_H sequence of 02-237 IgG

```
1    Q  V  Q  L  V  Q  S  G  A  E  V  K  K  P  G  A  S  V  K  V
     CAGGTGCAGCTGGTGCAGTCTGGGGCTGAGGTGAAGAAGCCTGGGGCCTCAGTGAAGGTC

61   S  C  K  A  S  G  Y  T  F  T  S  Y  G  I  S  W  V  R  Q  A
     TCCTGCAAGGCTTCTGGTTACACCTTTACCAGCTATGGTATCAGCTGGGTGCGACAGGCC

121  P  G  Q  G  L  E  W  M  G  W  I  S  A  Y  N  G  N  T  N  Y
     CCTGGACAAGGGCTTGAGTGGATGGGATGGATCAGCGGCTTACAATGGTAACACAAACTAT

181  A  Q  K  L  Q  G  R  V  T  M  T  T  D  T  S  T  S  T  A  Y
     GCACAGAAGCTCCAGGGCAGAGTCACCATGACCACAGACACATCCACGAGCACAGCCTAC

241  M  E  L  R  S  L  R  S  D  D  T  A  V  Y  Y  C  A  R  G  F
     ATGGAGCTGAGGAGCCTGAGATCTGACGACACGGCCGTGTATTACTGTGCAAGGGGCTTT

301  P  R  T  S  F  D  S  W  G  Q  G  T  L  V  T  V  S  S
     CCGCGTACGTCGTTTGACTCCTGGGGCCAGGGCACCCTGGTGACCGTCTCCTCA
```

FIG. 12B

V_H sequence of UBS54 IgG

```
    Q  V  Q  L  V  Q  S  G  A  E  V  K  K  P  G  S  S  V  R  V
1   CAGGTGCAGCTGGTGCAGTCTGGGGCTGAGGTGAAGAAGCCTGGTTCCTCGGTGAGGGTC

S  C  K  A  S  G  G  T  F  S  S  Y  A  I  S  W  V  R  Q  A
61  TCCTGCAAGGCTTCTGGAGGCACCTTCAGCAGCTATGCTATCAGCTGGGTGCGACAGGCC

P° G  Q  G  L  E  W  M  G  G  I  I  P  I  F  G  T  A  N  Y
121 CCTGGACAAGGGCTTGAGTGGATGGGAGGGATCATCCCTATCTTTGGTACAGCAAACTAC

A  Q  K  F  Q  G  R  V  T  I  T  A  D  E  S  T  S  T  A  Y
181 GCACAGAAGTTCCAGGGCAGAGTCACGATTACCGCGGACGAATCCACGAGCACAGCCTAC

M  E  L  S  S  L  R  S  E  D  T  A  V  Y  Y  C  A  R  D  P
241 ATGGAGCTGAGCAGCCTGAGATCTGAGGACACGGCTGTGTATTACTGTGCAAGAGACCCG

F  L  H  Y  W  G  Q  G  T  L  V  T  V  S  T
301 TTTCTTCACTATTGGGGCCAAGGTACCCCTGGTCACCGTCTCGACA
```

FIG. 12C

V_L sequence of K53 and UBS54 IgG

```
        E  I  E  L  T  Q  S  P  L  S  L  P  V  T  P  G  E  P  A
  1   GAAATTGAGCTCACTCAGTCTCCACTCTCCCTGCCCGTCACCCCTGGAGAGCCGGCC

S  I  S  C  R  S  S  Q  S  L  L  H  S  N  G  Y  N  Y  L  D
 58   TCCATCTCCTGCAGGTCTAGTCAGAGCCTCCTGCATAGTAATGGATACAACTATTTGGAT

W  Y  L  Q  K  P  G  Q  S  P  Q  L  L  I  Y  L  G  S  N  R
118   TGGTACCTGCAGAAGCCAGGGCCAGTCTCCACAGCTCCTGATCTATTTGGGTTCTAATCGG

A  S  G  V  P  D  R  F  S  G  S  G  S  G  T  D  F  T  L  K
178   GCCTCCGGGGTCCCTGACAGGTTCAGTGGCAGTGGATCAGGCACAGATTTTACACTGAAA

I  S  R  V  E  A  E  D  V  G  V  Y  Y  C  M  Q  A  L  Q  T
238   ATCAGCAGAGTGGAGGCTGAGGATGTTGGGGTTTATTACTGCATGCAAGCTCTACAAACT

F  T  F  G  P  G  T  K  V  E  I  K
298   TTCACTTTCGGCCCTGGGACCAAGGTGGAGATCAAA
```

V_L sequence of 02-237 IgG

```
      D   I   V   M   T   Q   S   P   L   S   L   P   V   T   P   G   E   P   A
1     GACATCGTGATGACTCAGTCTCCACTCTCCCTGCCCGTCACCCCTGGAGAGCCGGCC

S   I   S   C   R   S   S   Q   S   L   L   H   S   N   G   Y   N   Y   L   D
58    TCCATCTCCTGCAGGTCTAGTCAGAGCCTCCTGCATAGTAATGGATACAACTATTTGGAT

W   Y   L   Q   K   P   G   Q   S   P   Q   L   L   I   Y   L/G S   N   R
118   TGGTACCTGCAGAAGCCAGGCCAGTCTCCACAGCTCCTGATCTATTTGGGTTCTAATCGG

A   S   G   V   P   D   R   F   S   G   S   G   S   G   T   D   F   T   L   K
178   GCCTCCGGGGTCCCTGACAGGTTCAGTGGCAGTGGATCAGGCACAGATTTTACACTGAAA

I   S   R   V   E   A   E   D   V   G   V   Y   Y   C   M   Q   A   L   Q   T
238   ATCAGCAGAGTGGAGGCTGAGGATGTTGGGGTTTATTACTGCATGCAAGCTCTACAAACT

F   T   F   G   P   G   T   K   V   E   I   K
298   TTCACTTTCGGCCCTGGGACCAAGGTGGAGATCAAA
```

```
                       CDR1
K53 VH      1  QVQLVQSGAEVKKPGASVKVSCKASGYTFTSSYGISWVRQAPGQGLEWMG
UBS54 VH    1  QVQLVQSGAEVKKKPGSSVRVSCKASGGTFSSSYAISWVRQAPGQGLEWMG
02-237      1  QVQLVQSGAEVKKPGASVKVSCKASGYTFTSSYGISWVRQAPGQGLEWMG
               ****************-*******-*******-*-*-*-*********

CDR2
K53 VH     50  WISAYNGNTNYAQKLQGRVTMTTDTSTSTAYMELRSLRSDDTAVYYCAR
UBS54      50  GIPIFGNANYAQKFQGRVTITADESTSTAYMELSSLRSEDTAVYYCAR
02-237     50  WISAYNGNTNYAQKLQGRVTMTDTSTSTAYMELRSLRSDDTAVYYCAR
               -*----**-*-******-****-*-*-*-*******-*-***********

CDR3
K53 VH     99  GMMRGVFDYWGQGTLVTVST
UBS54      99  DPFLH---YWGQGTLVTVST
02-237     99  GFPRTSFDSWGQGTLVTVSS
               ----------*********-
```

FIG. 13

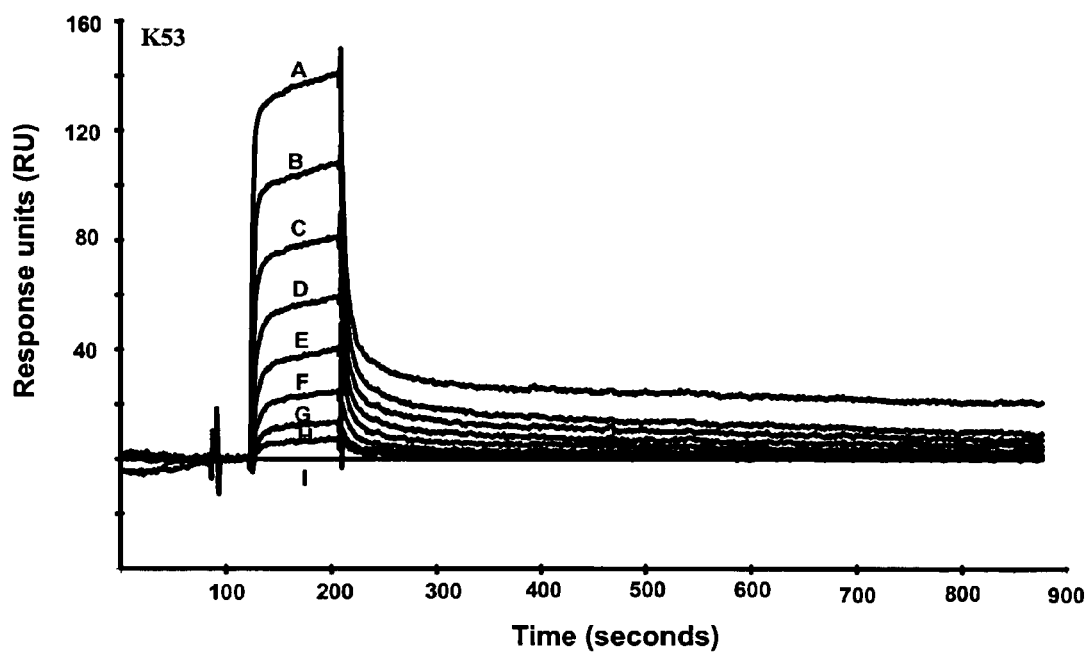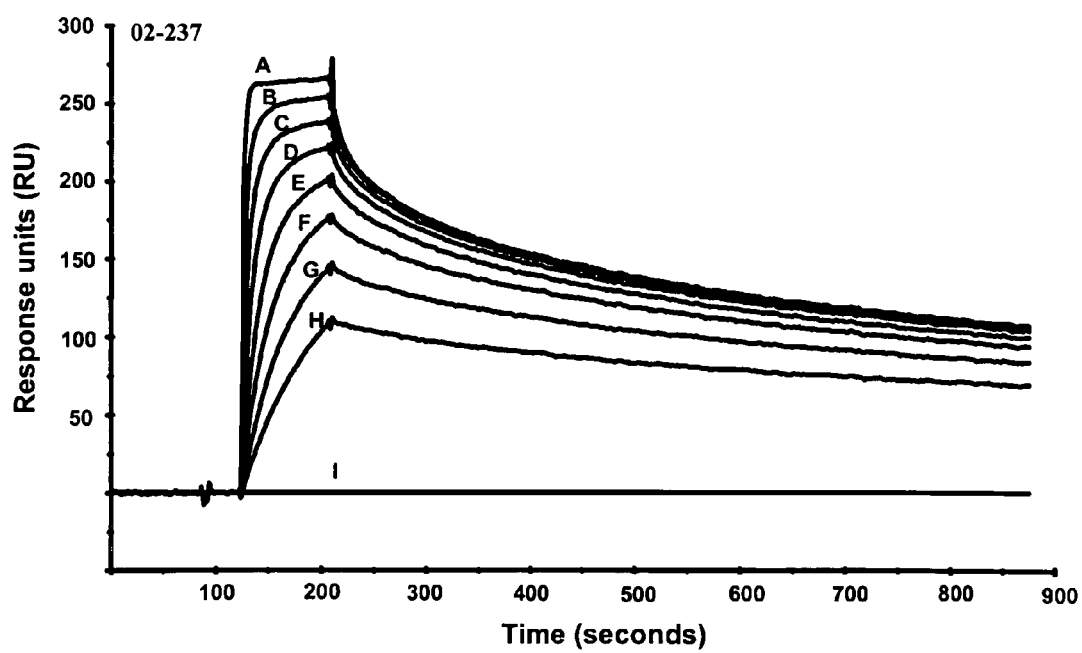
FIG. 14

A.
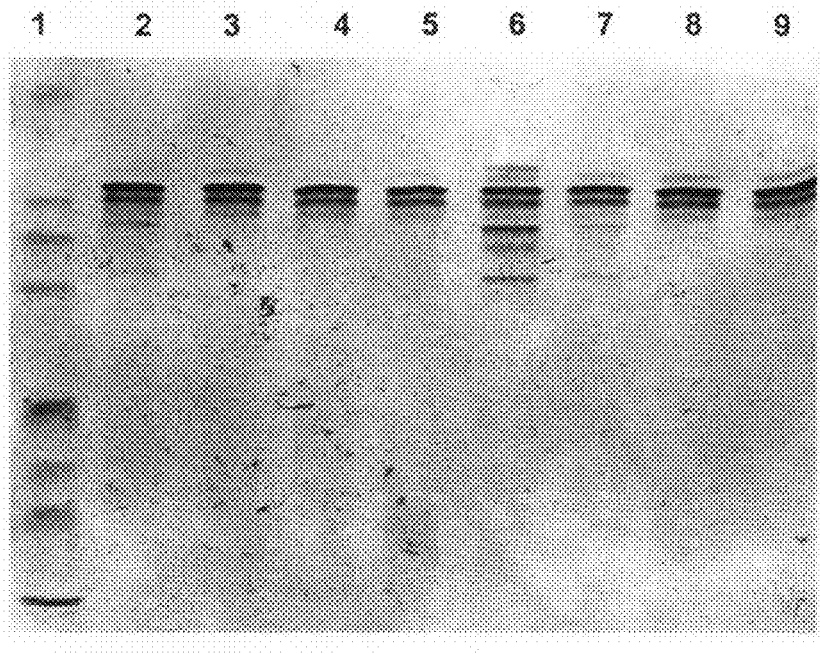
B.
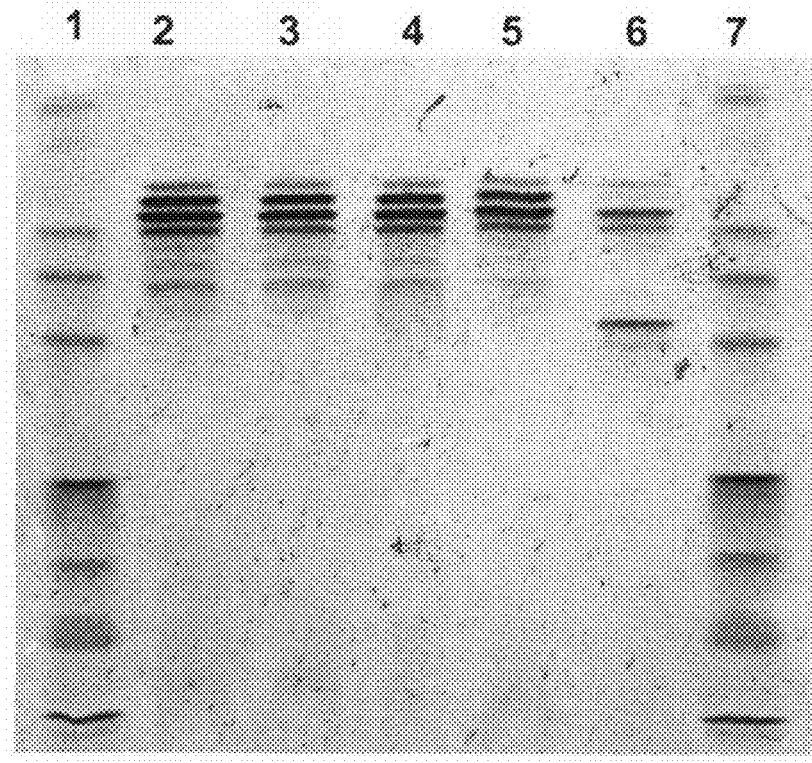
FIG. 21

SEQUENCE LISTING

```
<160> NUMBER OF SEQ ID NOS: 18

<210> SEQ ID NO 1
<211> LENGTH: 333
<212> TYPE: DNA
<213> ORGANISM: Artificial
<220> FEATURE:
<223> OTHER INFORMATION: VL sequence of UBS54 (anti-EpCAM) and K53
      (anti-CD46)
<220> FEATURE:
<221> NAME/KEY: CDS
<222> LOCATION: (1)..(333)

<400> SEQUENCE: 1 gaa att gag ctc act cag tct cca ctc tcc ctg ccc gtc acc cct gga        48
Glu Ile Glu Leu Thr Gln Ser Pro Leu Ser Leu Pro Val Thr Pro Gly
1               5                   10                  15 gag ccg gcc tcc atc tcc tgc agg tct agt cag agc ctc ctg cat agt        96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct       144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct       192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc       240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct       288
Ser Arg Val Glu Ala Glu Asp Val Gly Val Tyr Tyr Cys Met Gln Ala
                85                  90                  95 cta caa act ttc act ttc ggc cct ggg acc aag gtg gag atc aaa           333
Leu Gln Thr Phe Thr Phe Gly Pro Gly Thr Lys Val Glu Ile Lys
            100                 105                 110
```

```
<210> SEQ ID NO 2
<211> LENGTH: 111
<212> TYPE: PRT
<213> ORGANISM: Artificial
<220> FEATURE:
<223> OTHER INFORMATION: VL sequence of UBS54 (anti-EpCAM) and K53
      (anti-CD46)

<400> SEQUENCE: 2

Glu Ile Glu Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Phe Thr Phe Gly Pro Gly Thr Lys Val Glu Ile Lys
            100                 105                 110

<210> SEQ ID NO 3
<211> LENGTH: 333
<212> TYPE: DNA
<213> ORGANISM: Artificial
<220> FEATURE:
<223> OTHER INFORMATION: VL sequence of 02-237 (anti-CD46)
<220> FEATURE:
<221> NAME/KEY: CDS
<222> LOCATION: (1)..(333)

<400> SEQUENCE: 3 gac atc gtg atg act cag tct cca ctc tcc ctg ccc gtc acc cct gga      48
Asp Ile Val Met Thr Gln Ser Pro Leu Ser Leu Pro Val Thr Pro Gly
1               5                   10                  15 gag ccg gcc tcc atc tcc tgc agg tct agt cag agc ctc ctg cat agt      96
Glu Pro Ala Ser Ile Ser Cys Arg Ser Ser Gln Ser Leu Leu His Ser
            20                  25                  30 aat gga tac aac tat ttg gat tgg tac ctg cag aag cca ggg cag tct     144
Asn Gly Tyr Asn Tyr Leu Asp Trp Tyr Leu Gln Lys Pro Gly Gln Ser
        35                  40                  45 cca cag ctc ctg atc tat ttg ggt tct aat cgg gcc tcc ggg gtc cct     192
Pro Gln Leu Leu Ile Tyr Leu Gly Ser Asn Arg Ala Ser Gly Val Pro
    50                  55                  60 gac agg ttc agt ggc agt gga tca ggc aca gat ttt aca ctg aaa atc     240
Asp Arg Phe Ser Gly Ser Gly Ser Gly Thr Asp Phe Thr Leu Lys Ile
65                  70                  75                  80 agc aga gtg gag gct gag gat gtt ggg gtt tat tac tgc atg caa gct     288
Ser Arg Val Glu Ala Glu Asp Val Gly Val Tyr Tyr Cys Met Gln Ala
                85                  90                  95 cta caa act ttc act ttc ggc cct ggg acc aag gtg gag atc aaa         333
Leu Gln Thr Phe Thr Phe Gly Pro Gly Thr Lys Val Glu Ile Lys
            100                 105                 110

<210> SEQ ID NO 4
<211> LENGTH: 111
<212> TYPE: PRT
<213> ORGANISM: Artificial
<220> FEATURE:
<223> OTHER INFORMATION: VL sequence of 02-237 (anti-CD46)
```

-continued

<400> SEQUENCE: 4

| Asp | Ile | Val | Met | Thr | Gln | Ser | Pro | Leu | Ser | Leu | Pro | Val | Thr | Pro | Gly |
|---|---|---|---|---|---|---|---|---|---|---|---|---|---|---|---|
| 1 | | | | 5 | | | | | 10 | | | | | 15 | |

| Glu | Pro | Ala | Ser | Ile | Ser | Cys | Arg | Ser | Ser | Gln | Ser | Leu | Leu | His | Ser |
|---|---|---|---|---|---|---|---|---|---|---|---|---|---|---|---|
| | | | 20 | | | | | 25 | | | | | 30 | | |

| Asn | Gly | Tyr | Asn | Tyr | Leu | Asp | Trp | Tyr | Leu | Gln | Lys | Pro | Gly | Gln | Ser |
|---|---|---|---|---|---|---|---|---|---|---|---|---|---|---|---|
| | | 35 | | | | | 40 | | | | | 45 | | | |

| Pro | Gln | Leu | Leu | Ile | Tyr | Leu | Gly | Ser | Asn | Arg | Ala | Ser | Gly | Val | Pro |
|---|---|---|---|---|---|---|---|---|---|---|---|---|---|---|---|
| 50 | | | | | 55 | | | | | 60 | | | | | |

| Asp | Arg | Phe | Ser | Gly | Ser | Gly | Ser | Gly | Thr | Asp | Phe | Thr | Leu | Lys | Ile |
|---|---|---|---|---|---|---|---|---|---|---|---|---|---|---|---|
| 65 | | | | | 70 | | | | | 75 | | | | | 80 |

| Ser | Arg | Val | Glu | Ala | Glu | Asp | Val | Gly | Val | Tyr | Tyr | Cys | Met | Gln | Ala |
|---|---|---|---|---|---|---|---|---|---|---|---|---|---|---|---|
| | | | | 85 | | | | | 90 | | | | | 95 | |

| Leu | Gln | Thr | Phe | Thr | Phe | Gly | Pro | Gly | Thr | Lys | Val | Glu | Ile | Lys |
|---|---|---|---|---|---|---|---|---|---|---|---|---|---|---|
| | | | 100 | | | | | 105 | | | | | 110 | |

<210> SEQ ID NO 5
<211> LENGTH: 345
<212> TYPE: DNA
<213> ORGANISM: Artificial
<220> FEATURE:
<223> OTHER INFORMATION: VH sequence of UBS54 (anti-EpCAM)
<220> FEATURE:
<221> NAME/KEY: CDS
<222> LOCATION: (1)..(345)

<400> SEQUENCE: 5

```
cag gtg cag ctg gtg cag tct ggg gct gag gtg aag aag cct ggg tcc       48
Gln Val Gln Leu Val Gln Ser Gly Ala Glu Val Lys Lys Pro Gly Ser
 1               5                  10                  15 tcg gtg agg gtc tcc tgc aag gct tct gga ggc acc ttc agc agc tat       96
Ser Val Arg Val Ser Cys Lys Ala Ser Gly Gly Thr Phe Ser Ser Tyr
             20                  25                  30 gct atc agc tgg gtg cga cag gcc cct gga caa ggg ctt gag tgg atg      144
Ala Ile Ser Trp Val Arg Gln Ala Pro Gly Gln Gly Leu Glu Trp Met
         35                  40                  45 gga ggg atc atc cct atc ttt ggt aca gca aac tac gca cag aag ttc      192
Gly Gly Ile Ile Pro Ile Phe Gly Thr Ala Asn Tyr Ala Gln Lys Phe
     50                  55                  60 cag ggc aga gtc acg att acc gcg gac gaa tcc acg agc aca gcc tac      240
Gln Gly Arg Val Thr Ile Thr Ala Asp Glu Ser Thr Ser Thr Ala Tyr
 65                  70                  75                  80 atg gag ctg agc agc ctg aga tct gag gac acg gct gtg tat tac tgt      288
Met Glu Leu Ser Ser Leu Arg Ser Glu Asp Thr Ala Val Tyr Tyr Cys
                 85                  90                  95 gca aga gac ccg ttt ctt cac tat tgg ggc caa ggt acc ctg gtc acc      336
Ala Arg Asp Pro Phe Leu His Tyr Trp Gly Gln Gly Thr Leu Val Thr
            100                 105                 110 gtc tcg aca                                                          345
Val Ser Thr
        115
```

<210> SEQ ID NO 6
<211> LENGTH: 115
<212> TYPE: PRT
<213> ORGANISM: Artificial
<220> FEATURE:
<223> OTHER INFORMATION: VH sequence of UBS54 (anti-EpCAM)

```
<400> SEQUENCE: 6

Gln Val Gln Leu Val Gln Ser Gly Ala Glu Val Lys Lys Pro Gly Ser
 1               5                  10                  15

Ser Val Arg Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Phe Leu His Tyr Trp Gly Gln Gly Thr Leu Val Thr
            100                 105                 110

Val Ser Thr
        115

<210> SEQ ID NO 7
<211> LENGTH: 354
<212> TYPE: DNA
<213> ORGANISM: Artificial
<220> FEATURE:
<223> OTHER INFORMATION: VH sequence of K53 (anti-CD46)
<220> FEATURE:
<221> NAME/KEY: CDS
<222> LOCATION: (1)..(354)

<400> SEQUENCE: 7 cag gtg cag ctg gtg cag tct ggg gct gag gtg aag aag cct ggg gcc      48
Gln Val Gln Leu Val Gln Ser Gly Ala Glu Val Lys Lys Pro Gly Ala
 1               5                  10                  15 tca gtg aag gtc tcc tgc aag gct tct ggt tac acc ttt acc agc tat      96
Ser Val Lys Val Ser Cys Lys Ala Ser Gly Tyr Thr Phe Thr Ser Tyr
                20                  25                  30 ggt atc agc tgg gtg cga cag gcc cct gga caa ggg ctt gag tgg atg     144
Gly Ile Ser Trp Val Arg Gln Ala Pro Gly Gln Gly Leu Glu Trp Met
            35                  40                  45 gga tgg atc agc gct tac aat ggt aac aca aac tat gca cag aag ctc     192
Gly Trp Ile Ser Ala Tyr Asn Gly Asn Thr Asn Tyr Ala Gln Lys Leu
        50                  55                  60 cag ggc aga gtc acc atg acc aca gac aca tcc acg agc aca gcc tac     240
Gln Gly Arg Val Thr Met Thr Thr Asp Thr Ser Thr Ser Thr Ala Tyr
65                  70                  75                  80 atg gag ctg agg agc ctg aga tct gac gac acg gcc gtg tat tac tgt     288
Met Glu Leu Arg Ser Leu Arg Ser Asp Asp Thr Ala Val Tyr Tyr Cys
                85                  90                  95 gca agg ggc atg atg agg ggt gtg ttt gac tac tgg ggc caa ggt acc     336
Ala Arg Gly Met Met Arg Gly Val Phe Asp Tyr Trp Gly Gln Gly Thr
            100                 105                 110 ctg gtc acc gtc tcg aca                                             354
Leu Val Thr Val Ser Thr
        115

<210> SEQ ID NO 8
<211> LENGTH: 118
<212> TYPE: PRT
<213> ORGANISM: Artificial
<220> FEATURE:
<223> OTHER INFORMATION: VH sequence of K53 (anti-CD46)
```

```
<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Met Met Arg Gly Val Phe Asp Tyr Trp Gly Gln Gly Thr
                100                 105                 110

Leu Val Thr Val Ser Thr
            115

<210> SEQ ID NO 9
<211> LENGTH: 354
<212> TYPE: DNA
<213> ORGANISM: Artificial
<220> FEATURE:
<223> OTHER INFORMATION: VH sequence of 02-237 (anti-CD46)
<220> FEATURE:
<221> NAME/KEY: CDS
<222> LOCATION: (1)..(354)

<400> SEQUENCE: 9 cag gtg cag ctg gtg cag tct ggg gct gag gtg aag aag cct ggg gcc      48
Gln Val Gln Leu Val Gln Ser Gly Ala Glu Val Lys Lys Pro Gly Ala
1               5                   10                  15 tca gtg aag gtc tcc tgc aag gct tct ggt tac acc ttt acc agc tat      96
Ser Val Lys Val Ser Cys Lys Ala Ser Gly Tyr Thr Phe Thr Ser Tyr
            20                  25                  30 ggt atc agc tgg gtg cga cag gcc cct gga caa ggg ctt gag tgg atg     144
Gly Ile Ser Trp Val Arg Gln Ala Pro Gly Gln Gly Leu Glu Trp Met
        35                  40                  45 gga tgg atc agc gct tac aat ggt aac aca aac tat gca cag aag ctc     192
Gly Trp Ile Ser Ala Tyr Asn Gly Asn Thr Asn Tyr Ala Gln Lys Leu
    50                  55                  60 cag ggc aga gtc acc atg acc aca gac aca tcc acg agc aca gcc tac     240
Gln Gly Arg Val Thr Met Thr Thr Asp Thr Ser Thr Ser Thr Ala Tyr
65                  70                  75                  80 atg gag ctg agg agc ctg aga tct gac gac acg gcc gtg tat tac tgt     288
Met Glu Leu Arg Ser Leu Arg Ser Asp Asp Thr Ala Val Tyr Tyr Cys
                85                  90                  95 gca agg ggc ttt ccg cgt acg tcg ttt gac tcc tgg ggc cag ggc acc     336
Ala Arg Gly Phe Pro Arg Thr Ser Phe Asp Ser Trp Gly Gln Gly Thr
                100                 105                 110 ctg gtg acc gtc tcc tca                                              354
Leu Val Thr Val Ser Ser
            115

<210> SEQ ID NO 10
<211> LENGTH: 118
<212> TYPE: PRT
<213> ORGANISM: Artificial
<220> FEATURE:
<223> OTHER INFORMATION: VH sequence of 02-237 (anti-CD46)
```

<400> SEQUENCE: 10

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Gly Phe Pro Arg Thr Ser Phe Asp Ser Trp Gly Gln Gly Thr
            100                 105                 110

Leu Val Thr Val Ser Ser
        115
```

<210> SEQ ID NO 11
<211> LENGTH: 369
<212> TYPE: DNA
<213> ORGANISM: Artificial
<220> FEATURE:
<223> OTHER INFORMATION: VH sequence of clone B28 (anti-CD22 phage)
<220> FEATURE:
<221> NAME/KEY: CDS
<222> LOCATION: (1)..(369)

<400> SEQUENCE: 11

```
atg gcc gag gtg cag ctg gtg gag tct ggg gga ggt gtg gta cgg cct     48
Met Ala Glu Val Gln Leu Val Glu Ser Gly Gly Gly Val Val Arg Pro
1               5                   10                  15 gga ggg tcc ctg aga ctc tcc tgt gca gcc tct gga ttc acc ttt gat     96
Gly Gly Ser Leu Arg Leu Ser Cys Ala Ala Ser Gly Phe Thr Phe Asp
            20                  25                  30 gat tat ggc atg agc tgg gtc cgc caa gct cca ggg aag ggg ctg gag    144
Asp Tyr Gly Met Ser Trp Val Arg Gln Ala Pro Gly Lys Gly Leu Glu
        35                  40                  45 tgg gtc tct ggt att aat tgg aat ggt ggt agc aca ggt tat gca gac    192
Trp Val Ser Gly Ile Asn Trp Asn Gly Gly Ser Thr Gly Tyr Ala Asp
50                  55                  60 tct gtg aag ggc cga ttc acc atc tcc aga gac aac gcc aag aac tcc    240
Ser Val Lys Gly Arg Phe Thr Ile Ser Arg Asp Asn Ala Lys Asn Ser
65                  70                  75                  80 ctg tat ctg caa atg aac agt ctg aga gcc gag gac acg gcc gtg tat    288
Leu Tyr Leu Gln Met Asn Ser Leu Arg Ala Glu Asp Thr Ala Val Tyr
            85                  90                  95 tac tgt gca aga ggc ttt ctt cgt ttt gct tcc tcc tgg ttt gac tat    336
Tyr Cys Ala Arg Gly Phe Leu Arg Phe Ala Ser Ser Trp Phe Asp Tyr
            100                 105                 110 tgg ggc caa ggt acc ctg gtc acc gtc tcg aga                        369
Trp Gly Gln Gly Thr Leu Val Thr Val Ser Arg
        115                 120
```

<210> SEQ ID NO 12
<211> LENGTH: 123
<212> TYPE: PRT
<213> ORGANISM: Artificial
<220> FEATURE:
<223> OTHER INFORMATION: VH sequence of clone B28 (anti-CD22 phage)

<400> SEQUENCE: 12

```
Met Ala Glu Val Gln Leu Val Glu Ser Gly Gly Val Val Arg Pro
1               5                   10                  15

Gly Gly Ser Leu Arg Leu Ser Cys Ala Ala Ser Gly Phe Thr Phe Asp
            20                  25                  30

Asp Tyr Gly Met Ser Trp Val Arg Gln Ala Pro Gly Lys Gly Leu Glu
            35                  40                  45

Trp Val Ser Gly Ile Asn Trp Asn Gly Gly Ser Thr Gly Tyr Ala Asp
50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Gly Phe Leu Arg Phe Ala Ser Ser Trp Phe Asp Tyr
            100                 105                 110

Trp Gly Gln Gly Thr Leu Val Thr Val Ser Arg
            115                 120
```

<210> SEQ ID NO 13
<211> LENGTH: 369
<212> TYPE: DNA
<213> ORGANISM: Artificial
<220> FEATURE:
<223> OTHER INFORMATION: VH sequence of clone II-2 (anti-CD72 phage)
<220> FEATURE:
<221> NAME/KEY: CDS
<222> LOCATION: (1)..(369)

<400> SEQUENCE: 13

```
atg gcc cag gtg cag ctg gtg cag tct ggg gct gag gtg aag aag cct      48
Met Ala Gln Val Gln Leu Val Gln Ser Gly Ala Glu Val Lys Lys Pro
1               5                   10                  15 ggg gcc tca gtg aag gtt tcc tgc aag gca tct gga tac acc ttc acc      96
Gly Ala Ser Val Lys Val Ser Cys Lys Ala Ser Gly Tyr Thr Phe Thr
            20                  25                  30 agc tac tat atg cac tgg gtg cga cag gcc cct gga caa ggg ctt gag     144
Ser Tyr Tyr Met His Trp Val Arg Gln Ala Pro Gly Gln Gly Leu Glu
            35                  40                  45 tgg atg gga ata atc aac cct agt ggt ggt ggc aca agc tac gca cag     192
Trp Met Gly Ile Ile Asn Pro Ser Gly Gly Gly Thr Ser Tyr Ala Gln
50                  55                  60 aag ttc cag ggc aga gtc acc atg acc agg gac acg tcc acg agc aca     240
Lys Phe Gln Gly Arg Val Thr Met Thr Arg Asp Thr Ser Thr Ser Thr
65                  70                  75                  80 gtc tac atg gag ctg agc agc ctg aga tct gag gac acg gcc gtg tat     288
Val Tyr Met Glu Leu Ser Ser Leu Arg Ser Glu Asp Thr Ala Val Tyr
                85                  90                  95 tac tgt gca aga gac tac tat gtt acg tat gat tcc tgg ttt gac tcc     336
Tyr Cys Ala Arg Asp Tyr Tyr Val Thr Tyr Asp Ser Trp Phe Asp Ser
            100                 105                 110 tgg ggc caa ggt acc ctg gtc acc gtc tcg aga                         369
Trp Gly Gln Gly Thr Leu Val Thr Val Ser Arg
            115                 120
```

<210> SEQ ID NO 14
<211> LENGTH: 123
<212> TYPE: PRT
<213> ORGANISM: Artificial
<220> FEATURE:
<223> OTHER INFORMATION: VH sequence of clone II-2 (anti-CD72 phage)

<400> SEQUENCE: 14

Met Ala Gln Val Gln Leu Val Gln Ser Gly Ala Glu Val Lys Lys Pro
1               5                   10                  15

Gly Ala Ser Val Lys Val Ser Cys Lys Ala Ser Gly Tyr Thr Phe Thr
            20                  25                  30

Ser Tyr Tyr Met His Trp Val Arg Gln Ala Pro Gly Gln Gly Leu Glu
        35                  40                  45

Trp Met Gly Ile Ile Asn Pro Ser Gly Gly Thr Ser Tyr Ala Gln
    50                  55                  60

Lys Phe Gln Gly Arg Val Thr Met Thr Arg Asp Thr Ser Thr Ser Thr
65                  70                  75                  80

Val Tyr Met Glu Leu Ser Ser Leu Arg Ser Glu Asp Thr Ala Val Tyr
                85                  90                  95

Tyr Cys Ala Arg Asp Tyr Tyr Val Thr Tyr Asp Ser Trp Phe Asp Ser
            100                 105                 110

Trp Gly Gln Gly Thr Leu Val Thr Val Ser Arg
        115                 120

<210> SEQ ID NO 15
<211> LENGTH: 360
<212> TYPE: DNA
<213> ORGANISM: Artificial
<220> FEATURE:
<223> OTHER INFORMATION: VH sequence of clone I-2 (anti-class II phage)
<220> FEATURE:
<221> NAME/KEY: CDS
<222> LOCATION: (1)..(360)

<400> SEQUENCE: 15 atg gcc gag gtg cag ctg gtg gag tct ggg gga ggc ttg gta cag cct      48
Met Ala Glu Val Gln Leu Val Glu Ser Gly Gly Gly Leu Val Gln Pro
1               5                   10                  15 ggc agg tcc ctg aga ctc tcc tgt gca gcc tct gga ttc acc ttt gat      96
Gly Arg Ser Leu Arg Leu Ser Cys Ala Ala Ser Gly Phe Thr Phe Asp
            20                  25                  30 gat tat gcc atg cac tgg gtc cgg caa gct cca ggg aag ggc ctg gag     144
Asp Tyr Ala Met His Trp Val Arg Gln Ala Pro Gly Lys Gly Leu Glu
        35                  40                  45 tgg gtc tca ggt att agt tgg aat agt ggt agc ata ggc tat gcg gac     192
Trp Val Ser Gly Ile Ser Trp Asn Ser Gly Ser Ile Gly Tyr Ala Asp
    50                  55                  60 tct gtg aag ggc cga ttc acc atc tcc aga gac aac gcc aag aac tcc     240
Ser Val Lys Gly Arg Phe Thr Ile Ser Arg Asp Asn Ala Lys Asn Ser
65                  70                  75                  80 ctg tat ctg caa atg aac agt ctg aga gct gag gac acg gcc gtg tat     288
Leu Tyr Leu Gln Met Asn Ser Leu Arg Ala Glu Asp Thr Ala Val Tyr
                85                  90                  95 tac tgt gca agg gac ctt tat ctt gcg cat ttt gac tac tgg ggc caa     336
Tyr Cys Ala Arg Asp Leu Tyr Leu Ala His Phe Asp Tyr Trp Gly Gln
            100                 105                 110 ggt acc ctg gtc acc gtc tcg aga                                     360
Gly Thr Leu Val Thr Val Ser Arg
        115                 120

<210> SEQ ID NO 16
<211> LENGTH: 120
<212> TYPE: PRT
<213> ORGANISM: Artificial
<220> FEATURE:
<223> OTHER INFORMATION: VH sequence of clone I-2 (anti-class II phage)

-continued

<400> SEQUENCE: 16

Met Ala Glu Val Gln Leu Val Glu Ser Gly Gly Leu Val Gln Pro
1               5                   10                  15

Gly Arg Ser Leu Arg Leu Ser Cys Ala Ala Ser Gly Phe Thr Phe Asp
            20                  25                  30

Asp Tyr Ala Met His Trp Val Arg Gln Ala Pro Gly Lys Gly Leu Glu
        35                  40                  45

Trp Val Ser Gly Ile Ser Trp Asn Ser Gly Ser Ile Gly Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Asp Leu Tyr Leu Ala His Phe Asp Tyr Trp Gly Gln
            100                 105                 110

Gly Thr Leu Val Thr Val Ser Arg
        115                 120

<210> SEQ ID NO 17
<211> LENGTH: 336
<212> TYPE: DNA
<213> ORGANISM: Artificial
<220> FEATURE:
<223> OTHER INFORMATION: common VL sequence of clones B28 (anti-CD22
      phage), II-2 (anti-CD72 phage) and I-2 (anti-class II phage)
<220> FEATURE:
<221> NAME/KEY: CDS
<222> LOCATION: (1)..(336)

<400> SEQUENCE: 17 tcg tct gag ctg act cag gac cct gct gtg tct gtg gcc ttg gga cag     48
Ser Ser Glu Leu Thr Gln Asp Pro Ala Val Ser Val Ala Leu Gly Gln
1               5                   10                  15 aca gtc agg atc aca tgc caa gga gac agc ctc aga agc tat tat gca     96
Thr Val Arg Ile Thr Cys Gln Gly Asp Ser Leu Arg Ser Tyr Tyr Ala
            20                  25                  30 agc tgg tac cag cag aag cca gga cag gcc cct gta ctt gtc atc tat    144
Ser Trp Tyr Gln Gln Lys Pro Gly Gln Ala Pro Val Leu Val Ile Tyr
        35                  40                  45 ggt aaa aac aac cgg ccc tca ggg atc cca gac cga ttc tct ggc tcc    192
Gly Lys Asn Asn Arg Pro Ser Gly Ile Pro Asp Arg Phe Ser Gly Ser
    50                  55                  60 agc tca gga aac aca gct tcc ttg acc atc act ggg gct cag gcg gaa    240
Ser Ser Gly Asn Thr Ala Ser Leu Thr Ile Thr Gly Ala Gln Ala Glu
65                  70                  75                  80 gat gag gct gac tat tac tgt aac tcc cgg gac agc agt ggt aac cat    288
Asp Glu Ala Asp Tyr Tyr Cys Asn Ser Arg Asp Ser Ser Gly Asn His
                85                  90                  95 gtg gta ttc ggc gga ggg acc aag ctg acc gtc cta ggt gcg gcc gca    336
Val Val Phe Gly Gly Gly Thr Lys Leu Thr Val Leu Gly Ala Ala Ala
            100                 105                 110

<210> SEQ ID NO 18
<211> LENGTH: 112
<212> TYPE: PRT
<213> ORGANISM: Artificial
<220> FEATURE:
<223> OTHER INFORMATION: common VL sequence of clones B28 (anti-CD22
      phage), II-2 (anti-CD72 phage) and I-2 (anti-class II phage)

```
<400> SEQUENCE: 18

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Gly Ala Ala Ala
            100                 105                 110
```

RECOMBINANT PRODUCTION OF MIXTURES OF ANTIBODIES

CROSS-REFERENCE TO RELATED APPLICATIONS

This application is a divisional patent application of co-pending application Ser. No. 11/593,279, filed Nov. 6, 2006, now U.S. Pat. No. 7,429,486 which is a divisional patent application of patent application Ser. No. 11/039,767, filed Jan. 18, 2005, now U.S. Pat. No. 7,262,028, issued Aug. 28, 2007, which is a continuation of PCT International Patent Application No. PCT/EP2003/007690, filed on Jul. 15, 2003, designating the United States of America, published, in English, as International Publication No. WO 2004/009618 A2 on Jan. 29, 2004, which itself claims the benefit of PCT International Patent Application No. PCT/EP03/50201, filed May 27, 2003, and European Patent Application No. 02077953.4, filed Jul. 18, 2002, and U.S. Provisional Patent Application Ser. No. 60/397,066, filed Jul. 18, 2002, the contents of the entirety of each of which are incorporated by reference.

STATEMENT ACCORDING TO 37 C.F.R. §1.52(e)(5)

Sequence Listing Submitted on Compact Disc

Pursuant to 37 C.F.R. §1.52(e)(1)(iii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "0079WO00ORD.ST25.txt" which is 27 KB and created on Jan. 11, 2005.

TECHNICAL FIELD

The invention relates to the field of biotechnology, and more particularly, to the field of medicine and the production of antibodies, and even more particularly, to the production of mixtures of antibodies.

BACKGROUND

The essential function of the immune system is the defense against infection. The humoral immune system combats molecules recognized as non-self, such as pathogens, using immunoglobulins. These immunoglobulins, also called antibodies, are raised specifically against the infectious agent, which acts as an antigen, upon first contact (Roitt, Essential Immunology, Blackwell Scientific Publications, fifth edition, 1984; all references cited herein are incorporated in their entirety by reference). Antibodies are multivalent molecules comprising heavy (H) chains and light (L) chains joined with interchain disulfide bonds. Several isotypes of antibodies are known, including IgG1, IgG2, IgG3, IgG4, IgA, IgD, IgE, and IgM. An IgG contains two heavy and two light chains. Each chain contains constant (C) and variable (V) regions, which can be broken down into domains designated $C_{H1}$, $C_{H2}$, $C_{H3}$, $V_H$, and $C_L$, $V_L$ (FIG. 1). Antibody binds to antigen via the variable region domains contained in the Fab portion and, after binding, can interact with molecules and cells of the immune system through the constant domains, mostly through the Fc portion.

B-lymphocytes can produce antibodies in response to exposure to biological substances like bacteria, viruses and their toxic products. Antibodies are generally epitope-specific and bind strongly to substances carrying these epitopes. The hybridoma technique (Kohler and Milstein, 1975) makes use of the ability of B-cells to produce monoclonal antibodies to specific antigens and to subsequently produce these monoclonal antibodies by fusing B-cells from mice exposed to the antigen of interest to immortalized murine plasma cells. This technology resulted in the realization that monoclonal antibodies produced by hybridomas could be used in research, diagnostics and therapies to treat different kinds of diseases like cancer and auto-immune-related disorders.

Because antibodies that are produced in mouse hybridomas can induce strong immune responses in humans, it has been appreciated in the art that antibodies required for successful treatment of humans needed to be less immunogenic or, preferably, non-immunogenic. For this to be done, murine antibodies were first engineered by replacing the murine constant regions with human constant regions (referred to as chimeric antibodies). Subsequently, domains between the complementarity-determining regions (CDRs) in the variable domains, the so-called framework regions, were replaced by their human counterparts (referred to as humanized antibodies). The final stage in this humanization process has been the production of fully human antibodies.

In the art, bispecific antibodies, which have binding specificities for two different antigens, have also been described. These are generally used to target a therapeutic or diagnostic moiety, for instance, T-cell, a cytotoxic trigger molecule, or a chelator that binds a radionuclide, that is recognized by one variable region of the antibody to a cell that is recognized by the other variable region of the antibody, for instance, a tumor cell (for bispecific antibodies, see Segal et al., 2001).

One very useful method known in the art to obtain fully human monoclonal antibodies with desirable binding properties, employs phage display libraries. This is an in vitro, recombinant DNA-based, approach that mimics key features of the humoral immune response (for phage display methods, see, e.g., C. F. Barbas III et al., *Phage Display, A laboratory manual*, Cold Spring Harbor Laboratory Press, Cold Spring Harbor, N.Y., 2001). For the construction of phage display libraries, collections of human monoclonal antibody heavy- and light-chain variable region genes are expressed on the surface of bacteriophage particles, usually in single-chain Fv (scFv) or in Fab format. Large libraries of antibody fragment-expressing phages typically contain more than $10^9$ antibody specificities and may be assembled from the immunoglobulin V regions expressed in the B lymphocytes of immunized or non-immunized individuals.

Alternatively, phage display libraries may be constructed from immunoglobulin variable regions that have been partially assembled or rearranged in vitro to introduce additional antibody diversity in the library (semi-synthetic libraries) (De Kruif et al., 1995b). For example, in vitro-assembled variable regions contain stretches of synthetically produced, randomized or partially randomized DNA in those regions of the molecules that are important for antibody specificity.

The genetic information encoding the antibodies identified by phage display can be used for cloning the antibodies in a desired format, for instance, IgG, IgA or IgM, to produce the antibody with recombinant DNA methods (Boel et al., 2000).

An alternative method to provide fully human antibodies uses transgenic mice that comprise genetic material encoding a human immunoglobulin repertoire (Fishwild et al., 1996; Mendez et al., 1997). Such mice can be immunized with a target antigen and the resulting immune response will produce fully human antibodies. The sequences of these antibodies can be used in recombinant production methods.

Production of monoclonal antibodies is routinely performed by use of recombinant expression of the nucleic acid sequences encoding the H and L chains of antibodies in host cells (see, e.g., EP0120694; EP0314161; EP0481790; U.S. Pat. No. 4,816,567; WO 00/63403, the contents of the entirety of each which are incorporated herein by reference).

To date, many different diseases are being treated with either humanized or fully human monoclonal antibodies. Products based on monoclonal antibodies that are currently approved for use in humans include HERCEPTIN™ (trastuzumab, anti-Her2/Neu), REOPRO™ (abciximab, anti-Glycoprotein IIB/IIIA receptor), MYLOTARG™ (gemtuzumab, anti-CD33), RITUXAN™ (Rituximab, anti-CD20), SIMULECT™ (basiliximab, anti-CD25), REMICADE™ (infliximab, anti-TNF), SYNAGIS™ (palivizumab, anti-RSV), ZENAPAX™ (daclizumab, IL2-receptor), and CAMPATH™ (alemtuzumab, anti-CD52). Despite these successes, there is still room for new antibody products and for considerable improvement of existing antibody products.

The use of monoclonal antibodies in cancer treatment has shown that so-called "antigen-loss tumor variants" can arise, making the treatment with the monoclonal antibody less effective. Treatment with the very successful monoclonal antibody RITUXIMAB® (anti-CD20) has, for instance, shown that antigen-loss escape variants can occur, leading to relapse of the lymphoma (Massengale et al., 2002). In the art, the potency of monoclonal antibodies has been increased by fusing them to toxic compounds, such as radionuclides, toxins, cytokines, and the like. Each of these approaches, however, has its limitations, including technological and production problems and/or high toxicity.

Furthermore, it appears that the gain in specificity of monoclonal antibodies compared to traditional undefined polyclonal antibodies, comes at the cost of loss of efficacy. In vivo, antibody responses are polyclonal in nature, i.e., a mixture of antibodies is produced because various B-cells respond to the antigen, resulting in various specificities being present in the polyclonal antibody mixture. Polyclonal antibodies can also be used for therapeutic applications, for instance, for passive vaccination or for active immunotherapy, and currently are usually derived from pooled serum from immunized animals or from humans who recovered from the disease. The pooled serum is purified into the proteinaceous or gamma globulin fraction, so named because it contains predominantly IgG molecules.

Polyclonal antibodies that are currently used for treatment include anti-rhesus polyclonal antibodies, gamma globulin for passive immunization, anti-snake venom polyclonal (Cro-Fab), THYMOGLOBULIN™ for allograft rejection, anti-digoxin to neutralize the heart drug digoxin, and anti-rabies polyclonal antibodies. In currently marketed therapeutic antibodies, an example of the higher efficacy of polyclonal antibodies compared to monoclonal antibodies can be found in the treatment of acute transplant rejection with anti-T-cell antibodies. The monoclonal antibodies on the market (anti-CD25 BASILIXIMAB®) are less efficacious than a rabbit polyclonal antibody against thymocytes (THYMOGLOBULIN™) (press releases dated Mar. 12, Apr. 29, and Aug. 26, 2002, on sangstat.com). The use of pooled human sera, however, potentially bears the risk of infections with viruses such as HIV or hepatitis, with toxins such as lipopolysaccharide, with proteinaceous infectious agents such as prions, and with unknown infectious agents. Furthermore, the supply that is available is limited and insufficient for widespread human treatments. Problems associated with the current application of polyclonal antibodies derived from animal sera in the clinic include a strong immune response of the human immune system against such foreign antibodies. Therefore, such polyclonals are not suitable for repeated treatment or for treatment of individuals that were injected previously with other serum preparations from the same animal species.

The art describes the idea of the generation of animals with a human immunoglobulin repertoire, which can subsequently be used for immunization with an antigen to obtain polyclonal antibodies against this antigen from the transgenic animals (WO 01/19394, the entirety of which is incorporated herein by reference). However, many technological hurdles still will have to be overcome before such a system is a practical reality in larger animals than mice and it will take years of development before such systems can provide the polyclonal antibodies in a safe and consistent manner in sufficient quantities. Moreover, antibodies produced from pooled sera, whether being from human or animal origin, will always comprise a high amount of unrelated and undesired specificities, as only a small percentage of the antibodies present in a given serum will be directed against the antigen used for immunization. It is, for instance, known that in normal, i.e., non-transgenic, animals, about 1% to 10% of the circulating immunoglobulin fraction is directed against the antigen used for hyper-immunization; hence, the vast majority of circulating immunoglobulins is not specific.

One approach towards expression of polyclonal antibody libraries has been described (WO 95/20401; U.S. Pat. Nos. 5,789,208 and 6,335,163, the contents of the entirety of each of which are incorporated herein by reference). A polyconal library of Fab antibody fragments is expressed using a phage display vector and selected for reactivity towards an antigen. To obtain a sub-library of intact polyconal antibodies, the selected heavy and light chain-variable region gene combinations are transferred en mass as linked pairs to a eukaryotic-expression vector that provides constant region genes. Upon transfection of this sub-library into myeloma cells, stable clones produce monoclonal antibodies that can be mixed to obtain a polyclonal antibody mixture. While in theory it would be possible to obtain polyclonal antibodies directly from a single recombinant production process using this method by culturing a mixed population of transfected cells, potential problems would occur concerning the stability of the mixed cell population and, hence, the consistency of the produced polyclonal antibody mixture. The control of a whole population of different cells in a pharmaceutically acceptable large-scale process (i.e., industrial) is a daunting task. It would seem that characteristics, such as growth rates of the cells and production rates of the antibodies, should remain stable for all of the individual clones of the non-clonal population in order to keep the ratio of antibodies in the polyclonal antibody mixture more or less constant.

Thus, while the need for mixtures of antibodies may have been recognized in the art, no acceptable solutions exist to economically make mixtures of antibodies in a pharmaceutically acceptable way.

SUMMARY OF THE INVENTION

The invention provides means for producing a mixture of antibodies in recombinant hosts.

In one aspect, the invention provides for a method of producing a mixture of antibodies in a recombinant host, the method comprising expressing in a recombinant host cell a nucleic acid sequence or nucleic acid sequences encoding at least one light chain and at least three different heavy chains that are capable of pairing with at least one light chain. A further aspect of the invention is the elimination of the production of potentially non-functional light-heavy chain pairing by using pre-selected combinations of heavy and light chains. It has been recognized that phage display libraries built from a single light chain and many different heavy chains can encode antibody fragments with very distinct binding properties. This feature can be used to find different antibodies having the same light chain but different heavy chains, against the same target or different targets, wherein a target can be a whole antigen or an epitope thereof. Such different targets may, for instance, be on the same surface (e.g., cell or tissue). Such antibody fragments obtained by phage display can be cloned into vectors for the desired format, e.g., IgG, IgA or IgM, and the nucleic acid sequences encoding these formats can be used to transfect host cells. In one approach, H and L chains can be encoded by different constructs that, upon transfection into a cell wherein they are expressed, give rise to intact Ig molecules. When different H chain constructs are transfected into a cell with a single L chain construct, H and L chains will be assembled to form all possible combinations. However, in contrast to approaches where different light chains are expressed, such as for the production of bispecific antibodies, this method will result only in functional binding regions. It would be particularly useful when the host, for example, a single cell line, is capable of expressing acceptable levels of recombinant antibodies without the necessity to first amplify in the cell the nucleic acid sequences encoding the antibodies. The advantage is that cell lines with only a limited copy number of the nucleic acids are expected to be genetically more stable, because there will be less recombination between the sequences encoding the heavy chains, than in cell lines where a multitude of these copies is present. A cell line suitable for use in the methods according to the invention is the human cell line PER.C6® (human retina cells that express adenovirus E1A and E1B proteins). Using this method, a mixture of antibodies with defined specificities can be produced from a single cell clone in a safe, controlled, and consistent manner.

In certain embodiments, the invention provides a method for producing a mixture of antibodies in a recombinant host, the method comprising expressing a nucleic acid sequence or nucleic acid sequences encoding at least one light chain and at least three different heavy chains that are capable of pairing with at least one light chain in a recombinant host cell. In certain embodiments, the recombinant host cell comprises a nucleic acid sequence encoding a common light chain that is capable of pairing with at least three different heavy chains, such that the produced antibodies comprise a common light chain. Those of skill in the art will recognize that "common" also refers to functional equivalents of the light chain of which the amino acid sequence is not identical. Many variants of the light chain exist wherein mutations (deletions, substitutions, additions) are present that do not materially influence the formation of functional binding regions.

The invention further provides a composition comprising a mixture of recombinantly produced antibodies, wherein at least three different heavy chain sequences are represented in the mixture. In certain embodiments, the light chains of such mixtures have a common sequence. The mixture of antibodies can be produced by the method according to the invention. Preferably, the mixture of antibodies is more efficacious than the individual antibodies it comprises. More preferably, the mixture acts synergistically in a functional assay.

The invention further provides a recombinant host cell for producing mixtures of antibodies and methods for making such host cells.

Independent clones obtained from the transfection of nucleic acid sequences encoding a light chain and more than one heavy chain may express the different antibodies in the mixture at different levels. It is another aspect of the invention to select a clone using a functional assay for the most potent mixture of antibodies. The invention, therefore, further provides a method for identifying at least one host cell clone that produces a mixture of antibodies, wherein the mixture of antibodies has a desired effect according to a functional assay, the method comprising: (i) providing a host cell with nucleic acid sequences encoding at least one light chain and nucleic acid sequences encoding at least two different heavy chains, wherein the heavy and light chains are capable of pairing with each other; (ii) culturing at least one clone of the host cell under conditions conducive to expression of the nucleic acid sequences; (iii) screening at least one clone of the host cell for production of a mixture of antibodies having the desired effect by a functional assay; and (iv) identifying at least one clone that produces a mixture of antibodies having the desired effect. This method, as used herein, can be performed using high-throughput procedures if desired. The clones identified by the method can be used to produce antibody mixtures according to the invention.

In certain embodiments, the invention further provides transgenic non-human animals and transgenic plants or transgenic plant cells capable of expressing mixtures of antibodies and mixtures of antibodies produced by these.

In certain embodiments, the invention further provides pharmaceutical compositions comprising a mixture of recombinantly produced antibodies and a suitable carrier.

In certain embodiments, the invention further provides mixtures of antibodies for use in the treatment or diagnosis and for the preparation of a medicament for use in the treatment or diagnosis of a disease or disorder in a human or animal subject.

In certain embodiments, the invention further provides a method for producing a mixture of antibodies comprising different isotypes from a single host cell clone.

In certain embodiments, the invention further provides a method for identifying a mixture of antibodies having a desired effect in a functional assay.

In certain embodiments, the invention further provides a method for producing a mixture of antibodies that are capable of binding to a target, the method comprising: i) bringing a phage library comprising antibodies into contact with material comprising a target, ii) at least one step of selecting phages binding to the target, iii) identifying at least two phages that comprise antibodies binding to the target, wherein at least two antibodies comprise a common light chain, iv) introducing a nucleic acid sequence encoding the light chain and a nucleic acid sequence or sequences encoding the heavy chains of at least two antibodies into a host cell, v) culturing a clone of the host cell under conditions conducive to expression of the nucleic acid sequences.

BRIEF DESCRIPTION OF THE FIGURES

FIGS. 3A and 3B show a sequence alignment of $V_L$ (FIG. 3A) and $V_H$ (FIG. 3B) of K53, UBS-54 and 02-237. The DNA sequence of common $V_L$ of UBS54 and K53 is SEQ ID NO:1, while the amino acid sequence is given as SEQ ID NO:2. DNA sequences of $V_L$ of 02-237, $V_H$ of UBS54, K53 and 02-237 are SEQ ID NOS:3, 5, 7 and 9, respectively, while the amino acid sequences are given in SEQ ID NOS:4, 6, 8 and 10, respectively.

FIGS. 7A and 7B show the sequence of $V_H$ and $V_L$ of phages directed against CD22 (clone B28), CD72 (clone II-2) (FIG. 7A), and HLA-DR (class II; clone I-2) (FIG. 7B). DNA sequences of $V_L$ of clones B28, II-2 and 1-2 are SEQ ID NOS:11, 13 and 15, respectively, while the amino acid sequences are SEQ ID NOS:12, 14 and 16, respectively. DNA sequence of the common light chain of these clones is SEQ ID NO:17, while the amino acid sequence is SEQ ID NO:18.

FIGS. 12A-12E depict DNA and protein sequences of variable domains of heavy chains of K53 (FIG. 12A), UBS54 (FIG. 12C) and 02-237 (FIG. 12B) IgG (SEQ ID NOS:7, 9 and 5, respectively) and light chains (SEQ ID NOS:1 and 3, respectively, for K53/UBS54 (FIG. 12D) and 02-237 IgG (FIG. 12E)).

FIG. 13 shows alignment of the variable sequences of the heavy chains of K53, 02-237 and UBS54 (SEQ ID NOS:7, 9 and 5, respectively). CDR1, CDR2 and CDR3 regions are indicated in bold.

FIG. 14 is a BIACORE™ (surface plasmon resonance) analysis of K53 and 02-237. Affinity-purified human CD46 from LS174T cells was coupled (640 RU) to CM5 chips (BIACORE BR-1000-14™). Binding of 1000 (A), 500 (B), 250 (C), 125 (D), 63 (E), 31 (F), 16 (G), 8 (H) or 0 (I) nM 02-237 or K53 purified from stable PER.C6® (human retina cells that express adenovirus E1A and E1B proteins)-derived cell lines to the CD46 was monitored using a BIACORE 3000™ system at 37° C. Using this experimental set-up, a $K_d$ of $9.1 \times 10^7$ and $2.2 \times 10^8$ was found for K53 and 02-237, respectively.

Purified IgG was dissolved in a 0.1% RAPIGEST™ (Waters) in 50 mM $NH_4HCO_3$. The disulfides were reduced using 1 M DTT (1,4-dithio-DL-threitol), followed by incubation at 65° C. for 30 minutes. Then, for alkylation of all sulfhydryl groups, 1 M iodoacetamide was added, followed by incubation at room temperature for 45 minutes in the dark. Alkylation was stopped by addition of 1 M DTT. The buffer was exchanged to 25 mM $NH_4HCO_3$, pH 7.5. Finally, the antibodies were digested overnight at 37° C. by addition of a freshly prepared trypsin solution in 25 mM $NH_4HCO_3$. The peptide mixture was analyzed by LC-MS. The LC-system consisted of a Vydac reversed-phase C18 column that was eluted by applying a gradient of solvent A (5/95/1 acetonitrile, water, glacial acetic acid v/v/v) and solvent B (90/10/1 acetonitrile, water, glacial acetic acid v/v/v). The LC was on-line coupled to a Q-TOF2 mass spectrometer (Micromass), equipped with an electrospray source operated at 3 kV. Mass spectra were recorded in a positive ion mode from m/z 50 to 1500 at a cone voltage of 35 V. The instrumental resolution of >10,000 enabled unambiguous determination of the charge and, therefore, the mass of most ions up to at least +7. In this way, all peptides were identified according to their molecular weight. The amino acid sequence of the peptide was confirmed by MS/MS-experiments. MS/MS spectra were recorded in a positive ion mode from m/z 50-2000 with collision energy between 20 and 35 eVolts.

Figure 20:
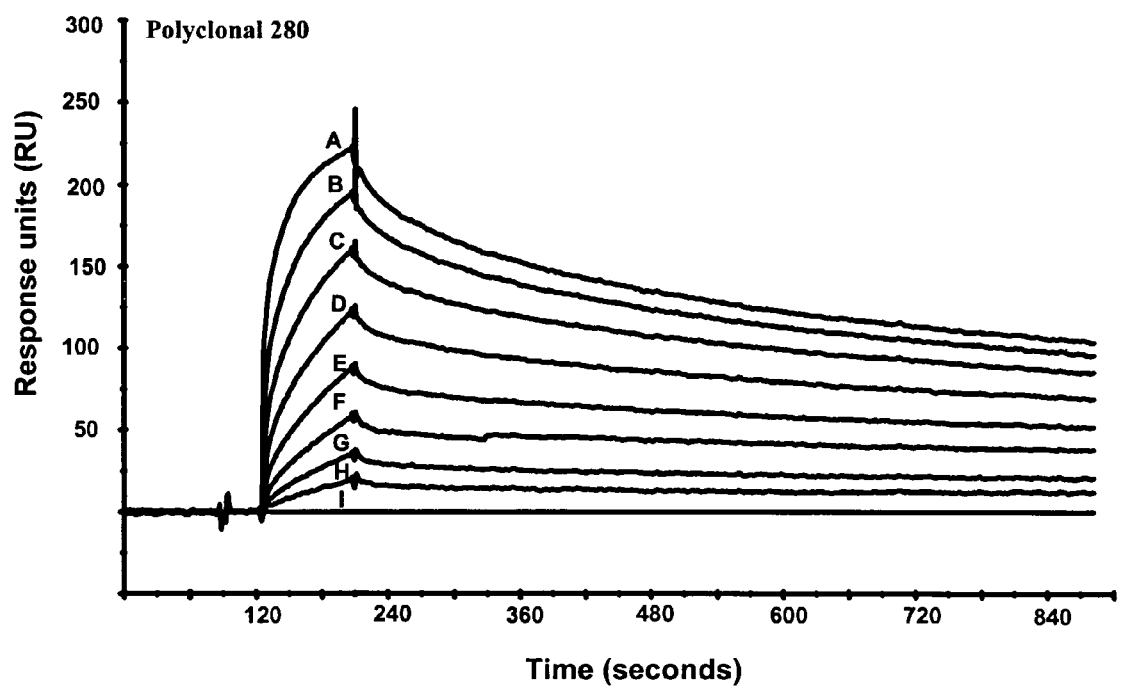

FIG. 20 is a BIACORE™ (surface plasmon resonance) analysis of polyclonal 280. Affinity-purified human CD46 from LS174T cells was coupled (640 RU) to CM5 chips (BIACORE BR-1000-14™). Binding of 1000 (A), 500 (B), 250 (C), 125 (D), 63 (E), 31 (F), 16 (G), 8 (H) or 0 (I) nM Poly1-280 to CD46 was monitored using a BIACORE 3000™ system at 37° C.

FIG. 21 is an IEF analysis of sub-clones from clones poly 1-241, poly 1-280 and poly 1-402 producing a mixture of antibodies.

Panel A contains clones poly 1-241 and poly 1-280. Lane 1 contains a pI marker (Amersham, Cat. No. 17-0471-01). Lane 2 contains isolated IgG from the parent clone poly 1-241 (as in FIG. 18). Lanes 3, 4 and 5, respectively, contain isolated IgG from three independent sub-clones derived from poly 1-241 by limiting dilution. Lane 6 contains isolated IgG from the parent clone poly 1-280 (as in FIG. 18). Lanes 7, 8 and 9, respectively, contain isolated IgG from three independent sub-clones derived from poly 1-280 by limiting dilution.

Panel B contains clone poly 1-402. Lanes 1 and 7 contain a pI marker. Lane 2 contains isolated IgG from the parent clone poly 1-402 (as in FIG. 18). Lanes 3, 4 and 5, respectively, contain isolated IgG from three independent sub-clones derived from poly 1-402 by limiting dilution. Lane 6 contains a control (a 1:1:1 mixture of 02-237, K53 and UBS54).

Figure 22:
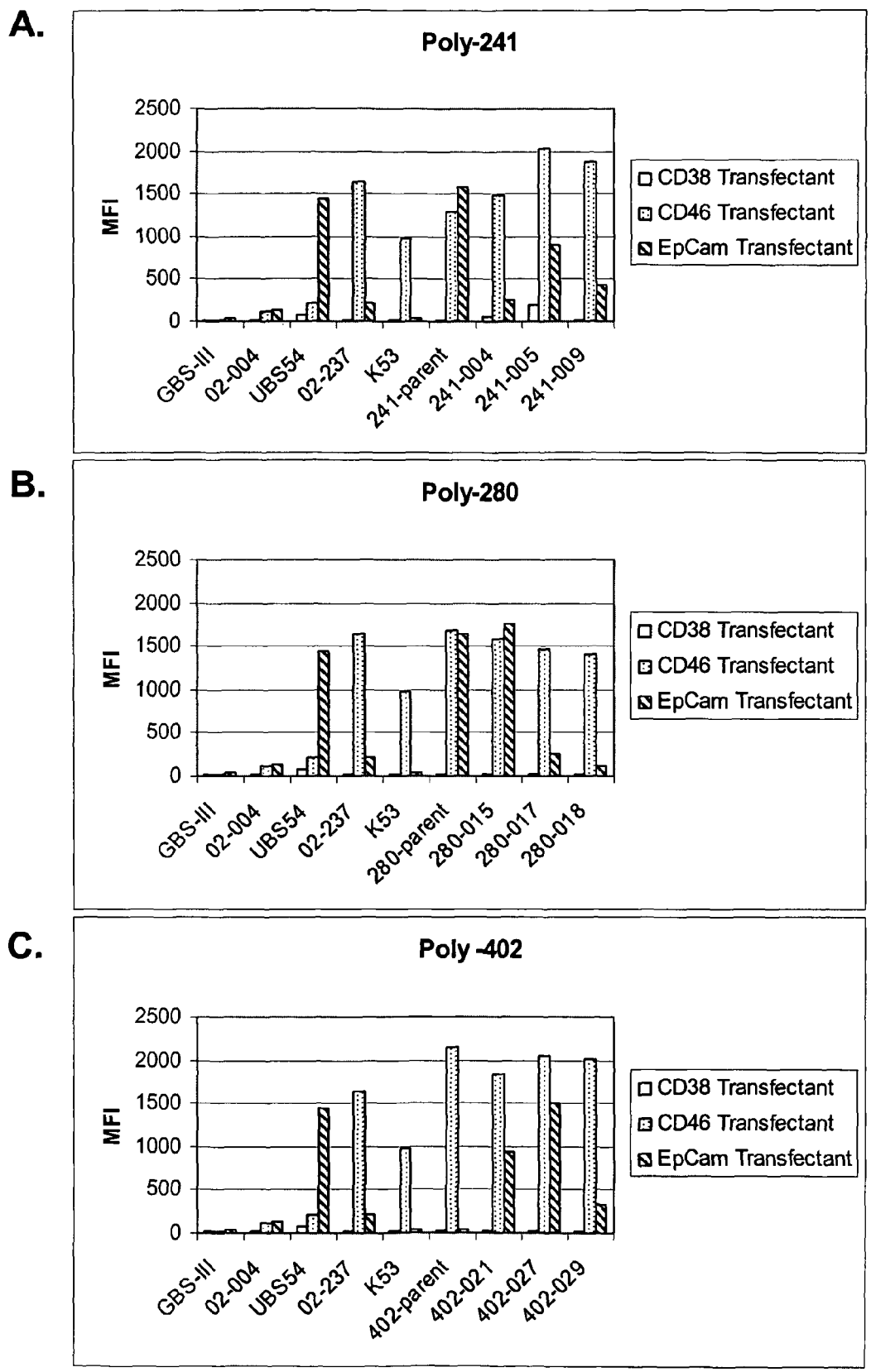

FIG. 22 is a fluorescence activated cell sorting (FACS) analysis of mixtures of antibodies produced from sub-clones of poly 1-241 (A), poly 1-280 (B) and poly 1-402 (C). Binding of the mixtures of antibodies to cells transfected with cDNA of CD46, EpCAM, or a negative control (CD38), was determined with FACS analysis. Mean fluorescent intensity (MFI) is shown for the various parent clones and three independent sub-clones of each. Control antibodies GBS-III (negative control), anti-CD72 (02-004; negative control) and the single antibodies UBS54, 02-237 and K53 are also included.

DETAILED DESCRIPTION OF THE INVENTION

In certain embodiments, also provided is a method for producing a mixture of antibodies in a recombinant host, the method comprising expressing, in a recombinant host cell, a nucleic acid sequence or nucleic acid sequences encoding at least one light chain and at least three different heavy chains that are capable of pairing with at least one light chain. In certain embodiments, the light and heavy chains form functional antigen-binding domains when paired. A functional antigen-binding domain is capable of specifically binding to an antigen.

In certain embodiments, the method for producing a mixture of antibodies according to the invention further comprises the step of recovering the antibodies from the cell or the host cell culture to obtain a mixture of antibodies suitable for further use.

In certain embodiments, a method is provided for production of a mixture of antibodies, the method comprising expressing in a recombinant host cell a nucleic acid sequence encoding a common light chain and nucleic acid sequence or sequences encoding at least three different heavy chains that are capable of pairing with the common light chain, such that the antibodies that are produced comprise common light chains. In one aspect, the common light chain is identical in each light chain/heavy chain pair.

Figure 1:
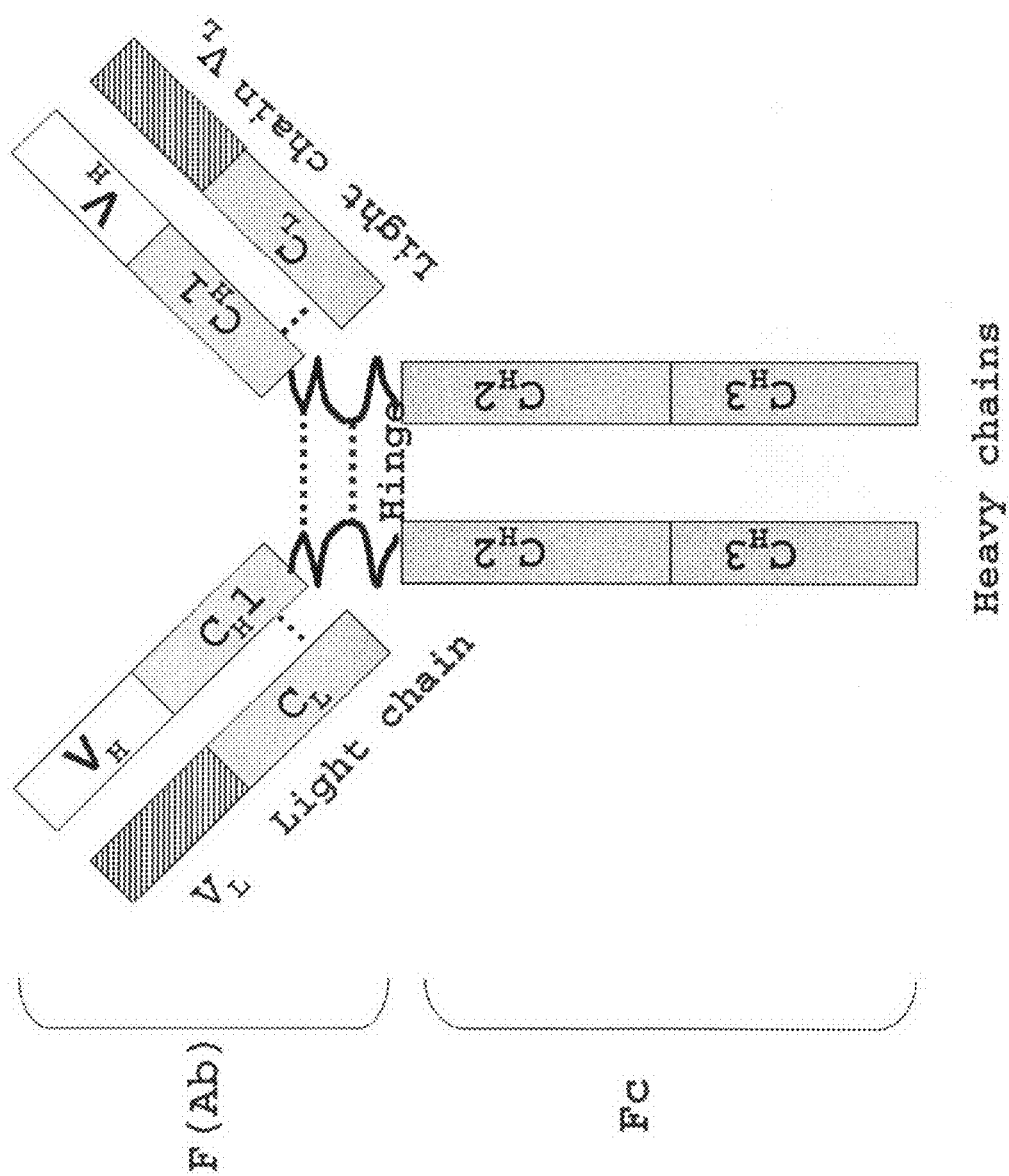
FIG. 1 is a schematic representation of an antibody. The heavy and light chains are paired via interchain disulfide bonds (dotted lines). The heavy chain can be either of the α, γ, μ, δ or ε isotype. The light chain is either λ or κ. An antibody of IgG1 isotype is shown.

The term "antibody," as used herein, means a polypeptide containing one or more domains that bind an epitope on an antigen, where such domains are derived from, or have sequence identity with, the variable region of an antibody. The structure of an antibody is schematically represented in FIG. 1. Examples of antibodies according to the invention include full length antibodies, antibody fragments, bispecific antibodies, immunoconjugates, and the like. An antibody, as used herein, may be isotype IgG1, IgG2, IgG3, IgG4, IgA1, IgA2, IgD, IgE, IgM, and the like, or a derivative of these. Antibody fragments include Fv, Fab, Fab', F(ab')$_2$ fragments, and the like. Antibodies according to the invention can be of any origin, including murine, of more than one origin, e.g., chimeric, humanized, or fully human antibodies. Immunoconjugates comprise antigen-binding domains and a non-antibody part such as a toxin, a radiolabel, an enzyme, and the like.

Figure 2:
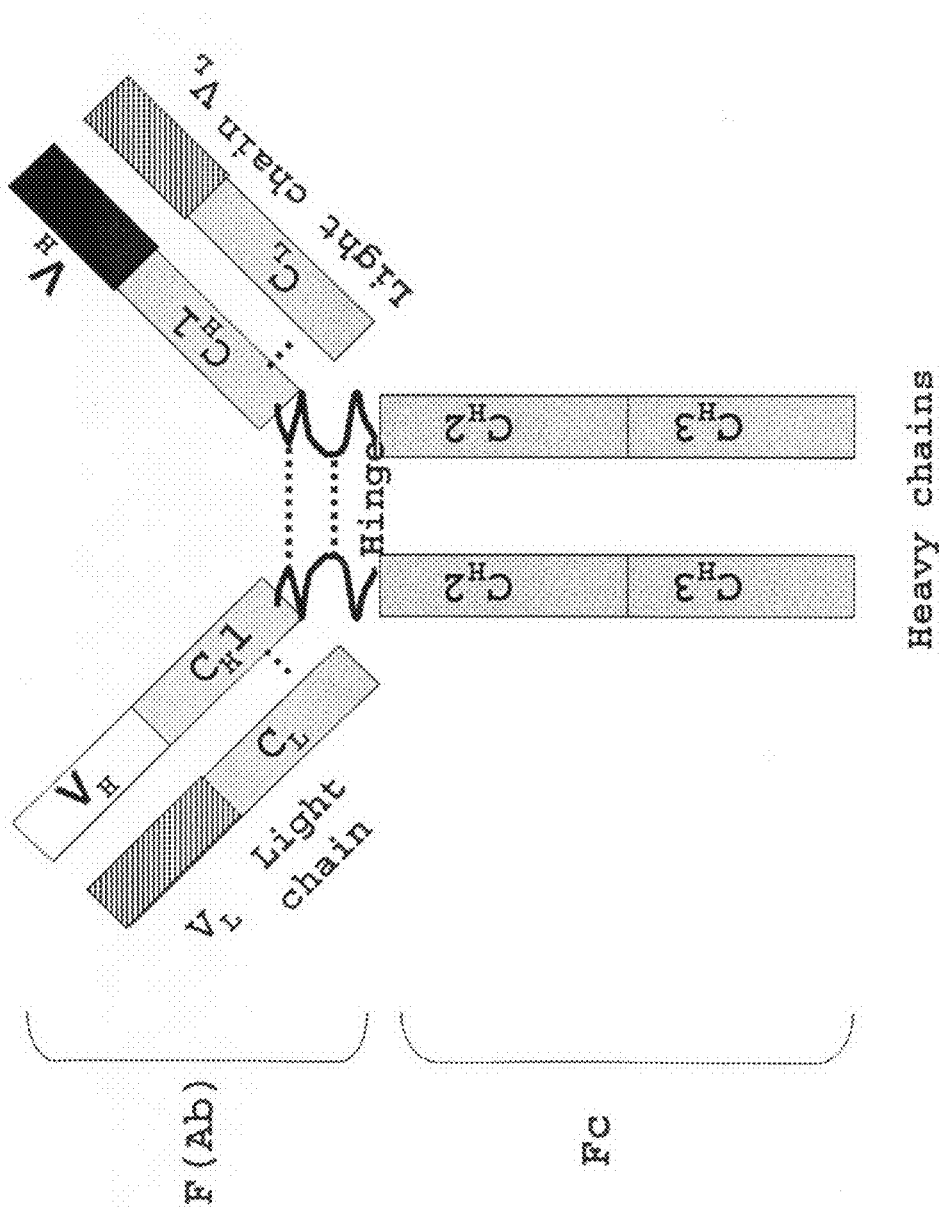
FIG. 2 is a schematic representation of a bispecific monoclonal antibody. A bispecific antibody contains two different functional F(Ab) domains, indicated by the different patterns of the $V_H$-$V_L$ regions.

An "antigen-binding domain" preferably comprises variable regions of a heavy and a light chain and is responsible for specific binding to an antigen of interest. Recombinant antibodies are prepared by expressing both a heavy and a light chain in a host cell. Similarly, by expressing two chains with their respective light chains (or a common light chain), wherein each heavy chain/light chain has its own specificity, so-called "bispecific" antibodies can be prepared. "Bispecific antibodies" comprise two non-identical heavy-light chain combinations (FIG. 2), and both antigen-binding regions of a bispecific antibody may recognize different antigens or different epitopes on an antigen. "Epitope" means a moiety of an antigen to which an antibody binds. A single antigen may have multiple epitopes.

A "common light chain," refers to light chains which may be identical or have amino acid sequence differences. Common light chains may comprise mutations which do not alter the specificity of the antibody when combined with the same heavy chain without departing from the scope of the invention. It is, for instance, possible within the scope of the definition of common light chains as used herein, to prepare or find light chains that are not identical but still functionally equivalent, e.g., by introducing and testing conservative amino acid changes, changes of amino acids in regions that do not or only partly contribute to binding specificity when paired with the heavy chain, and the like. In an exemplary embodiment, the invention provides the use of a common light chain, one identical light chain, to combine with different heavy chains to form antibodies with functional antigen-binding domains. The use of one common light chain avoids the formation of heterodimers in which pairing of light and heavy chains results in antigen-binding domains that are not functional or, in other words, which are not capable of binding to the target antigen or antigens. The use of a common light chain and two heavy chains has been proposed (Merchant et al., 1998; WO 98/50431, the entirety of which are incorporated herein by reference) for a different purpose, viz., to increase the formation of functional bispecific antibodies at the expense of antibody mixture complexity. These publications teach a method for preferentially producing one defined and desired bispecific antibody, thereby minimizing the complexity of the produced mixture. Hence, Merchant specifically teaches to prevent the production of monospecific antibodies because these are undesired byproducts in the process for bispecific antibody production described in those publications. Clearly, there is no teaching in the prior art to prepare a complex mixture of antibodies from a recombinant host cell avoiding the formation of non-functional binding domains or the benefits thereof, let alone how. In the method according to the invention, at least three different heavy chains that are capable of pairing with the common light chain are expressed. In other embodiments, the host cell, as used herein, is provided with nucleic acid sequences encoding for 4, 5, 6, 7, 8, 9, 10, or more, heavy chains capable of pairing with the common light chain, to increase the complexity of the produced mixture of antibodies.

"Different heavy chains," according to the invention, may differ in the variable region and have the same constant region. In other embodiments, where it is clear from the context, they may have the same variable region and differ in the constant region, e.g., be of a different isotype. The use of a mixture of antibodies having different constant regions, such as the Fc-portion, may be advantageous if different arms of the immune system are to be mobilized in the treatment of the human or animal body. In yet other embodiments, also to be clear from the context, both the variable and the constant regions may differ.

A "mixture of antibodies," according to the invention, comprises at least two non-identical antibodies, but may comprise 3, 4, 5, 6, 7, 8, 9, 10, or more, different antibodies and may resemble a polyclonal or at least an oligoclonal antibody mixture with regard to complexity and number of functional antigen-binding molecules. The mixtures produced according to the invention usually will comprise bispecific antibodies. If desired, formation of monospecific antibodies in the mixture can be favored over the formation of bispecific antibodies.

When n heavy chains and one common light chain are expressed, as used herein, in a host cell at equal levels, the theoretical percentage of bispecific antibodies produced by the method according to the invention is $(1-1/n) \times 100\%$. The total number of different antibodies in the mixture produced by the method according to the invention is theoretically $n+\{(n^2-n)/2\}$, of which $(n^2-n/2)$ are bispecific antibodies. Distortion of the ratio of expression levels of the different heavy chains may lead to values deviating from the theoretical values. The amount of bispecific antibodies can also be decreased, compared to these theoretical values, if all heavy chains do not pair with equal efficiency. It is, for instance, possible to engineer the heavy chains, for example, by introducing specific and complementary interaction surfaces between selected heavy chains, to promote homodimer pairing over heterodimer pairing, contrary to what has been proposed by Merchant, supra. Heavy chains may also be selected so as to minimize heterodimer formation in the mixture. A special form of this embodiment involves heavy chains of two or more different isotypes (e.g., IgG1, IgG3, IgA). When heavy chains of different isotype are expressed in the same host cell in accordance with the invention and one light chain that can pair to these heavy chains, the amount of bispecific antibodies will be reduced, possibly to very low or even undetectable levels. Thus, when bispecific antibodies are less desirable, it is possible to produce a mixture of antibodies according to the invention, wherein a nucleic acid sequence encoding a common light chain and nucleic acid sequences encoding at least two different heavy chains with a different variable region capable of pairing to the common light chain are expressed in a recombinant host, and wherein the heavy chains further differ in their constant regions sufficiently to reduce or prevent pairing between the different heavy chains. The mixtures of antibodies may be produced from a clone that was derived from a single host cell, i.e., from a population of cells containing the same recombinant nucleic acid sequences.

It will be understood that the different heavy chains can be encoded on separate nucleic acid molecules, but may also be present on one nucleic acid molecule comprising different regions encoding at least three heavy chains. The nucleic acid molecules usually encode precursors of the light and/or heavy chains, which, when expressed, are secreted from the host cells, thereby becoming processed to yield the mature form. These and other aspects of expressing antibodies in a host cell are well known to those having ordinary skill in the art.

A "recombinant host cell," as used herein, is a cell comprising one or more so-called transgenes, i.e., recombinant nucleic acid sequences not naturally present in the cell. These transgenes are expressed in the host cell to produce recombinant antibodies encoded by these nucleic acid sequences when these cells are cultured under conditions conducive to expression of nucleic acid sequences. The host cell, as used herein, can be present in the form of a culture from a clone that is derived from a single host cell wherein the transgenes have been introduced. To obtain expression of nucleic acid sequences encoding antibodies, it is well known to those skilled in the art that sequences capable of driving such expression can be functionally linked to the nucleic acid sequences encoding the antibodies.

"Functionally linked" is meant to describe that the nucleic acid sequences encoding the antibody fragments or precursors thereof is linked to the sequences capable of driving expression such that these sequences can drive expression of the antibodies or precursors thereof.

Useful expression vectors are available in the art, for example, the pcDNA vector series of Invitrogen. Where the sequence encoding the polypeptide of interest is properly inserted with reference to sequences governing the transcription and translation of the encoded polypeptide, the resulting expression cassette is useful to produce the polypeptide of interest, referred to as expression. Sequences driving expression may include promoters, enhancers and the like, and combinations thereof. These should be capable of functioning in the host cell, thereby driving expression of the nucleic acid sequences that are functionally linked to them. Promoters can be constitutive or regulated and can be obtained from various sources, including viruses, prokaryotic or eukaryotic sources, or artificially designed. Expression of nucleic acids of interest may be from the natural promoter or derivative thereof or from an entirely heterologous promoter. Some well-known and much-used promoters for expression in eukaryotic cells comprise promoters derived from viruses, such as adenovirus, for instance, the E1A promoter, promoters derived from cytomegalovirus (CMV), such as the CMV immediate early (IE) promoter, promoters derived from Simian Virus 40 (SV40), and the like. Suitable promoters can also be derived from eukaryotic cells, such as methallothionein (MT) promoters, elongation factor 1α (EF-1α) promoter, an actin promoter, an immunoglobulin promoter, heat shock promoters, and the like. Any promoter or enhancer/promoter capable of driving expression of the sequence of interest in the host cell is suitable in the invention. In one embodiment, the sequence capable of driving expression comprises a region from a CMV promoter, preferably the region comprising nucleotides −735 to +95 of the CMV immediate early gene enhancer/promoter. The skilled artisan will be aware that the expression sequences used in the invention may suitably be combined with elements that can stabilize or enhance expression, such as insulators, matrix attachment regions, STAR elements (WO 03/004704, the entirety of which is incorporated herein by reference), and the like. This may enhance the stability and/or levels of expression.

Protein production in recombinant host cells has been extensively described, e.g., in *Current Protocols in Protein Science,* 1995, Coligan J. E., Dunn B. M., Ploegh H. L., Speicher D. W., Wingfield P. T., ISBN 0-471-11184-8; Bendig, 1988, the entirety of which is incorporated herein by reference. Culturing a cell is done to enable it to metabolize, grow, divide, and/or produce recombinant proteins of interest. This can be accomplished by methods well known to persons skilled in the art and includes, but is not limited to, providing nutrients for the cell. The methods comprise growth adhering to surfaces, growth in suspension, or combinations thereof. Several culturing conditions can be optimized by methods well known in the art to optimize protein production yields. Culturing can be done, for instance, in dishes, roller bottles or in bioreactors, using batch, fed-batch, continuous systems, hollow fiber, and the like. In order to achieve large-scale (continuous) production of recombinant proteins through cell culture, it is preferred in the art to have cells capable of growing in suspension and it is preferred to have cells capable of being cultured in the absence of animal- or human-derived serum or animal- or human-derived serum components. Thus, purification is easier and safety is enhanced due to the absence of additional animal or human proteins derived from the culture medium, while the system is also very reliable as synthetic media are the best in reproducibility.

"Host cells," according to the invention, may be any host cell capable of expressing recombinant DNA molecules, including bacteria such as *Escherichia* (e.g., *E. coli*), *Enterobacter, Salmonella, Bacillus, Pseudomonas, Streptomyces,* yeasts such as *S. cerevisiae, K lactis, P. pastoris, Candida,* or *yarrowia,* filamentous fungi such as *Neurospora, Aspergillus oryzae, Aspergillus nidulans* and *Aspergillus niger,* insect cells such as *Spodoptera frugiperda* SF-9 or SF-21 cells, mammalian cells such as Chinese hamster ovary (CHO) cells, BHK cells, mouse cells including SP2/0 cells and NS-0 myeloma cells, primate cells such as COS and Vero cells, MDCK cells, BRL 3A cells, hybridomas, tumor cells, immortalized primary cells, human cells such as W138, HepG2, HeLa, HEK293, HT1080 or embryonic retina cells such as PER.C6® (human retina cells that express adenovirus E1A and E1B proteins), and the like. Often, the expression system of choice will involve a mammalian cell expression vector and host so that the antibodies are appropriately glycosylated. A human cell line, preferably PER.C6® (human retina cells that express adenovirus E1A and E1B proteins), can advantageously be used to obtain antibodies with a completely human glycosylation pattern. The conditions for growing or multiplying cells (see, e.g., *Tissue Culture,* Academic Press, Kruse and Paterson, editors (1973), the entirety of which is incorporated herein by reference) and the conditions for expression of the recombinant product may differ somewhat and optimization of the process is usually performed to increase the product yields and/or growth of the cells with respect to each other, according to methods generally known to one of ordinary skill in the art.

In general, principles, protocols, and practical techniques for maximizing the productivity of mammalian cell cultures can be found in *Mammalian Cell Biotechnology: a Practical Approach* (M. Butler, ed., IRL Press, 1991), the entirety of which is incorporated herein by reference. Expression of antibodies in recombinant host cells has been extensively described in the art (see, e.g., EP0120694; EP0314161; EP0481790; EP0523949; U.S. Pat. No. 4,816,567; WO 00/63403, the entirety of which are incorporated herein by reference). The nucleic acid molecules encoding the light and heavy chains may be present as extrachromosomal copies and/or stably integrated into the chromosome of the host cell. With regard to stability of production, the latter is preferred.

The antibodies are expressed in the cells according to the invention and may be recovered from the cells or, preferably, from the cell culture medium, by methods generally known to persons skilled in the art. Such methods may include precipitation, centrifugation, filtration, size-exclusion chromatography, affinity chromatography, cation- and/or anion-exchange chromatography, hydrophobic interaction chromatography, and the like. For a mixture of antibodies comprising IgG molecules, protein A- or protein G-affinity chromatography can be suitably used (see, e.g., U.S. Pat. Nos. 4,801,687 and 5,151,504, the entirety of which are incorporated herein by reference).

In one embodiment, at least two antibodies from the mixture produced according to the invention comprise a heavy-light chain dimer having different specificities and/or affinities. The specificity determines which antigen or epitope thereof is bound by the antibody. The affinity is a measure for the strength of binding to a particular antigen or epitope. Specific binding is defined as binding with an affinity ($K_a$) of at least $5\times10^4$ liter/mole, more preferably, $5\times10^5$, even more preferably, $5\times10^6$, and still more preferably, $5\times10^7$, or more. Typically, monoclonal antibodies may have affinities which go up to $10^{10}$ liter per mole or even higher. The mixture of antibodies produced according to the invention may contain at least two antibodies that bind to different epitopes on the same antigen molecule and/or may contain at least two antibodies that bind to different antigen molecules present in one antigen-comprising mixture. Such an antigen-comprising mixture may be a mixture of partially or wholly purified antigens, such as toxins, membrane components and proteins, viral envelope proteins, or it may be a healthy cell, a diseased cell, a mixture of cells, a tissue or mixture of tissues, a tumor, an organ, a complete human or animal subject, a fungus or yeast, a bacteria or bacterial culture, a virus or virus stock, or combinations of these, and the like. Unlike monoclonal antibodies that are able to bind to a single antigen or epitope only, the mixture of antibodies according to the invention may, therefore, have many of the advantages of a polyclonal or oligoclonal antibody mixture.

In a preferred embodiment, the host cell according to the method of the invention is capable of high-level expression of human immunoglobulin, i.e., at least 1 picograms per cell per day, preferably, at least 10 picograms per cell per day and, even more preferably, at least 20 picograms per cell per day or more without the need for amplification of the nucleic acid molecules encoding the heavy and light chains in the host cell.

Preferably, host cells according to the invention contain in their genome between one and ten copies of each recombinant nucleic acid to be expressed. In the art, amplification of the copy number of the nucleic acid sequences encoding a protein of interest in, e.g., CHO cells can be used to increase expression levels of the recombinant protein by the cells (see, e.g., Bendig, 1988; Cockett et al., 1990; U.S. Pat. No. 4,399,216, the entirety of which are incorporated herein by reference). This is currently a widely used method. However, a significant time-consuming effort is required before a clone with a desired high copy number and high expression levels has been established and, moreover, clones harboring very high copy numbers (up to hundreds) of the expression cassette often are unstable (e.g., Kim et al., 1998, the entirety of which is incorporated herein by reference). It is, therefore, a preferred embodiment of the invention to use host cells that do not require such amplification strategies for high-level expression of the antibodies of interest. This allows fast generation of stable clones of host cells that express the mixture of antibodies according to the invention in a consistent manner. We provide evidence that host cells according to the invention can be obtained, sub-cloned and further propagated for at least around 30 cell divisions (population doublings) while expressing the mixture of antibodies according to the invention in a stable manner, in the absence of selection pressure. Therefore, in certain aspects, the methods of the invention include culturing the cells for at least 20, preferably 25, more preferably 30, population doublings and, in other aspects, the host cells according to the invention have undergone at least 20, preferably 25, more preferably 30, population doublings and are still capable of expressing a mixture of antibodies according to the invention. Also provided is a culture of cells producing a mixture of immunoglobulins from a single cell, the mixture comprising at least three different heavy chains. Also provided is a culture of cells producing at least three different monospecific immunoglobulins from a single cell. In certain exemplary aspects, the culture produces the mixture or at least three different monospecific immunoglobulins in a single cell for more than 20, preferably more than 25, more preferably, more than 30 population doublings.

Preferably, host cells according to the method of the invention are derived from human retina cells that have been immortalized or transformed with adenoviral E1 sequences. A particularly preferred host cell according to methods of the invention is PER.C6® (human retina cells that express adenovirus E1A and E1B proteins) as deposited under ECACC no. 96022940, or a derivative thereof. PER.C6-derived clones can be generated fast, usually contain a limited number of copies (about 1-10) of the transgene, and are capable of high-level expression of recombinant antibodies (Jones et al., 2003, the entirety of which is incorporated herein by reference). Therefore, such clones are expected to maintain a stable copy number over many generations, which is an advantage in the production of biopharmaceuticals. PER.C6® (human retina cells that express adenovirus E1A and E1B proteins) cells have been extensively characterized and documented, demonstrating good process of scaling up, suspension growth and growth factor independence. Furthermore, PER.C6® (human retina cells that express adenovirus E1A and E1B proteins) can be incorporated into a suspension in a highly reproducible manner, making it particularly suitable for large-scale production. In this regard, the PER.C6® cell line (human retina cells that express adenovirus E1A and E1B proteins) has been characterized for bioreactor growth, where it can grow to very high densities. The use of PER.C6® (human retina cells that express adenovirus E1A and E1B proteins) for recombinant production of antibodies has been described in detail in publication WO 00/63403 and in (Jones et al., 2003, the entirety of which is incorporated herein by reference).

Also provided is a mixture of antibodies obtainable by a method described herein. Such mixtures of antibodies are expected to be more effective than the sole components it comprises, in analogy to polyclonal antibodies usually being more effective than monoclonal antibodies to the same target. Such mixtures can be prepared against a variety of target antigens or epitopes.

It certain embodiments, the invention provides a recombinant host cell comprising a nucleic acid sequence encoding a light chain and a nucleic acid sequence or nucleic acid sequences encoding at least three different heavy chains of an antibody, wherein the light chain and heavy chains are capable of pairing, preferably to form a functional binding domain. The paired heavy and light chains form functional antigen-binding regions against the target antigen or target antigens. The host cells are useful in the described methods. They can be used to produce mixtures of antibodies.

In certain embodiments, the invention provides a composition comprising a mixture of recombinantly produced antibodies, wherein at least three different heavy chain sequences are represented in the mixture of recombinant antibodies. Monoclonal antibodies are routinely produced by recombinant methods. Also disclosed are mixtures of antibodies useful for diagnosis or treatment in various fields. In certain embodiments, the compositions of the invention comprise mixtures of at least three different heavy chains paired to light chains in the form of antibodies. Preferably, the light chains of the antibodies in the mixtures have a common light chain. The mixtures may comprise bispecific antibodies. The mixtures may be produced from a clone that was derived from a single host cell, e.g., from a population of cells containing the same recombinant nucleic acid sequences. The mixtures can be obtained by methods according to the invention or be produced by host cells according to the invention. In other embodiments, the number of heavy chains represented in the mixture is 4, 5, 6, 7, 8, 9, 10, or more. The optimal mixture for a certain purpose may be determined empirically by methods known to one of ordinary skill in the art or by methods provided by the invention. Such compositions according to the invention may have several of the advantages of a polyclonal antibody mixture, without the disadvantages usually inherently associated with polyclonal antibody mixtures, because of the manner in which they are produced. It is furthermore expected that the mixture of antibodies is more efficacious than separate monoclonal antibodies. Therefore, the dosage and, hence, the production capacity required may be less for the mixtures of antibodies according to the invention than for monoclonal antibodies.

It has, for instance, been described that although no single monoclonal antibody to botulinum neurotoxin (BoNTIA) significantly neutralized toxin, a combination of three such monoclonal antibodies (oligoclonal antibody) neutralized 450,000 50% lethal doses of BoNTIA, a potency 90 times greater than human hyperimmune globulin (Nowakowski et al., 2002, the entirety of which is incorporated herein by reference). This result demonstrates that oligoclonal mixtures of antibodies comprising only two to three different specificities may have very high potency.

Furthermore, the chances of a mixture of the invention losing its activity due to target or epitope loss is reduced, when compared to a single monoclonal antibody. In particular embodiments, 2, 3, 4, 5, 6, 7, 8, 9, 10, or more of the antibodies present in the mixture according to the invention have different specificities. Different specificities may be directed to different epitopes on the same antigen and/or may be directed to different antigens present in one antigen-comprising mixture. A composition according to the invention may also further comprise 2, 3, 4, 5, 6, 7, 8, 9, 10, or more antibodies having different affinities for the same epitope. Antibodies with differing affinities for the same epitope may, for instance, be generated by methods of affinity maturation known to one of ordinary skill in the art.

In a particularly preferred embodiment, the composition according to the invention has an effect that is greater than the effect of each individual monospecific antibody present in the composition. The effect can be measured in a functional assay. A "functional assay," as used herein, is an assay that can be used to determine one or more desired parameters of the antibody or the mixture of antibodies subject to the assay conditions. Suitable functional assays may be binding assays, apoptosis assays, antibody-dependent cellular cytotoxicity (ADCC) assays, complement-dependent cytotoxicity (CDC) assays, inhibition of cell growth or proliferation (cytostatic effect) assays, cell-killing (cytotoxic effect) assays, cell-signaling assays, assays for measuring inhibition of binding of pathogen to target cell, assays to measure the secretion of vascular endothelial growth factor (VEGF) or other secreted molecules, assays for bacteriostasis, bactericidal activity, neutralization of viruses, assays to measure the attraction of components of the immune system to the site where antibodies are bound, including in situ hybridization methods, labeling methods, and the like. Clearly, also in vivo assays, such as animal models, including mouse tumor models, models of auto-immune disease, virus-infected or bacteria-infected rodent or primate models, and the like, can be used for this purpose. The efficacy of a mixture of antibodies according to the invention can be compared to individual antibodies in such models by methods generally known to one of ordinary skill in the art.

In certain embodiments, the invention provides a method for identifying at least one host cell clone that produces a mixture of antibodies, wherein the mixture of antibodies has a desired effect according to a functional assay, the method comprising (i) providing a host cell comprising a nucleic acid sequence encoding at least one light chain and nucleic acid sequence or sequences encoding at least two different heavy chains, wherein the heavy and light chains are capable of pairing with each other; (ii) culturing at least one clone of the host cell under conditions conducive to expression of nucleic acid sequences; (iii) screening at least one clone of the host cell for production of a mixture of antibodies having the desired effect by a functional assay; and (iv) identifying at least one clone that produces a mixture of antibodies having the desired effect. Preferably, the host cell comprises a nucleic acid sequence encoding a common light chain that is capable of pairing with at least two different heavy chains, such that produced antibodies comprise common light chains, as described above. In specific embodiments, culturing in step (ii) and screening in step (iii) of the method is performed with at least two clones. The method may optionally include an assay for measuring the expression levels of the antibodies that are produced, which assay may be during or after step (ii) according to the method, or later in the procedure. Such assays are well known to one of ordinary skill in the art and include protein concentration assays, immunoglobulin-specific assays such as ELISA, RIA, DELFIA, and the like. In particular embodiments of the method according to the invention, the host cell comprises nucleic acid sequence or sequences encoding at least 3, 4, 5, 6, 7, 8, 9, 10, or more, heavy chains capable of pairing with at least one light chain. Functional assays useful for the method according to the invention may be assays for apoptosis, ADCC, CDC, cell killing, inhibition of proliferation, virus neutralization, bacterial opsonization, receptor-mediated signaling, cell signaling, bactericidal activity, and the like. Useful screening assays for anti-cancer antibodies have, for instance, been described in U.S. Pat. No. 6,180,357, the entirety of which is incorporated herein by reference. Such assays may also be used to identify a clone according to the method of the invention. It is, for instance, possible to use enzyme-linked immunosorbent assays (ELISAs) for the testing of antibody binding to their target. Using such assays, it is possible to screen for antibody mixtures that most avidly bind the target antigen (or mixture of target antigens against which the mixture of antibodies is to be tested). Another possibility that can be explored is to directly screen for cytotoxicity or cytostatic effects. It is possible that upon such a different screen, other or the same clones producing mixtures of antibodies will be chosen than with the ELISA mentioned above. The screening for cell killing or cessation of growth of cancerous cells may be suitably used according to the invention. Cell death can be measured by various endpoints, including the absence of metabolism or the denaturation of enzymes. In one possible embodiment of the invention, the assay is conducted by focusing on cytotoxic activity toward cancerous cells as an endpoint. For this assay, a live/dead assay kit, for example, the LIVE/DEAD® Viability/Cytotoxicity Assay Kit (L-3224) by Molecular Probes (Eugene, Oreg.), can suitably be used. Other methods of assessing cell viability, such as tryspan blue exclusion, $^{51}$Cr release, Calcein-AM, ALAMAR BLUE™, LDH activity, and similar methods, can also be used. The assays may also include screening of the mixture of antibodies for specificity to the desired antigen-comprising tissue. The antibodies according to the invention may have a limited tissue distribution. It is possible to include testing the mixtures of antibodies against a variety of cells, cell types, or tissues, to screen for mixtures of antibodies that preferably bind to cells, cell types or tissues of interest.

Irrespective of a functional assay as described above, also disclosed herein are ways to determine the identity of the antibodies expressed by a clone, using methods such as isoelectric focusing (IEF), mass-spectrometry (MS), and the like. In certain embodiments, therefore, the invention provides use of MS and/or IEF in selecting a clone that expresses a mixture of antibodies according to the invention.

When monoclonal antibodies are produced by recombinant host cells, a screening step is usually performed to assess expression levels of the individual clones that were generated. The addition of more heavy chains to produce mixtures adds a level of complexity to the production of antibodies. When host cells are transfected with nucleic acid molecules encoding the light and heavy chains that will form the mixture of antibodies desired, independent clones may arise containing the same genetic information but, nevertheless, differing in expression levels, thereby producing different ratios of the encoded antibodies, giving rise to different mixtures of antibodies from the same genetic repertoire. The method according to the invention is useful for identifying a clone that produces an optimal mixture for a certain purpose.

The culturing and/or screening according to steps (ii) and (iii), respectively, may be suitably performed using high-throughput procedures, optionally in an automated fashion. Clones can, for instance, be cultured in 96-well plates or other multi-well plates, e.g., in arrayed format, and screened for production of a desired mixture. Robotics may be suitably employed for this purpose. Methods to implement high-throughput culturing and assays are generally available and known to one of ordinary skill in the art. It will also be clear that for this method according to the invention, it is beneficial to use host cells capable of high-level expression of proteins, without the need for amplification of the nucleic acid encoding the proteins in the cell. In one embodiment, the host cell is derived from a human embryonic retinoblast cell that has been immortalized or transformed by adenoviral E1 sequences. In a preferred embodiment, the cell is derived from PER.C6® (human retina cells that express adenovirus E1A and E1B proteins). This cell line has already been shown to be amenable to high-throughput manipulations, including culturing (WO 99/64582, the entirety of which is incorporated herein by reference).

In specific embodiments of the invention, the mixture of antibodies according to the method of identifying at least one host cell according to the invention, comprises at least 2, 3, 4, 5, 6, 7, 8, 9, 10, or more, antibodies having different specificities and/or affinities.

A potential advantage of the method will be that it will allow exploring many possible combinations simultaneously, the combinations inherently including the presence of bispecific antibodies in the produced mixture. Therefore, more combinations can be tested than by just mixing purified known monoclonal antibodies, both in number of combinations and in ratios of presence of different antibodies in these combinations.

The clone that has been identified by the method according to the invention can be used for producing a desired mixture of antibodies. In certain embodiments, the invention provides a method of producing a mixture of antibodies, the method comprising culturing a host cell clone identified by the method of identifying at least one host cell clone that produces a mixture of antibodies according to the invention, culturing being under conditions conducive to expression of the nucleic acid molecules encoding at least one light chain and at least two different heavy chains. The produced antibodies may be recovered from the host cells and/or from the host cell culture, for example, from the culture medium. The mixture of antibodies can be recovered according to a variety of techniques known to one of ordinary skill in the art.

In certain embodiments, the invention provides a mixture of antibodies obtainable by the method according to the invention described above. The mixtures can be used for a variety of purposes, such as in the treatment or diagnosis of disease, and may replace, or be used in addition to, monoclonal or polyclonal antibodies.

The methods according to the invention may suitably use nucleic acid molecules for encoding the antibodies, which nucleic acid molecules have been obtained by any suitable method, including in vivo, e.g., immunization, methods or in vitro, for instance, antibody display methods (A. Plückthun et al., In vitro selection and evolution of proteins, in *Adv. Prot. Chem.*, F. M. Richards et al., Eds, Academic Press, San Diego, 2001, vol. 55:367-403, the entirety of which is incorporated herein by reference), such as phage display, ribosome display or mRNA display (C. Schaffitzel et al., In vitro selection and evolution of protein-ligand interactions by ribosome display, in *Protein-Protein Interactions, A Molecular Cloning Manual*, E. Golemis, Ed., Cold Spring Harbor Laboratory Press, New York, 2001, pp. 535-567, the entirety of which is incorporated herein by reference), and yeast display (e.g., WO 99/36569, the entirety of which is incorporated herein by reference). Methods of identifying antibodies to a certain target, which target may be a known antigen or an unknown antigen present in an antigenic mixture, by phage display are known to one of ordinary skill in the art. In general, a library of phages that express an antigen-binding domain or derivative thereof on their surface, the antigen-binding domain encoded by genetic material present in the phages, is incubated with the antigen or antigen mixture of interest, after which binding of a sub-population of the phages that display antigen-binding sites binding to the desired antigen is obtained whereas the non-binding phages are discarded. Such selection steps may be repeated one, two, or more times to obtain a population of phages that are more or less specific for the antigen of interest. Phage display methods to obtain antibodies, parts or derivatives thereof have been extensively described in C. F. Barbas III et al., *Phage Display, A laboratory manual*, Cold Spring Harbor Laboratory Press, Cold Spring Harbor, N.Y., 2001, the entirety of which is incorporated herein by reference. The library used for such screening may be generated by using the genetic information of one or more light chains, combined with genetic information encoding a plurality of heavy chains. The library described by De Kruif et al. (1995b), the entirety of which is incorporated herein by reference, comprises seven light chains, the entirety of which is incorporated herein by reference. Therefore, in a panel of phages binding to a target, which can, e.g., be obtained by methods described in De Kruif et al. (supra), and U.S. Pat. No. 6,265,150 (the entirety of which is incorporated herein by reference), not more than seven different light chains will be represented and, if the panel is large enough, several phages with the same light chain coupled to unrelated heavy chains may be found. Such phages can be used to obtain the nucleic acid molecules useful in the methods according to the invention.

In certain embodiments, the invention provides a method for producing a mixture of antibodies to a target, the method comprising i) bringing an antibody display library comprising antibodies or antibody fragments into contact with material comprising a target, ii) at least one step of selecting antibodies or antibody fragments binding to the target, iii) identifying at least two antibodies or antibody fragments binding to the target, wherein at least two antibodies or antibody fragments comprise a common light chain, iv) introducing a nucleic acid sequence encoding the light chain and a nucleic acid sequence or nucleic acid sequences encoding the heavy chains of at least two antibodies into a host cell, v) culturing a clone of the host cell under conditions conducive to expression of nucleic acid sequences. The antibody display library may be a phage display library, a ribosome display library, an mRNA display library, or a yeast display library. Steps i) and ii) may optionally be repeated one or more times.

The nucleic acid sequences encoding the antibodies obtained by the phage display, ribosome display or yeast display method may be converted to encode any desired antibody format such as IgG1, IgG2, IgG3, IgG4, IgA, IgM, IgD, IgE, before introducing them into a host cell, using standard molecular cloning methods and means known to one of ordinary skill in the art (e.g., described in Boel et al., 2000, the entirety of which is incorporated herein by reference).

It will be clear to one of ordinary skill in the art that libraries in which only one light chain is represented are especially useful in light of the invention, since all antibodies that can be obtained from such a library will have a common light chain that is functional in binding target antigen with each of the heavy chains. In other words, in accordance with the methods of the invention, the formation of non-functional light chain-heavy chain dimers is avoided. Phage antibody display libraries having extensive H chain repertoires and unique or very few L chain sequences have been disclosed in the art (Nissim et al., 1994; Vaughan et al., 1996, the entirety of which are incorporated herein by reference). In general, the specificity of an antibody appears to be determined to a large extent by its heavy chain. It is even possible to screen for and identify light chains that do not contribute significantly to binding of the antibody, which light chains also could be suitably used according to the invention. It may also be possible to follow the teachings of the invention but use one heavy chain and vary the light chains. However, the use of a common light chain and different heavy chains appears preferable and the following observations support the idea that the specificity of an antibody appears to be dominated by its heavy chain sequence. In the process of receptor editing, a mechanism of B-cells to monitor if their immunoglobulin receptor encodes a potentially harmful auto-antibody, B-cells expressing an auto-antibody replace the expressed heavy chain with another heavy chain while retaining the expressed light chain. Thus, a new antibody specificity is generated that does not encode an auto-antibody. This shows that a single light chain can successfully dimerize with multiple heavy chains to form different antibody specificities (Nemazee, 2000; Casellas et al., 2001, the entirety of which are incorporated herein by reference). Series of transfected cell lines using a single heavy chain gene with different light chain genes have been reported, the antibodies produced to a large extent maintaining their specificity, regardless of the light chain (Radic et al., 1991, the entirety of which is incorporated herein by reference).

Different antibodies have been obtained from a library that has been constructed using a single light chain (Nissim et al., 1994). Several antibodies have been obtained from the library described by De Kruif et al. (1995, the entirety of which is incorporated herein by reference), which was constructed using seven light chains, that have the same light chain but different specificities (see, e.g., Example 1: antibodies binding to EpCAM and to CD46, described in WO 01/48485 and WO 02/18948, respectively, the entirety of which are incorporated herein by reference).

Besides screening a phage library against a target, it will also be possible to start with an antibody that has already proven its merits and use the light chain of this antibody in the preparation of a library of heavy chains combined with this particular light chain only, according to methods known to one of ordinary skill in the art, such as phage display. Using this strategy, a monoclonal antibody can be used to obtain a mixture of antibodies according to the invention, functionally resembling a polyclonal or oligoclonal antibody to the same target. Alternatively, a method reminiscent of the method described by Jespers et al. (1994, the entirety of which is incorporated herein by reference) to obtain a human antibody based on a functional rodent antibody can be used. The heavy chain of a known antibody of non-human origin is first cloned and paired as a template chain with a repertoire of human light chains for use in phage display, after which the phages are selected for binding to the antigen or mixture of antigens. The selected light chain is, in turn, paired with a repertoire of human heavy chains displayed on a phage and the phages are selected again to find several heavy chains that, when paired with the light chain, are able to bind to the antigen or mixture of antigens of interest. This enables creating a mixture of human antibodies against a target for which thus far only a non-human monoclonal antibody is described. It is possible that a mixture according to the invention already has beneficial functional effects when the individual antibodies do not have high affinities for the target, whereas high affinities are often required for monoclonal antibodies to be effective. This would have the advantage that affinity maturation may be required in less instances for methods and mixtures according to the invention than when an approach with monoclonal antibodies is envisaged.

The heavy and light chain coding sequences can be introduced simultaneously or consecutively into the host cell. It is also an aspect of the invention to prepare a host cell comprising a recombinant nucleic acid encoding a light chain of an antibody. Such a cell can, for instance, be obtained by transfection of the nucleic acid and, optionally, a clone can be identified that has a high expression of the light chain. An established clone may then be used to add genetic information encoding 2, 3, 4, 5, 6, 7, 8, 9, 10, or more, heavy chains of the invention by introducing the nucleic acid molecules encoding these into cells of the clone that already contains the light chain. The nucleic acid molecules encoding the heavy chains may be introduced into the host cell concomitantly. It is, of course, also possible to introduce them consecutively, for instance, by using different selection markers, which can be advantageous if not all heavy chains can be introduced simultaneously because the cells do not take up enough copies of recombinant nucleic acid molecules. Methods to introduce recombinant nucleic acid molecules into host cells are well known to one of ordinary skill in the art and include transfection, electroporation, calcium phosphate precipitation, virus infection, and the like. One of ordinary skill in the art has several possibilities to introduce more vectors with nucleic acid sequences of interest into the same host cell, see, e.g., Sambrook, Fritsch and Maniatis, *Molecular Cloning: A Laboratory Manual*, $2^{nd}$ edition, 1989; *Current Protocols in Molecular Biology*, Ausubel F. M., et al., eds, 1987; the series *Methods in Enzymology* (Academic Press, Inc.), the entirety of which are incorporated herein by reference.

Suitable dominant selection markers for introducing nucleic acids into eukaryotic host cells, as used herein, may be G418 or neomycin (geneticin), hygromycin or mycophenolic acid, puromycin, and the like, for which genes encoding resistance are available on expression vectors. Further possibilities include, for instance, the use of vectors containing DHFR genes or glutamate synthetase to select in the presence of methotrexate in a DHFR cell or the absence of glutamine in a glutamine auxotroph, respectively. The use of expression vectors with different selection markers enables subsequent transfections with heavy chain sequences of interest into the host cell, which already stably contains other heavy chains introduced previously by use of other selection markers. It is also possible to use selection markers that can be used more than once, for instance, when containing mutations, introns, or weakened promoters that render them concentration-dependent (e.g., EP0724639; WO 01/32901; U.S. Pat. No. 5,733,779, the entirety of which are incorporated herein by reference). Alternatively, a selection marker may be re-used by deleting it from the host cell after use, for example, by site-specific recombination. A selectable marker located between sequences recognized by a site-specific recombinase, for example, lox-sites or FRT-sites, is used for the generation of the first stable transfectant (for Cre-lox site-specific recombination, see, Wilson and Kola, 2001, the entirety of which is incorporated herein by reference). Subsequently, the selectable marker is excised from the host cell DNA by the matching site-specific recombinase, for example, Cre or Flp. A subsequent transfection can suitably use the same selection marker.

Different host cell clones each comprising the genetic information encoding a different light chain may be prepared. If the antibodies are identified by an antibody display method, it is thus possible to prepare several host cells, each comprising one light chain present in the antibody display library. After identifying antibodies that bind to a target using antibody display, the nucleic acid molecules encoding the heavy chains can be introduced into the host cell containing the common light chain that is capable of pairing to the heavy chains. It is, therefore, an aspect of the invention to provide a method for making a host cell for production of a mixture of antibodies, the method comprising the steps of: introducing into the host cell a nucleic acid sequence encoding a light chain and nucleic acid sequence or sequences encoding 3, 4, 5, 6, 7, 8, 9, 10, or more, different heavy chains that are capable of pairing with the light chain, wherein the nucleic acid molecules are introduced consecutively or simultaneously. It is, of course, also possible to introduce at least two of the nucleic acid molecules simultaneously, and introduce at least one other of the nucleic acid molecules consecutively.

In yet another aspect of the invention, a method is provided for making a recombinant host cell for production of a mixture of antibodies, the method comprising the step of: introducing a nucleic acid sequence or nucleic acid sequences encoding 2, 3, 4, 5, 6, 7, 8, 9, 10, or more, different heavy chains into a recombinant host cell comprising a nucleic acid sequence encoding a light chain capable of pairing with at least two of the heavy chains.

If it appears that a recombinant host cell of the invention does not express sufficient light chain to dimerize with all of the expressed at least two heavy chains, extra copies of the nucleic acid molecules encoding the light chain may be transfected into the cell.

Besides random integration after transfection, methods to integrate the transgenes in predetermined positions of the genome resulting in favorable expression levels can also be used according to the invention. Such methods may, for instance, employ site-specific integration by homologous recombination (see, e.g., WO 98/41645, the entirety of which is incorporated herein by reference) or make use of site-specific recombinases (Gorman and Bullock, 2000, the entirety of which is incorporated herein by reference).

It is yet another aspect of the invention to provide a transgenic non-human mammal or a transgenic plant comprising a nucleic acid sequence encoding a light chain and a nucleic acid sequence or nucleic acid sequences encoding at least two different heavy chains that are capable of pairing with the light chain, wherein the nucleic acid sequences encoding the light and heavy chains are under the control of a tissue-specific promoter. Promoters in plants may also be non-tissue specific and general gene-expression elements, such as the CaMV 35S promoter and nopaline synthase polyA addition site, can also be used. The light chain is a common light chain according to the invention. In specific embodiments, the transgenic animal or plant according to the invention comprises 3, 4, 5, 6, 7, 8, 9, 10, or more, heavy chain sequences. Besides cell culture as a production system for recombinant proteins, the art also discloses the use of transgenic animals, transgenic plants and, for instance, transgenic chickens to produce proteins in the eggs, and the like to produce recombinant proteins of interest (Pollock et al., 1999; Larrick and Thomas, 2001; WO 91/08216, the entirety of which are incorporated herein by reference). These usually comprise the recombinant gene or genes encoding one or more proteins of interest in operable association with a tissue-specific promoter. It has, for instance, been shown that recombinant antibodies can be produced at high levels in the milk of transgenic animals that contain the nucleic acids encoding a heavy and a light chain behind a mammary gland-specific promoter (e.g., Pollock et al., 1999; WO 95/17085, the entirety of which are incorporated herein by reference). Particularly useful in this respect are cows, sheep, goats, pigs, rabbits, mice, and the like, which can be milked to obtain antibodies. Useful promoters are the casein promoters, such as the β-casein promoter, the αS1-casein promoter, the whey acidic protein (WAP) promoter, the β-lactoglobulin promoter, the α-lactalbumin promoter, and the like. Production of biopharmaceutical proteins in the milk of transgenic mammals has been extensively described (e.g., Pollock et al., 1999, the entirety of which is incorporated herein by reference). Besides mammary gland-specific promoters, other tissue-specific promoters may be used, directing the expression to the blood, urine, saliva, and the like. The generation of transgenic animals comprising recombinant nucleic acid molecules has been extensively documented and may include micro-injection of oocytes (see, e.g., Wilmut and Clark, 1991, the entirety of which is incorporated herein by reference), nuclear transfer after transfection (e.g., Schnieke et al., 1997, the entirety of which is incorporated herein by reference), infection by recombinant viruses (e.g., U.S. Pat. No. 6,291,740, the entirety of which is incorporated herein by reference), and the like. Nuclear transfer and cloning methods for mammalian cells are known to one of ordinary skill in the art, and are, for example, described in Campbell et al., 1996; Wilmut et al., 1997; Dinnyes et al., 2002; WO 95/17500; and WO 98/39416, the entirety of which are incorporated herein by reference. It is possible to clone animals and to generate lines of animals that are genetically identical, which renders it possible for a person skilled in the art to create such a line once an individual animal producing the desired mixture of antibodies has been identified. Alternatively, classical breeding methods can be used to generate transgenic offspring. Strategies for the generation of transgenic animals for production of recombinant proteins in milk are described in Brink et al., 2000, the entirety of which is incorporated herein by reference.

Transgenic plants or plant cells producing antibodies have also been described (Hiatt et al., 1989; Peeters et al., 2001, the entirety of which are incorporated herein by reference) and useful plants for this purpose include corn, maize, tobacco, soybean, alfalfa, rice, and the like. Constitutive promoters that can, for instance, be used in plant cells are the CaMV 35S and 19S promoters and *Agrobacterium* promoters nos and ocs. Other useful promoters are light-inducible promoters such as rbcS. Tissue-specific promoters can, for instance, be seed-specific, such as promoters from zein, napin, beta-phaseolin, ubiquitin, or tuber-specific, leaf-specific (e.g., useful in tobacco), root-specific, and the like. It is also possible to transform the plastid organelle by homologous recombination to express proteins in plants.

Methods and means for expression of proteins in recombinant plants or parts thereof, or recombinant plant cell culture, are known to one of ordinary skill in the art and have been, for instance, described in Giddings et al., 2000; WO 01/64929; WO 97/42313; U.S. Pat. Nos. 5,888,789, 6,080,560 (for practical guidelines, see *Methods In Molecular Biology* vol. 49 "Plant Gene Transfer And Expression Protocols," H. Jones, 1995), the entirety of which are incorporated herein by reference. Other transgenic systems for producing recombinant proteins have also been described, including the use of transgenic birds to produce recombinant proteins in eggs (e.g., WO 97/47739, the entirety of which is incorporated herein by reference) and the use of transgenic fish (e.g., WO 98/15627, the entirety of which is incorporated herein by reference), and can be used in combination with the teachings of the invention to obtain mixtures of antibodies. It is also possible to use an in vitro transcription/translation or in vitro translation system for the expression of mixtures of antibodies according to the invention. It will be clear to one of ordinary skill in the art that the teachings of the current invention will allow producing mixtures of antibodies in systems where recombinant nucleic acids encoding the light chain and heavy chains can be introduced and expressed. Preferably, such systems are able to produce antibodies encoded by nucleic acid sequences, without the use of amplification of nucleic acid sequences in the systems. In another aspect of the invention, a cell from a transgenic non-human animal or a transgenic plant according to the invention is provided. Such cells can be used to generate the animals or plants according to the invention, using techniques known to one of ordinary skill in the art, such as nuclear transfer or other known methods of cloning whole organisms from single cells. The cells according to the invention may also be obtained by introducing the light and at least two heavy chain sequences into isolated cells of non-human animals or plants, which cells are capable of becoming part of a transgenic animal or plant. Particularly useful for such purposes are embryonic stem cells. These can contribute to the germ line and, therefore, the genetic information introduced into such cells can be passed to future generations. In addition, plant cell cultures of cotton, corn, tomato, soybean, potato, petunia, and tobacco can be utilized as hosts when transformed with the nucleic acid molecules encoding the light chain and the heavy chains, for instance, by use of the plant-transforming bacterium *A. tumefaciens* or by particle bombardment or by infecting with recombinant plant viruses.

In certain embodiments, the invention provides a pharmaceutical composition comprising a mixture of recombinantly produced antibodies and a suitable carrier, wherein at least two different heavy chains are represented in the mixture of recombinantly produced antibodies. Pharmaceutically acceptable carriers as used herein are exemplified, but not limited to, adjuvants, solid carriers, water, buffers, or other carriers used in the art to hold therapeutic components, or combinations thereof. In particular embodiments, 3, 4, 5, 6, 7, 8, 9, 10, or more, different heavy chains are represented in the mixture. The mixture can be obtained by mixing recombinantly produced monoclonal antibodies, but may also be obtained by methods according to the invention. The mixture may, therefore, comprise a common light chain for the antibodies. The mixture may comprise bispecific antibodies. The mixture may be produced from a clone that was derived from a single host cell, e.g., from a population of cells containing the same recombinant nucleic acid molecules. The term "recombinantly produced" as used herein refers to production by host cells that produce antibodies encoded by recombinant nucleic acids introduced in such host cells or ancestors thereof. It does not, therefore, include the classical method of producing polyclonal antibodies, whereby a subject is immunized with an antigen or antigen-comprising mixture, after which the antibodies produced by this subject are recovered from the subject, for example, from the blood.

In certain embodiments, the invention provides a mixture of antibodies wherein at least two heavy chains are represented for use in the treatment or diagnosis of a human or animal subject. In another aspect, the invention provides the use of a mixture of antibodies wherein at least two different heavy chains are represented for the preparation of a medicament for use in the treatment or diagnosis of a disease or disorder in a human or animal subject. In particular embodiments, 2, 3, 4, 5, 6, 7, 8, 9, 10, or more, heavy chains are represented in the mixture. The mixtures of antibodies may be mixtures of antibodies according to the invention or obtained by methods according to the invention. Antibodies present in the mixture may preferably comprise a common light chain. The mixtures may comprise bispecific antibodies and may be recombinantly produced from a clone that was derived from a single host cell, i.e., from a population of cells containing the same recombinant nucleic acid molecules. The targets may be used to screen an antibody display library, as described supra, to obtain 2, 3, 4, 5, 6, 7, 8, 9, 10, or more, antibodies comprising a common light chain that bind to the target and produce a mixture of these according to the teachings of the invention. Virtually any area of medicine where monoclonal antibodies can be used is amenable for the use of the mixtures according to the invention. This can, e.g., include treatment of auto-immune diseases and cancer, including solid tumors of the brain, head, neck, breast, prostate, colon, lung, and the like, as well as hematologic tumors, such as B-cell tumors. Neoplastic disorders which can be treated with the mixtures according to the invention include leukemias, lymphomas, sarcomas, carcinomas, neural cell tumors, squamous cell carcinomas, germ cell tumors, metastases, undifferentiated tumors, seminomas, melanomas, myelomas, neuroblastomas, mixed cell tumors, neoplasias caused by infectious agents, and other malignancies. Targets for the antibody mixtures may include, but are not limited to, the HER-2/Neu receptor, other growth factor receptors (such as VEGFR1 and VEGFR2 receptors), B-cell markers (such as CD19, CD20, CD22, CD37, CD72, etc.), T-cell markers (such as CD3, CD25, etc.), other leukocyte cell surface markers (such as CD33 or HLA-DR, etc.), cytokines (such as TNF), interleukins, receptors for these cytokines (such as members of the TNF receptor family), and the like. It is anticipated that the use of such mixtures of antibodies in the treatment of cancerous tissues or other complex multi-antigen-comprising cells such as microorganisms or viruses will give rise to less occurrence of epitope-loss escape variants than the use of single monoclonal antibodies. Several treatments nowadays use polyclonal mixtures of antibodies, which are derived from immunized humans or animals. These treatments may be replaced by use of the mixtures according to the invention. Use of these mixtures can also include use in graft-versus-host rejections known in the art of transplantation, e.g., by use of anti-thymocyte antibodies. It is anticipated that the mixtures of antibodies are superior to monoclonal antibodies in the treatment of complex antigens or antigen-comprising mixtures such as bacteria or viruses. Therefore, use according to the invention can also include use against strains of bacteria and fungi, e.g., in the treatment of infectious diseases due to pathogenic bacteria such as multidrug-resistant *S. aureus* and the like, fungi such as *Candida albicans* and *Aspergillus* species, yeast and the like. The mixtures according to the invention may also be used for post exposure prophylaxis against viruses, such as members of the genus *Lyssavirus*, e.g., rabies virus, or for therapeutic or prophylactic use against viruses such as *Varicella-Zoster* Virus, Adenoviruses, Respiratory Syncitium Virus, Human Immunodeficiency Virus, Human Metapneumovirus, Influenzavirus, West Nile Virus, the virus causing Severe Acute Respiratory Syndrome (SARS), and the like. Mixtures according to the inventions can also be used to protect against agents, both bacteria and viruses, and against toxic substances that are potential threats of biological warfare. Therefore, use according to the invention can also include use against strains of bacteria such as *Bacillus anthracis, Clostridium botulinum toxin, Clostridium perfringens* epsilon toxin *Yersinia Pestis, Francisella tular-*

*iensis, Coxiella burnetii, Brucella* species, *Staphylococcus* enterotoxin B, or against viruses such as Variola major, alphaviruses causing meningoencephalitis syndromes (EEEV, VEEV, and WEEV), viruses known to cause hemorrhagic fevers such as Ebola, Marburg and Junin virus or against viruses such as Nipah virus, Hantaviruses, Tickborne encephalitis virus and Yellow fever virus or against toxins, for example, Ricin toxin from *Ricinus communis* and the like. Use of the mixtures according to the invention can also include use against unicellular or multicellular parasites. Recombinant mixtures of antibodies according to the invention may become a safe alternative to polyclonal antibodies obtained from pools of human sera for passive immunization or from sera of hyper-immunized animals. The mixtures may be more efficacious than recombinant monoclonal antibodies in various therapeutic applications, including cancer, allergy, viral diseases, chronic inflammation, and the like.

It has been described that homodimerization of tumor-reactive monoclonal antibodies markedly increases their ability to induce growth arrest or apoptosis of tumor cells (Ghetie et al., 1997, the entirety of which is incorporated herein by reference). Possibly, when antibodies against receptors or other surface antigens on target cells, such as tumor cells or infectious microorganisms, are produced according to the invention, the bispecific antibodies present in mixtures according to the invention may also cross-link different receptors or other antigens on the surface of target cells and, therefore, such mixtures may be very suitable for killing such cells. Alternatively, when bispecific antibodies are less desirable, the invention also provides methods to recombinantly produce mixtures of antibodies comprising mainly monospecific antibodies. It has been described that the efficacy of treatment with Rituximab™ (anti-CD20 monoclonal antibody) was increased when anti-CD59 antibodies were added (Herjunpaa et al., 2000, the entirety of which is incorporated herein by reference).

Therefore, it is expected that inclusion of antibodies against CD59 in a mixture according to the invention comprising anti-tumor antibodies in the form of B-cell receptor-recognizing antibodies increases the sensitivity of tumor cells to complement attack. It has also been shown that a triple combination cocktail of anti-CD19, anti-CD22, and anti-CD38-saporin immunotoxins is much more effective than the individual components in the treatment of human B-cell lymphoma in an immunodeficient mouse model (Flavell et al., 1997, the entirety of which is incorporated herein by reference). Many other combinations may also be feasible and can be designed by one of ordinary skill in the art. In general, the use of antibody mixtures that are capable of recognizing multiple B-cell epitopes will likely decrease the occurrence of escape variants.

Another possible target is a transmembrane tyrosine kinase receptor, encoded by the Her-2/Neu (ErbB2) proto-oncogene (see, e.g., U.S. Pat. Nos. 5,772,997 and 5,783,186 for anti-Her2 antibodies, the entirety of which are incorporated herein by reference). Her-2 is overexpressed on 30% of highly malignant breast cancers and successful antibodies against this target marketed under the name HERCEPTIN™ (Trastuzumab) have been developed. It has been shown that targeting multiple Her-2 epitopes with a mixture of monoclonal antibodies results in improved antigrowth activity of a human breast cancer cell line in vitro and in vivo (Spiridon et al., 2002, the entirety of which is incorporated herein by reference). Her-2 may, therefore, be a good target for antibody mixtures according to the invention. Antibodies useful for this purpose can be obtained by methods described in the invention, including antibody display methods.

Human antibodies are capable of eliciting effector function via binding to immunoglobulin receptors on immune effector cells. Human IgG and, in particular, IgG1 and IgG3, fix complement to induce CDC and interact with Fcγ receptors to induce antibody-dependent cell-mediated cytotoxicity (ADCC), phagocytosis, endocytosis, induction of respiratory burst and release of inflammatory mediators and cytokines. Human IgA interacts with FcαR, also resulting in efficient activation of ADCC and phagocytosis of target cells. Hence, due to the differential distribution of FcγR and FcαR on peripheral blood cells (Huls et al., 1999, the entirety of which is incorporated herein by reference), using a mixture of antibodies directed against the target and consisting of both IgG and IgA would potentially maximize the recruitment and activation of different immune effector cells. Such a mixture of both IgG and IgA could be obtained by producing the IgG and IgA monoclonal antibody in a separate production process using two distinct production cell lines, but could also be obtained from a single cell line producing both the IgG and the IgA monoclonal antibody. This would have the advantage that only a single production process has to be developed. Thus, when different heavy chains are mentioned, heavy chains differing in their constant regions are also encompassed in the invention. The principle of using a common light chain can also be used for the production of a mixture of isotypes from a host cell. Therefore, certain embodiments of the invention provide a method for producing a mixture of antibodies comprising different isotypes from a host cell, the method comprising the step of: culturing a host cell comprising a nucleic acid sequence encoding a light chain and nucleic acid sequences encoding at least two heavy chains of different isotype that are capable of pairing with the light chain, under conditions conducive to expression of the nucleic acid sequences. According to this aspect of the invention, different heavy chains may have identical variable regions and only differ in their constant regions (i.e., be of different isotype and have the same specificity). In a particular embodiment, the isotypes comprise at least an IgG and an IgA and/or IgM, preferably IgG1 or IgG3 and IgA. Other combinations of IgG1, IgG2, IgG3 and IgG4 can also be used. In these embodiments, bispecific antibodies will not be produced because the variable regions are the same.

In other embodiments of this aspect of the invention, not only the constant regions of the heavy chains may differ, but also the variable regions, thereby giving rise to different specificities paired with the same light chain. When bispecific antibodies are not desired for a given purpose, for example, because the mixtures of antibodies are less efficacious because of the presence of the bispecific antibodies, it is possible to use at least two heavy chains combined with the common light chain according to the invention wherein the heavy chains differ sufficient in their constant regions to reduce or prevent pairing between the different heavy chains, for example, by using heavy chains of different isotypes, such as an IgG1 and an IgG3 (see FIG. 11 for a schematic representation). It is anticipated that the heavy chains of different isotype will pair much less efficient, if at all, compared to the same heavy chains. Alternatively, it is also possible to engineer the different heavy chains in their constant region such that homodimerization is favored over heterodimerization, e.g., by introducing self-complementary interactions (see, e.g., WO 98/50431 for possibilities, such as "protuberance-into-cavity" strategies (see, WO 96/27011, the entirety of which is incorporated herein by reference)). It is, therefore, another aspect of the invention to provide a method for producing a mixture of antibodies in a recombinant host, the method including the step of: expressing in a recombinant host cell a nucleic acid sequence encoding a common light chain and nucleic acid sequences encoding at least two different heavy chains that differ in the variable region and that are capable of pairing with the common light chain, and wherein the heavy chains further differ in their constant regions sufficiently to reduce or prevent pairing between the different heavy chains. In one embodiment, the heavy chains are of different isotype. In specific embodiments, 3, 4, 5, 6, 7, 8, 9, 10, or more, different heavy chains are expressed. Mixtures of antibodies obtainable by this method are also embodied in the invention. Such mixtures will comprise mainly monospecific antibodies.

Figure 9:
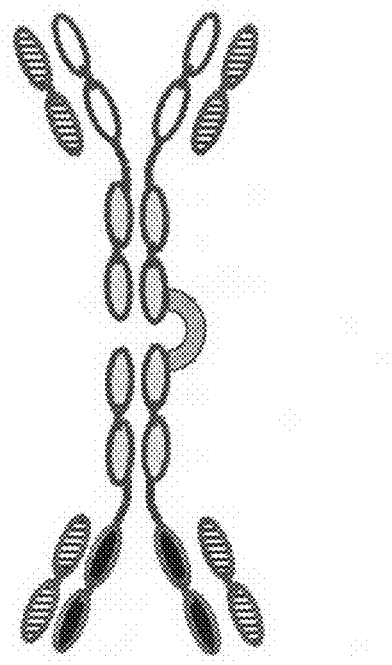
FIG. 9 shows dimeric bispecific IgA with a single light chain (indicated by horizontally striped bar). The method of the invention will produce a mixture of forms wherein different heavy chains can be paired. Only the most simple form is depicted in this schematic representation. A J-chain is shown to join the two monomers.

The teachings of the invention can also be used to obtain novel multispecific antibodies or mixtures thereof. Therefore, in another aspect, the invention provides a method for producing a mixture of antibodies comprising dimeric IgA isotype {(IgA)$_2$} antibodies in a recombinant host, wherein at least part of the dimeric IgA antibodies have different binding regions in each of the IgA sub-units, the method comprising the step of: expressing in a recombinant host cell a nucleic acid sequence encoding a common light chain and nucleic acid sequences encoding at least two different heavy chains of IgA isotype capable of pairing to the common light chain, wherein the different heavy chains differ in their variable region. Dimerization of the IgA molecules can be enhanced by co-expressing J-chain (Yoo et al., 1999, the entirety of which is incorporated herein by reference). Dimeric IgA antibodies have two specificities (see FIG. 9 for a schematic representation of one possible form produced and present in the mixture).

Figure 10:
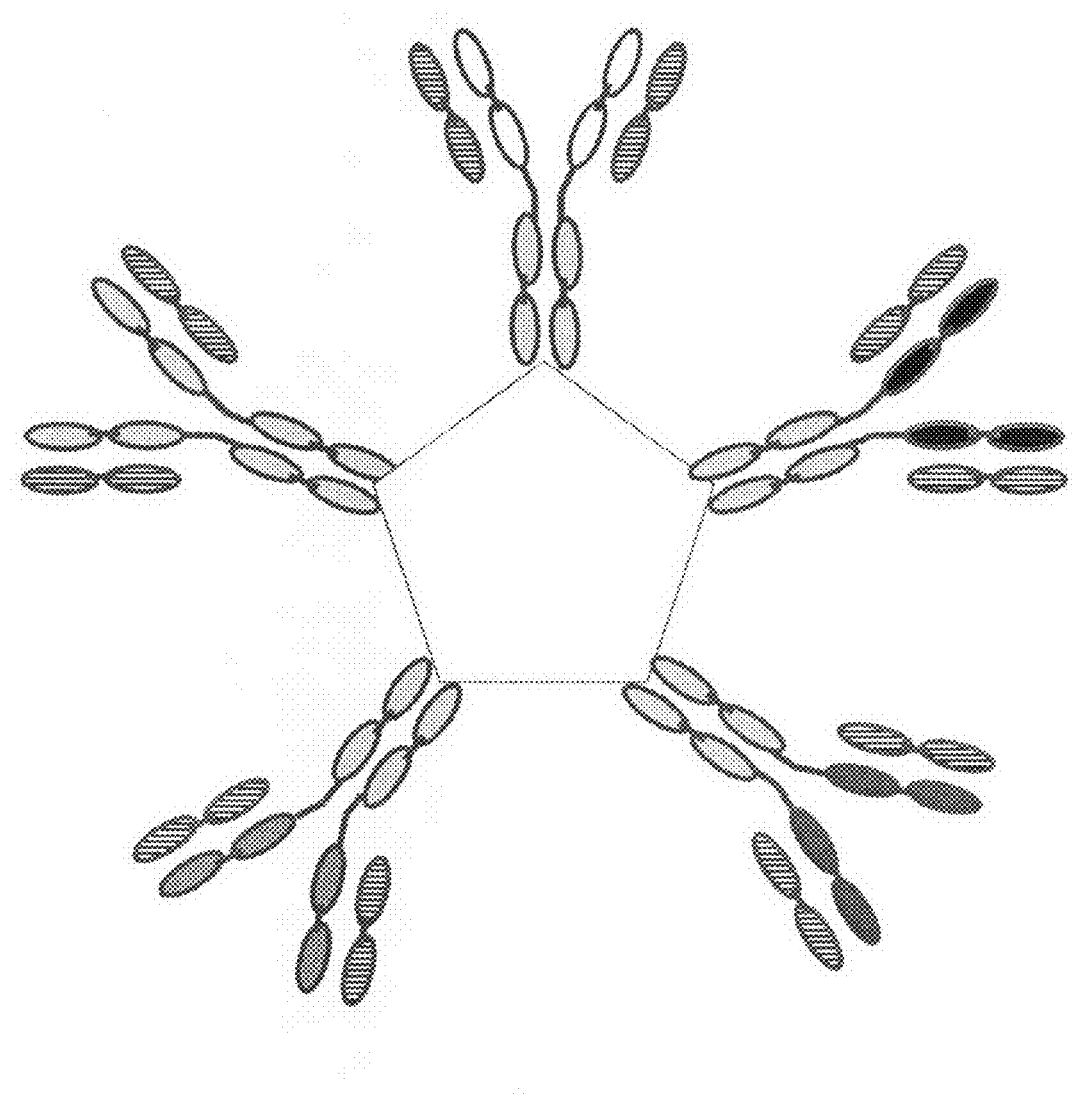
FIG. 10 is a pentameric multispecific IgM with a single light chain (indicated by horizontally striped bars). The method of the invention will produce a mixture of many different forms, wherein different heavy chains can be paired. Only the most simple form is depicted in this schematic representation when five different heavy chains are expressed with a single light chain and all five different heavy chains are incorporated in the pentamer and paired to the same heavy chain. Pentamers with less specificities can also be formed by incorporation of less than five different heavy chains. Hexamers can also be obtained, especially when the J-chain is not expressed.
Figure 11:
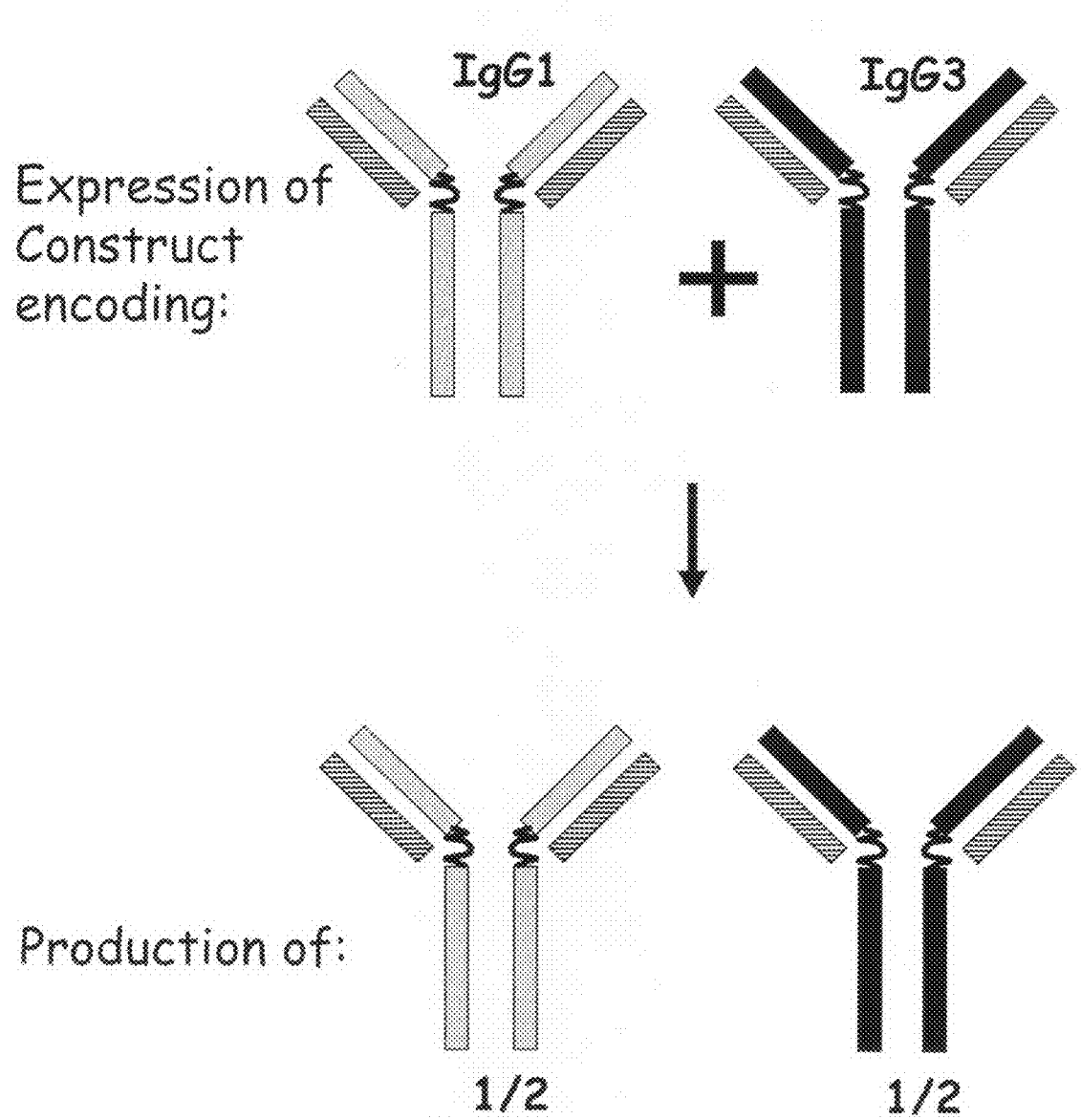
FIG. 11 depicts expression of a mixture of human IgG isotypes consisting of a common light chain but with different binding specificities in a single cell to avoid the formation of bispecific antibodies. The different binding specificities are indicated by the different colors of the $V_H$ sequences. The common light chain is indicated with the vertically striped bars. The IgG1 isotype is indicated with the grey Fc and the IgG3 isotype is indicated with the black Fc part.
Figure 15:
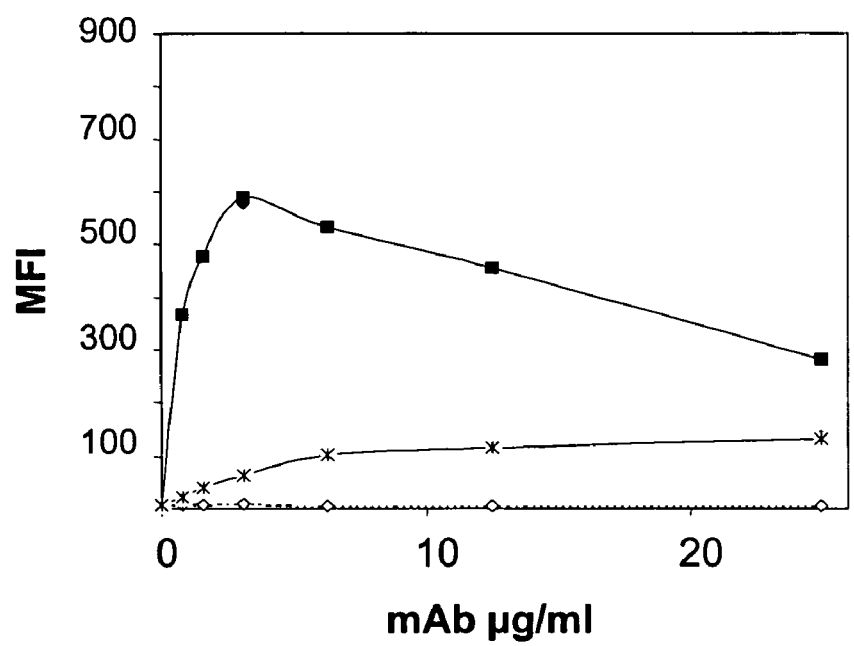
FIG. 15 shows binding of K53 and 02-237 to LS174T cells. Serial dilutions of purified 02-237 (■), K53 (*) and the negative control GBSIII (◇) conjugated to biotin were incubated with LS147T cells preincubated with normal human serum to block Fcγ receptor interaction. Binding (MFI, ordinate) was determined by FACS after incubation with streptavidin-conjugated phycoerythrin.

In certain embodiments, the invention provides a method for producing a mixture of antibodies comprising an IgM antibody having at least two different specificities, the method comprising expressing in a recombinant host cell a nucleic acid sequence encoding a common light chain and nucleic acid sequences encoding at least two different heavy chains of IgM isotype, wherein the heavy chains are capable of pairing to the common light chain and form functional antigen-binding regions. Up to five specificities can be comprised in an IgM pentamer in the presence of a J-chain and up to six in an IgM hexamer in the absence of a J-chain (Yoo et al., 1999). Therefore, in specific embodiments, 3, 4, 5, or 6 IgM heavy chains are co-expressed with the common light chain according to this aspect of the invention. See FIG. 10 for a schematic representation of one of the possible forms that can be produced and present in the mixture according to this aspect of the invention, when five different heavy chains are expressed with a common light chain. Also provided is for IgA dimers, IgM pentamers or hexamers having at least two different specificities. These molecules can be produced from a clone of a single host cell according to the invention. Such molecules harboring antigen-binding regions with different specificities can bind different epitopes on the same antigen, different antigens on one cell, or different antigens on different cells, thereby cross-linking the antigens or cells.

In certain embodiments, the invention provides a method for identifying a mixture of antibodies having a desired effect in a functional assay, the method comprising i) adding a mixture of antibodies in a functional assay, and ii) determining the effect of the mixture in the assay, wherein the mixture of antibodies comprises antibodies having a common light chain. In a preferred embodiment, the mixture is comprised in a composition of the invention.

Also provided is a method for recombinant expression of one or more proteins in a single host cell, wherein at least four different polypeptides are expressed in the single host cell. Each polypeptide is independently expressed and may be under control of a heterologous promoter. The protein or proteins may be isolated separately or as a mixture from a culture of the host cell. Preferably, the host cell of this embodiment is a human cell and/or may be derived from a retina cell, more preferably a cell comprising adenovirus E1 sequences in its genome, most preferably a PER.C6® cell (human retina cells that express adenovirus E1A and E1B proteins).

EXAMPLES

The following examples are provided to illustrate the invention and are not to be construed in any way to limit the scope of the invention. The practice of this invention will employ, unless otherwise indicated, conventional techniques of immunology, molecular biology, microbiology, cell biology, and recombinant DNA, which are within the skill of the art. See, e.g., Sambrook, Fritsch and Maniatis, *Molecular Cloning: A Laboratory Manual*, 2$^{nd}$ edition, 1989; *Current Protocols in Molecular Biology*, F. M. Ausubel, et al., eds, 1987; the series *Methods in Enzymology* (Academic Press, Inc.); *PCR2: A Practical Approach*, M. J. MacPherson, B. D. Hams, G. R. Taylor, eds, 1995; *Antibodies: A Laboratory Manual*, Harlow and Lane, eds, 1988, the entirety of which are incorporated herein by reference.

Example 1

Figure 4:
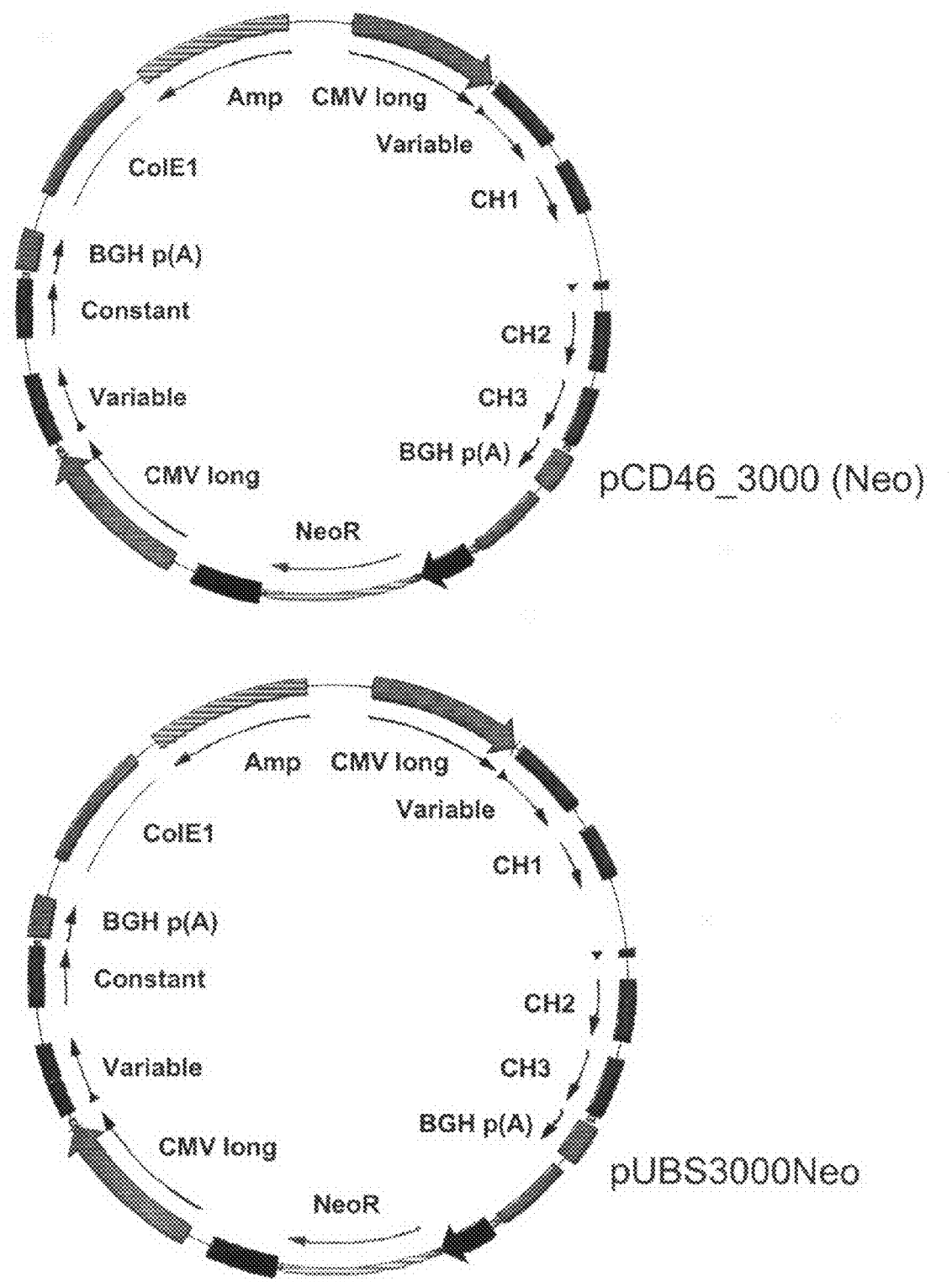
FIG. 4 is an overview of plasmids pUBS3000Neo and pCD46_3000 (Neo).

Production of a Mixture of Monoclonal Antibodies with a Common Light Chain and Two Different Heavy Chain-Variable Regions in a Single Cell Clone UBS-54 and Clone K53 were previously isolated by selections on the colorectal cell line SW40 (Huls et al., 1999) and on a heterogeneous mixture of mononuclear cells of a patient with multiple myeloma (WO 02/18948, the entirety of which is incorporated herein by reference), respectively, with a semi-synthetic library (de Kruif et al., 1995b). Further studies revealed that clone UBS-54 and K53 bound to the EP-CAM homotypic adhesion molecule (Huls et al., 1999) and the membrane cofactor protein CD46 (WO 02/18948), respectively. DNA sequencing of the clones revealed that they were unique in the Heavy chain CDRs, but that they contained an identical light chain sequence (FIG. 3). The $V_H$ and $V_L$ of clones UBS-54 and K53 were inserted into an expression vector containing the HAVT20 leader sequence and all the coding sequences for the constant domains of a human IgG1 with a Kappa light chain by a method essentially as described (Boel et al., 2000), which resulted in plasmids pUBS3000Neo and pCD46_3000(Neo) (FIG. 4). These plasmids were transiently expressed, either alone or in combination in PER.C6® cells (human retina cells that express adenovirus E1A and E1B proteins). In brief, each 80 cm$^2$ flask was transfected by incubation for four hours with 140 µl lipofectamine+10 µg DNA (either pUBS3000Neo, pCD46_3000(Neo) or 10 µg of both) in serum-free DMEM medium at 37° C. After four hours this was replaced with DMEM+10% FBS and the cells were grown overnight at 37° C. Cells were then washed with PBS and the medium was replaced with Excell 525 medium (JRH Bioscience). The cells were allowed to grow at 37° C. for six days, after which the cell culture supernatant was harvested. Human IgG-specific ELISA analysis (described in WO 00/63403, the entirety of which is incorporated herein by reference) indicated that IgG was present at approximately 10 µg/ml for all flasks containing expression plasmids. No IgG1 was present in a control flask which was not transfected with expression plasmid.

Figure 5:
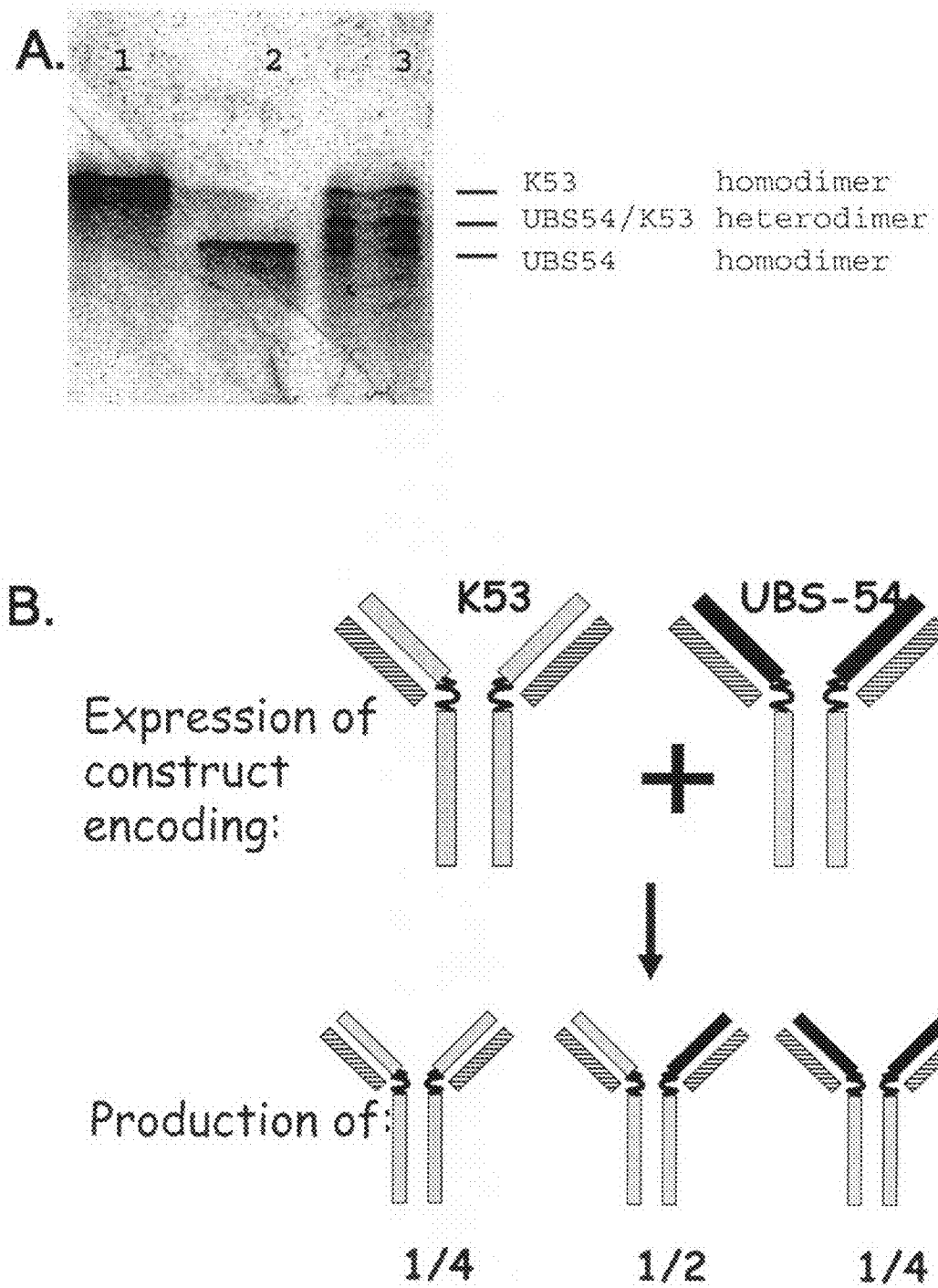
FIG. 5, Panel A, shows the isoelectric focusing (IEF) of transiently expressed pUBS3000Neo, pCD46_3000(Neo) and a combination of both. In Panel B, the upper part shows a schematic representation of the expected molecules when a single light chain and a single heavy chain are expressed in a cell, leading to monoclonal antibodies UBS-54 or K53. The lower part under the arrow shows a schematic representation of the combinations produced when both heavy chains and the common light chain are co-expressed in a host cell, with theoretical amounts when both heavy chains are expressed at equal levels and pair to each other with equal efficiency. The common light chain is indicated with the vertically striped bars.

Human IgG from each supernatant was subsequently purified using Protein A-affinity chromatography (Hightrap Protein A HP, cat. no. 1-040203) according to standard procedures, following recommendations of the manufacturer (Amersham Biosciences). After elution, samples were concentrated in a Microcon YM30 concentrator (Amicon) and buffer exchanged to 10 mM sodium phosphate, pH 6.7. Twelve μg of purified IgG was subsequently analyzed on Isoelectric-focusing gels (Serva Pre-cast IEF gels, pH range 3-10, cat. no. 42866). The samples were loaded on the low pH side and after focusing, stained with colloidal blue (FIG. 5). Lane 1 shows transiently expressed K53, Lane 2 shows transiently expressed UBS-54 and Lane 3 shows the IgG sample of the cells in which both antibodies were co-transfected. Clearly, K53 and UBS-54 each have a unique pI profile and the sample from the co-transfection showed other unique isoforms, with the major isoform having a pI in between those of K53 and UBS-54. This is also anticipated on the basis of the theoretic pI when calculated with the ProtParam tool provided on the Expasy homepage (expasy.ch; Appel et al., 1994, the entirety of which is incorporated herein by reference). K53 and UBS-54 have a theoretic pI of 8.24 and 7.65, respectively, whereas an isoform representing a heterodimer of one UBS-54 heavy chain and one K53 heavy chain has a theoretical pI of 8.01. Assembly of such a heterodimer can only occur when a single cell translates both the heavy chain of K53 and the heavy chain of UBS-54 and assembles these into a full length IgG molecule together with the common light chain.

Therefore, this experiment shows that it is possible to express two unique human IgG molecules in a single cell and that a heterodimer consisting of these two unique binding specificities is also efficiently formed.

Example 2

Figure 6:
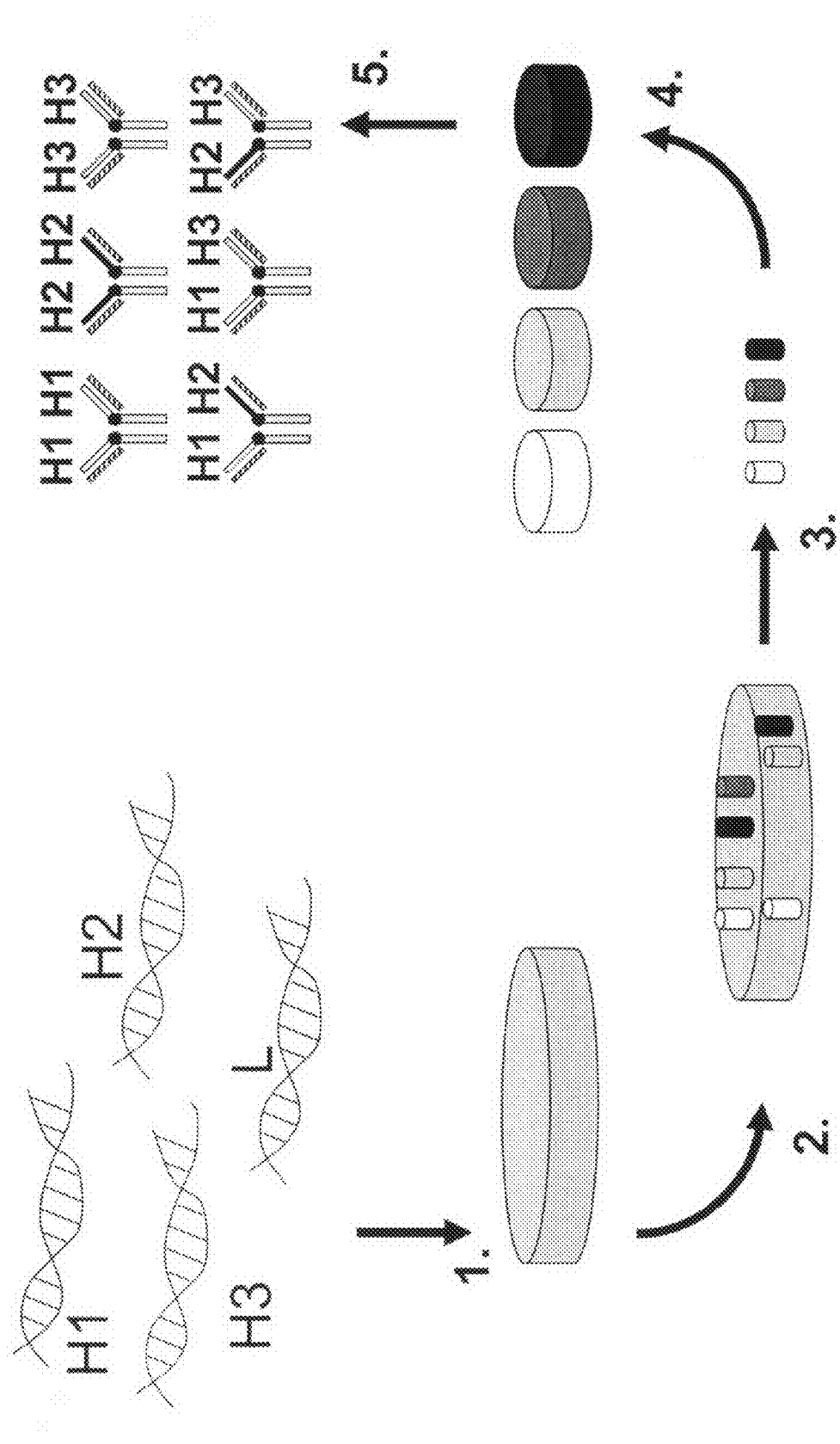
FIG. 6 is a schematic representation of a possible embodiment of the method according to the invention (see, e.g., Example 9). At (1), introduction of nucleic acid sequences encoding one light chain and three different heavy chains capable of pairing to the common light chain to give functional antibodies into host cells is shown; at (2), selection of stable clones; (3) shows clones can be screened for, for instance, expression levels, binding; at (4), clones are expanded; and at (5), production of functional mixtures of antibodies is shown. Some or all of steps 2-5 could be performed simultaneously or in a different order.

Production of a Mixture of Antibodies Against Human B-Cell Markers in a PER.C6® Cell Line (Human Retina Cells that Express Adenovirus E1A and E1B Proteins)-Derived Clone A method for producing a mixture of antibodies according to the invention, using expression in a recombinant host cell of a single light chain and three different heavy chains capable of pairing to the single light chain to form functional antibodies, is exemplified herein and is schematically shown in FIG. 6. Phages encoding antibodies capable of binding proteins present on human B-cells, i.e., CD22, CD72 and Major Histocompatibility Complex (MHC) class II (further referred to as HLA-DR) were previously isolated from a semi-synthetic phage library (de Kruif et al., 1995; van der Vuurst de Vries & Logtenberg, 1999, the entirety of which is incorporated herein by reference). DNA sequencing of the $V_H$ and $V_L$ sequences of the phages clone B28 (anti-CD22), clone 1-2 (anti-HLA-DR) and clone II-2 (anti-CD72) revealed that they all contain a unique $V_H$ sequence but a common light chain sequence (Vλ3) with an identical CDR region (FIG. 7).

The $V_H$ and $V_L$ sequences of clones B28, I-1 and II-2 are cloned behind the HAVT20 leader sequences of an expression plasmid comprising a heavy chain. An example of such a plasmid is pCRU-K01 (contains kappa heavy chain sequences that can be easily interchanged for lambda heavy chain sequences if desired by a person skilled in the art), as deposited at the ECACC under number 03041601. The cloning gives rise to plasmids encoding a full length human IgG1 with binding specificities for CD22, CD72 and HLA-DR. These plasmids will further be referred to as pCRU-CD22, pCRU-CD72 and pCRU-HLA-DR, respectively.

Stable PER.C6® (human retina cells that express adenovirus E1A and E1B proteins)-derived cell lines are generated, according to methods known to one of ordinary skill in the art (see, e.g., WO 00/63403), the cell lines expressing antibodies encoded by genetic information on either pCRU-CD22, pCRU-CD72 or pCRU-HLA-DR and a cell line expressing antibodies encoded by all three plasmids. Therefore, PER.C6® cells (human retina cells that express adenovirus E1A and E1B proteins) are seeded in DMEM plus 10% FBS in tissue culture dishes (10 cm diameter) or T80 flasks with approximately $2.5 \times 10^6$ cells per dish and kept overnight under their normal culture conditions (10% $CO_2$ concentration and 37° C.). The next day, transfections are performed in separate dishes at 37° C. using Lipofectamine (Invitrogen Life Technologies) according to standard protocols provided by the manufacturer, with either 1-2 μg pCRU-CD22, 1-2 μg pCRU-CD72, 1-2 μg pCRU-HLA-DR or 1 μg of a mixture of pCRU-CD22, pCRU-CD72 and pCRU-HLA-DR. As a control for transfection efficiency, a few dishes are transfected with a LacZ control vector, while a few dishes will not be transfected and serve as negative controls.

After four to five hours, cells are washed twice with DMEM and given fresh medium without selection. The next day, the medium is replaced with fresh medium containing 500 μg/ml G418. Cells are refreshed every two or three days with medium containing the same concentrations of G418. About 20 to 22 days after seeding, a large number of colonies are visible and from each transfection, at least 300 are picked and grown via 96-well plates and/or 24-well plates via 6-well plates to T25 flasks. At this stage, cells are frozen (at least one, but usually four vials per sub-cultured colony) and production levels of recombinant human IgG antibody are determined in the supernatant using an ELISA specific for human IgG1 (described in WO 00/63403). Also, at this stage, G418 is removed from the culture medium and never re-applied again. For a representative number of colonies, larger volumes will be cultured to purify the recombinant human IgG1 fraction from the conditioned supernatant using Protein A affinity chromatography according to standard procedures. Purified human IgG1 from the various clones is analyzed on SDS-PAGE, Iso-electric focusing (IEF) and binding to the targets CD22, CD72 and HLA-DR using cell transfectants expressing these human antigens on their cell surface (transfectants expressing CD72 and HLA-DR have been described by van der Vuurst-de Vries and Logtenberg, 1999; a CD22 transfectant has been prepared according to similar standard procedures in PER.C6® (human retina cells that express adenovirus E1A and E1B proteins)).

Colonies obtained from the co-transfection with pCRU-CD22, pCRU-CD72 and pCRU-HLA-DR are screened by PCR on genomic DNA for the presence or absence of each of the three constructs. The identity of the PCR products is further confirmed by DNA sequencing.

Next, it is demonstrated that a clonal cell line accounts for the production of each of the three binding specificities, i.e., proving that a single cell is able to produce a mixture of more than two functional human IgGs. Therefore, a limited number of colonies, which screened positive for the production of each of the three binding specificities (both by PCR at the DNA level as well as in the specified binding assays against CD22, CD72 and HLA-DR), are subjected to single cell sorting using a fluorescence-activated cell sorter (FACS) (Becton & Dickinson FACS VANTAGE SE™ (high-performance, high-speed cell sorter)). Alternatively, colonies are seeded at 0.3 cells/well to guarantee clonal outgrowth. Clonal cell populations, hereafter designated as sub-clones, are refreshed once a week with fresh medium. Sub-clones are grown and transferred from 96-well plates via 24- and 6-well plates to T25 flasks. At this stage, sub-clones are frozen (at least one, but usually four vials per sub-clone) and production levels of recombinant human IgG1 antibody are determined in the supernatant using a human IgG1-specific ELISA. For a representative number of sub-clones, larger volumes are cultured to purify the recombinant human IgG1 fraction from the conditioned supernatant using Protein A-affinity chromatography according to standard procedures.

Purified human IgG1 from the various sub-clones is subsequently analyzed as described above for human IgG1 obtained from the parental clones, i.e., by SDS-PAGE, Iso-electric focusing (IEF) and binding to the targets CD22, CD72 and HLA-DR. Sub-clones will also be screened by PCR on genomic DNA for the presence or absence of each of the three constructs pCRU-CD22, pCRU-CD72 and pCRU-HLA-DR. The identity of the PCR products is further confirmed by DNA sequencing.

Other methods such as Southern blot and/or FISH can also be used to determine whether each of the three constructs are present in the clonal cell line.

Sub-clones that are proven to be transgenic for each of the three constructs are brought into culture for an extensive period to determine whether the presence of the transgenes is stable and whether expression of the antibody mixture remains the same, not only in terms of expression levels, but also for the ratio between the various antibody isoforms that are secreted from the cell. Therefore, the sub-clone culture is maintained for at least 25 population doubling times, either as an adherent culture or as a suspension culture. At every four to six population doublings, a specific production test is performed using the human IgG-specific ELISA and larger volumes are cultured to obtain the cell pellet and the supernatant. The cell pellet is used to assess the presence of the three constructs in the genomic DNA, either via PCR, Southern blot and/or FISH. The supernatant is used to purify the recombinant human IgG1 fraction as described supra. Purified human IgG1 obtained at the various population doublings is analyzed as described, i.e., by SDS-PAGE, Iso-electric focusing (IEF) and binding to the targets CD22, CD72 and HLA-DR using cell transfectants expressing these antigens.

Example 3

Screening of Clones Expressing Multiple Human IgGs for the Most Potent Mixture of Functional Human IgGs Functionality of the antibody mixture is analyzed in cell-based assays to determine whether the human IgG1 mixture inhibits proliferation and/or induces apoptosis of B-cell lines, such as, for example, Ramos. Other cell lines can also be used. In addition, the antibody mixtures are analyzed for their potential to induce antibody-dependent cellular toxicity and complement-dependent cytotoxicity of, for example, Ramos cells.

In each of the following experiments, the functionality of the antibody mixture recognizing the targets CD22, CD72 and HLA-DR is analyzed and can be compared to each of the individual IgG1 antibodies and to an equimolar combination of the three individual IgG1 specificities.

To assess the ability of the antibody mixtures to inhibit the proliferation of Ramos cells, these cells are incubated in 96-well plates (0.1-1.0×10$^5$/ml) with several concentrations (5-20 μg/ml) of the antibody mixtures against CD22, CD72 and HLA-DR for 24 hours. The proliferation of the cells is measured by $^3$H-thymidine incorporation during another 16 hours of culture. Inhibition of growth is determined by plotting the percentage of $^3$H-thymidine incorporation compared to untreated cells (taken as 100% reference value).

To analyze apoptosis induction of Ramos cells, these cells are stimulated in 48-well plates (0.2-1.0×10$^6$/ml) with several concentrations (5-20 μg/ml) of the antibody mixtures against the targets CD22, CD72 and HLA-DR for 24 or 48 hours. After the incubation period, the phosphatidyl serine exposure on apoptotic cells is analyzed (G. Koopman et al., 1994, the entirety of which is incorporated herein by reference). Therefore, the cells are harvested, washed twice with PBS and are incubated at RT for 10 minutes with 100 μl FITC-labeled annexin V (Caltag) diluted 1:25 in annexin V-binding buffer (Caltag). Prior to the analysis of the samples by flow cytometry (FACSCalibur, Becton Dickinson, San Jose, Calif.), propidium iodide (PI)(Sigma) is added to a final concentration of 5 μg/ml to distinguish necrotic cells (annexin V−/PI+) from apoptotic cells (annexin V+/PI−, early apoptotic cells; annexin V+/PI+, late apoptotic cells).

In an alternative assay, apoptosis is induced by cross-linking the antibody mixtures against CD22, CD72 and HLA-DR on the cell surface of Ramos cells with 25 μg/ml of F(ab)2 of goat-anti-human (Fc-specific) polyclonal antibodies (Jackson ImmunoResearch Laboratories, West Grove, Pa.) during the incubation period.

In another alternative assay, apoptosis is induced by incubating the Ramos cells with several concentrations (5-20 μg/ml) of the antibody mixtures against CD22, CD72 and HLA-DR while co-incubating them with the chemosensitizing agents doxorubicin (Calbiochem) or dexamethasone (UMCU, Utrecht, NL).

Antibody-Dependent Cellular Cytotoxicity (ADCC) of the antibody mixtures is analyzed using peripheral blood mononuclear cells as effector cells in a standard $^{51}$Cr release assay (Huls et al., 1999). To this purpose, 1-3×10$^6$ Ramos cells are labeled with 100 μCi (Amersham, Buckinghamshire, UK) for one hour at 37° C. After three washes with medium, the Ramos target cells are plated in U bottom 96-well plates at 5×10$^3$ cells/well. Peripheral blood mononuclear cells that are obtained from healthy donors by Ficoll-Hypaque density gradients are then added to each well at effector:target ratios ranging from 80:1 to 10:1 in triplicate. The cells are incubated at 37° C. in the presence of various concentrations of the antibody mixtures (5-20 μg/ml) in a final volume of 200 μl.

After four hours of incubation, part of the supernatant is harvested and $^{51}$Cr release is measured. The percentage of specific lysis is calculated using the following formula: % specific lysis=([experimental cpm−spontaneous cpm]/[maximal cpm−spontaneous cpm]×100%). Maximal $^{51}$Cr release is determined by adding triton X-100 to a final concentration of 1% to the target cells and spontaneous release is determined after incubation of the target cells with medium alone.

Complement-dependent cytotoxicity is determined in a similar assay. Instead of the effector cells, now 50 μl human serum is added to the target cells. Subsequently, the assay is performed in the same manner.

Alternatively, ADCC and CDC of the antibody mixtures is determined using a Europium release assay (Patel and Boyd, 1995, the entirety of which is incorporated herein by reference) or using an LDH release assay (Shields et al., 2001, the entirety of which is incorporated herein by reference).

Example 4

Use of Phage Display to Isolate Multiple Phages with an Identical $V_L$ Sequence Against a Predefined Target (Her-2) and Production in a Recombinant Host Cell of a Mixture of Antibodies Capable of Binding this Target Phages displaying scFv fragments capable of binding multiple epitopes present on the same protein, for example, the epidermal growth factor receptor Her-2, can be isolated from a semi-synthetic phage library (de Kruif et al., 1995a, b). It is possible to identify several of such phages and select the ones comprising the same light chain sequence for further use according to the invention. The semi-synthetic library is formed by mixing seven sub-libraries that each contain a different light chain (de Kruif et al., 1995a, b). It is, therefore, particularly practical to use such a sub-library, containing only one light chain and many heavy chains, for screening so that multiple antibodies with an identical $V_L$ sequence are obtained and further used for expressing the antibody mixtures according to the invention.

For the selection of phages against Her-2, several fusion proteins are generated comprising different parts of the extracellular domain of Her-2 that are fused to the CH2 and CH3 domains of human IgG1. For this purpose, a pcDNA3.1zeo-expression vector (InVitrogen) has been constructed that contains in its multiple cloning region an XhoI restriction site in the hinge region in frame prior to the CH2 and CH3 domains of human IgG1. Using a Her-2 cDNA clone as a template, PCR fragments are generated using standard molecular biology techniques known to a person skilled in the art. These fragments consist of a unique 5' restriction site, a start codon followed by a eukaryotic leader sequence that is linked in frame to either the total extracellular (EC) domain of Her-2 or to a part of the EC domain of Her-2 that is followed in frame by an XhoI restriction site. These PCR fragments are subsequently cloned in frame with the CH2-CH3 IgG1 region into the pcDNA3.1zeo-expression vector. In addition to the fusion protein containing the total EC domain of Her-2, several smaller fusion proteins are generated containing non-overlapping fragments of the Her-2 EC domain. These constructs encoding the Her-2-Ig fusion proteins are used for transient transfection of 293T cells using the lipofectamine reagent (Gibco). Five days after transfection, the supernatants of the 293T cells are harvested and Her-2-Ig fusion proteins are purified using protein A-affinity chromatography according to standard procedures.

Her-2-Ig fusion proteins containing non-overlapping fragments of the Her-2 EC domain are coated for two hours at 37° C. onto the surface of MAXISORP™ (polystyrene based modified surface with a high affinity for polar groups) plastic tubes (Nunc) at a saturating concentration (0.5-5 µg/ml). The tubes are blocked for one hour in 2% fat-free milk powder dissolved in PBS (MPBS). Simultaneously, 500 µl (approximately $10^{13}$ cfu) of a semi-synthetic phage display library (a sub-library according to the terminology used above) in which only one Vκ light chain is represented (prepared as described by De Kruif et al. (1995a, b) and referenced therein), is added to two volumes of 4% MPBS. In addition, human serum is added to a final concentration of 15% and blocking is allowed to proceed for 30 to 60 minutes. The Her-2-Ig-coated tubes are emptied and the blocked phage library is added. The tube is sealed and rotated slowly for one hour, followed by two hours of incubation without rotation. The tubes are emptied and washed ten times in PBS containing 0.1% Tween-20, followed by washing five times in PBS. One ml glycine-HCL, 0.05 M, pH 2.2 is added, and the tube is rotated slowly for ten minutes. The eluted phages are added to 500 µl 1 M Tris-HCl pH 7.4. To this mixture, 3.5 ml of exponentially growing XL-1 blue bacterial culture is added. The tubes are incubated for 30 minutes at 37° C. without shaking. Subsequently, the bacteria are plated on 2TY agar plates containing ampicillin, tetracycline and glucose. After overnight incubation of the plates at 37° C., the colonies are scraped from the plates and used to prepare an enriched phage library, essentially as described by De Kruif et al. (1995a). Briefly, scraped bacteria are used to inoculate 2TY medium containing ampicillin, tetracycline and glucose and are grown at 37° C. to an $OD_{600nm}$ of ~0.3. Helper phages are added and allowed to infect the bacteria after which the medium is changed to 2TY containing ampicillin, tetracycline and kanamycin. Incubation is continued overnight at 30° C. The next day, the bacteria are removed from the 2TY medium by centrifugation, after which the phages are precipitated using polyethylene glycol 6000/NaCl. Finally, the phages are dissolved in a small volume of PBS-1% BSA, filter-sterilized and used for a next round of selection. The selection/re-infection procedure is performed twice. After the second round of selection, individual E. coli colonies are used to prepare monoclonal phage antibodies. Essentially, individual colonies are grown to log phase and infected with helper phages, after which phage antibody production is allowed to proceed overnight. Phage antibody containing supernatants are tested in ELISA for binding activity to Her-2-total EC-Ig coated 96-well plates.

Selected phage antibodies that are obtained in the screen described above are validated by ELISA for specificity. For this purpose, Her-2-Ig fusion proteins containing non-overlapping fragments of the Her-2 EC domain are coated to Maxisorp ELISA plates. After coating, the plates are blocked in 2% MPBS. The selected phage antibodies are incubated in an equal volume of 4% MPBS. The plates are emptied, washed once in PBS, after which the blocked phages are added. Incubation is allowed to proceed for one hour, the plates are washed in PBS 0.1% Tween-20 and bound phages are detected using an anti-M13 antibody conjugated to peroxidase. The procedure is performed simultaneously using a control phage antibody directed against thyroglobulin (De Kruif et al. 1995a, b), which serves as a negative control.

In another assay, the selected phage antibodies are analyzed for their ability to bind BT474 human breast cancer cells that express Her-2. For flow cytometry analysis, phage antibodies are first blocked in an equal volume of 4% MPBS for 15 minutes at 4° C. prior to the staining of the BT474 cells. The binding of the phage antibodies to the cells is visualized using a biotinylated anti-M13 antibody (Santa Cruz Biotechnology) followed by streptavidin-phycoerythrin (Caltag).

Alternatively, phage antibodies recognizing multiple epitopes on Her-2 are selected using a method based upon competition of phage binding to Her-2 with binding of the well-characterized murine anti-Her-2 antibodies HER50, HER66 and HER70 (Spiridon et al., 2002, the entirety of which is incorporated herein by reference). To this purpose, $2 \times 10^6$ BT474 cells are incubated at 4° C. with approximately $10^{13}$ cfu (0.5 ml) of a semi-synthetic phage display library in which only one Vκ1 light chain is represented, prepared as described supra, and blocked with two volumes of medium containing 10% of FBS. The mixture is slowly rotated at 4° C. for two hours in a sealed tube.

Subsequently, non-bound phages are removed by two washes with 50 ml of cold medium containing 10% FBS. Hereafter, phages recognizing multiple epitopes on Her-2 are eluted by resuspending the BT474 cells in 1 ml of cold medium containing saturating concentrations (5-20 µg/ml) of the HER50, HER66 and HER70 murine anti-Her-2 antibodies. The cells are left on ice for 10 minutes, spun down and the supernatant containing the anti-Her-2 phage antibodies is used to reinfect XL1-Blue cells as described supra.

From the panel of Her-2-specific phage antibodies generated by the screens described above, three phage antibodies are selected that recognize three different non-overlapping epitopes on the Her-2 protein.

The $V_H$ sequences and the unique Vκ1 light chain sequence of these clones, provisionally designated Vκ1HER2-1, Vκ1HER2-2 and Vκ1HER2-3, are cloned behind the HAVT20 leader sequences of expression plasmid pCRU-K01 (ECACC deposit 03041601), or a similar expression plasmid, to obtain plasmids encoding a full-length human IgG1-K with binding specificities for Her-2. These plasmids are provisionally designated as pCRU-Vκ1HER2-1, pCRU-Vκ1HER2-2 and pCRU-Vκ1HER2-3, respectively.

Stable PER.C6® (human retina cells that express adenovirus E1A and E1B proteins)-derived cell lines are generated, according to methods known to one of ordinary skill in the art, the cell lines expressing antibodies encoded by genetic information on either pCRU-Vκ1HER2-1, pCRU-Vκ1HER2-2 or pCRU-Vκ1HER2-3 and a cell line expressing antibodies encoded by all three plasmids. Therefore, PER.C6® cells are seeded in DMEM plus 10% FBS in tissue culture dishes (10 cm diameter) or T80 flasks with approximately $2.5 \times 10^6$ cells per dish and kept overnight under their normal culture conditions (10% $CO_2$ concentration and 37° C.). The next day, transfections are performed in separate dishes at 37° C. using Lipofectamine (Invitrogen Life Technologies) according to standard protocols provided by the manufacturer, with either 1-2 µg pCRU-Vκ1HER2-1, 1-2 µg pCRU-Vκ1HER2-2, 1-2 µg pCRU-Vκ1HER2-3 or 1 µg of a mixture of pCRU-Vκ1HER2-1, pCRU-Vκ1HER2-2 and pCRU-Vκ1HER2-3. As a control for transfection efficiency, a few dishes are transfected with a LacZ control vector, while a few dishes are not transfected and serve as negative controls.

After five hours, cells are washed twice with DMEM and re-fed with fresh medium without selection. The next day, medium is replaced with fresh medium containing 500 µg/ml G418. Cells are refreshed every two or three days with medium containing the same concentrations of G418. About 20 to 22 days after seeding, a large number of colonies are visible and from each transfection, at least 300 are picked and grown via 96-well plates and/or 24-well plates via 6-well plates to T25 flasks. At this stage, cells are frozen (at least one, but usually four vials per sub-cultured colony) and production levels of recombinant human IgG antibody are determined in the supernatant using an ELISA specific for human IgG1. Also, at this stage, G418 is removed from the culture medium and never re-applied again. For a representative number of colonies, larger volumes are cultured to purify the recombinant human IgG1 fraction from the conditioned supernatant using Protein A-affinity chromatography according to standard procedures. Purified human IgG1 from the various clones is analyzed on SDS-PAGE, Iso-electric focusing (IEF), assayed binding to Her-2-Ig fusion proteins by ELISA, and analyzed for binding to Her-2 on the surface of BT474 cells by flow cytometry.

Clones obtained from the co-transfection of pCRU-Vκ1HER2-1, pCRU-Vκ1HER2-2 and pCRU-Vκ1HER2-3 are screened by PCR on genomic DNA for the presence or absence of each of the three constructs. The identity of the PCR products is further confirmed by DNA sequencing.

Next, it is demonstrated that a clonal cell line accounts for the production of each of the three binding specificities. Therefore, a limited number of colonies, which screened positive for the production of each of the three binding specificities (both by PCR at the DNA level as well as in the specified binding assays against Her-2), are subjected to single cell sorting using a fluorescence-activated cell sorter (FACS) (Becton & Dickinson FACS VANTAGE SE™). Alternatively, colonies are seeded at 0.3 cells/well to guarantee clonal outgrowth.

Clonal cell populations, hereafter designated as sub-clones, are refreshed once a week with fresh medium. Sub-clones are grown and transferred from 96-well plates via 24- and 6-well plates to T25 flasks. At this stage, sub-clones are frozen (at least one, but usually four vials per sub-clone) and production levels of recombinant human IgG1 antibody are determined in the supernatant using a human IgG1-specific ELISA. For a representative number of sub-clones, larger volumes are cultured to purify the recombinant human IgG1 fraction from the conditioned supernatant using Protein A-affinity chromatography according to standard procedures.

Purified human IgG1 from the various sub-clones is subsequently analyzed as described above for human IgG1 obtained from the parental clones, i.e., by SDS-PAGE, Iso-electric focusing (IEF) and binding to Her-2. Sub-clones will also be screened by PCR on genomic DNA for the presence or absence of each of the three constructs pCRU-Vκ1HER2-1, pCRU-Vκ1HER2-2 and pCRU-Vκ1HER2-3. The identity of the PCR products is further confirmed by DNA sequencing.

Other methods such as Southern blot and/or FISH can also be used to determine whether each of the three constructs are present in the clonal cell line.

Sub-clones that are proven to be transgenic for each of the three constructs are brought into culture for an extensive period to determine whether the presence of the transgenes is stable and whether expression of the antibody mixture remains the same, not only in terms of expression levels, but also for the ratio between the various antibodies that are secreted from the cell. Therefore, the sub-clone culture is maintained for at least 25 population doubling times, either as an adherent culture or as a suspension culture. At every four to six population doublings, a specific production test is performed using the human IgG-specific ELISA and larger volumes are cultured to obtain the cell pellet and the supernatant. The cell pellet is used to assess the presence of the three constructs in the genomic DNA, either via PCR, Southern blot and/or FISH. The supernatant is used to purify the recombinant human IgG1 fraction as described supra. Purified human IgG1 obtained at the various population doublings is analyzed as described, i.e., by SDS-PAGE, Iso-electric focusing (IEF) and binding to Her-2 by ELISA and by flow cytometry using BT474 cells.

Functionality of the antibody mixture of anti-Her-2 antibodies is analyzed in cell-based assays to determine whether the human IgG1 mixture inhibits proliferation and/or induces apoptosis of BT474 cells. In addition, the antibody mixtures are analyzed for their potential to induce antibody-dependent cellular toxicity and complement-dependent cytotoxicity of BT474 cells.

In each of the experiments described below, the functionality of the antibody mixture recognizing Her-2 can be analyzed and compared to each of the individual IgG1 antibodies and to an equimolar combination of the three individual monospecific IgG1 molecules.

To assess the ability of the antibody mixtures to inhibit the proliferation of BT474 cells, these cells are allowed to adhere overnight in 96-well plates ($1.5 \times 10^5$/well) and are subsequently incubated with several concentrations (5-20 µg/ml) of the antibody mixtures against Her-2 for 72 hours. The proliferation of the cells is measured by $^3$H-thymidine incorporation during the last six hours of culture. Inhibition of growth is determined by plotting the percentage of $^3$H-thymidine incorporation compared with untreated cells (taken as 100% reference value).

To analyze apoptosis induction of BT474 cells, these cells are allowed to adhere overnight in 48-well plates ($2.5 \times 10^5$/well in 1 ml) and are subsequently incubated with several concentrations (5-20 µg/ml) of the antibody mixtures against Her-2 for four hours. Hereafter, the cells are harvested by trypsinization, washed twice with PBS and incubated at RT for ten minutes with 100 µl FITC-labeled annexin V (Caltag) diluted 1:25 in annexin V-binding buffer (Caltag). Prior to the analysis of the samples by flow cytometry (FACSCalibur, Becton Dickinson, San Jose, Calif.) propidium iodide (PI) (Sigma) is added to a final concentration of 5 µg/ml to distinguish necrotic cells (annexin $V^-$/$PI^+$) from apoptotic cells (annexin $V^+$/$PI^-$, early apoptotic cells; annexin $V^+$/$PI^+$, late apoptotic cells).

Antibody-Dependent Cellular Cytotoxicity of the antibody mixtures is analyzed using peripheral blood mononuclear cells as effector cells and BT474 cells as target cells in a standard $^{51}$Cr release assay as described supra (Huls et al., 1999). Complement-dependent cytotoxicity is determined in a similar assay. Instead of the effector cells, now 50 µl human serum is added to the target cells. Subsequently, the assay is performed as described supra.

Alternatively, ADCC and CDC of the antibody mixtures is determined using a Europium release assay (Patel and Boyd, 1995) or using an LDH release assay (Shields et al., 2001).

The functionality of the antibody mixtures against Her-2 is also tested using in vivo animal models, such as, for instance, described in Spiridon et al., 2002.

Example 5

Expression of Different Functional Human IgGs in the Milk of Transgenic Animals

The $V_H$ and $V_H$ sequences of phages against proteins present on human B-cells, i.e., CD22 (clone B28), CD72 (clone II-2) and HLA-DR (clone I-2) (FIG. 7) are cloned into expression plasmid pBC1 (as provided in the pBC1 Mouse Milk Expression System, Invitrogen Life Technologies) to obtain mammary gland- and lactation-specific expression of these human IgG molecules in transgenic animals, according to the manufacturer's instructions. These mammary gland-specific expression vectors encoding the antibody sequences for anti-CD22, anti-CD72 and anti-HLA-DR, are introduced into the murine germline according to the manufacturer's instructions. Obtained pups are screened for the presence of each of the three constructs by PCR on DNA isolated from the tail. Pups, either male or female, confirmed for being transgenic for each of the three antibodies, are weaned and matured. Female transgenic mice are fertilized at the age of 6-8 weeks and milk samples are obtained at several time points after gestation. Male transgenic mice are mated with non-transgenic females and female transgenic offspring (as determined with PCR as described above) is mated and milked as described above for the female transgenic founders. Whenever needed, female or male transgenic founders are mated for another generation to be able to obtain sufficient amounts of transgenic milk for each founder line. Transgenic milk is analyzed for the presence of human IgG with a human IgG-specific ELISA, which does not cross-react with mouse IgG or other mouse milk components. Human IgG is purified from transgenic mouse milk using Protein A-affinity chromatography according to standard procedures. Purified human IgG is analyzed on SDS-PAGE, Iso-electric focusing and binding on the targets CD22, CD72 and HLA-DR. Functionality of the antibody mixture is analyzed as described supra.

Example 6

Figure 8:
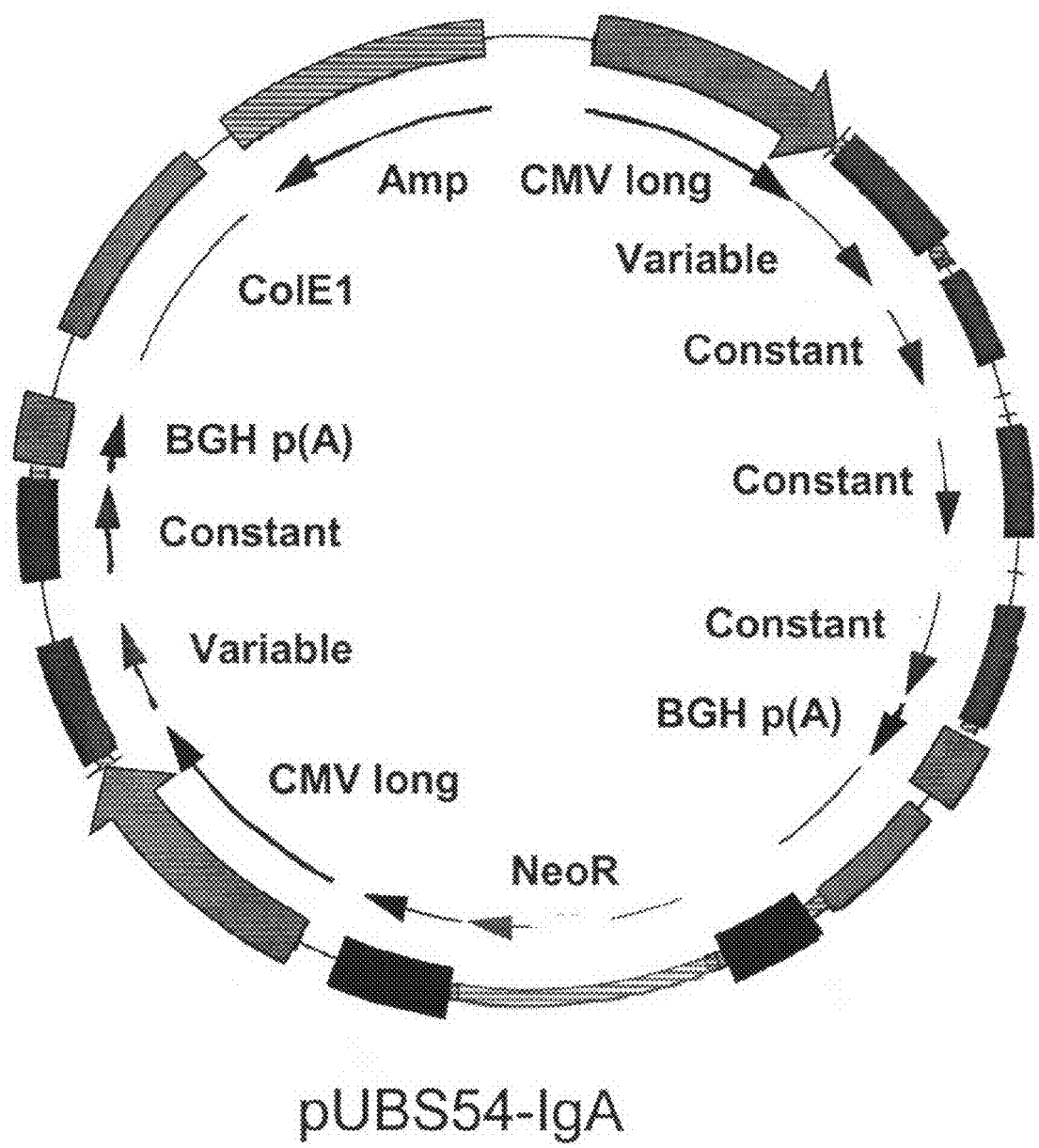
FIG. 8 is a map of pUBS54-IgA (pCRU-L01 encoding human IgA1 against EPCAM).

Production of an IgA/IgG Mixture Against a Predefined Target in a PER.C6® (Human Retina Cells that Express Adenovirus E1A and E1B Proteins)-Derived Clone The $V_H$-$V_L$ sequences of the phage UBS-54 directed against the homotypic adhesion molecule EP-CAM (Huls et al., 1999) was not only cloned into a vector encoding the constant domains of a human IgG1 with Kappa light chain (expression vector pUBS3000Neo), but also into an expression vector encoding the constant domains of a human IgA1 with Kappa light chain (expression vector pUBS54-IgA, FIG. 8). Hence, antibodies derived from pUBS3000Neo and pUBS54-IgA do bind to the same epitope on EPCAM. The only differences antibodies derived from pUBS3000Neo and pUBS54-IgA are in the sequences encoding the constant domains of the heavy chain, resulting in either an IgG1 or IgA1 isotype. The Kappa light chain sequences of these two vectors are identical.

Stable PER.C6® (human retina cells that express adenovirus E1A and E1B proteins)-derived cell lines expressing antibodies encoded by genetic information on pUBS3000Neo and pUBS54-IgA are generated by procedures well known to persons skilled in the art. Therefore, PER.C6® cells (human retina cells that express adenovirus E1A and E1B proteins) are seeded in DMEM plus 10% FBS in tissue culture dishes (10 cm diameter) or T80 flasks with approximately $2.5 \times 10^6$ cells per dish and kept overnight under their normal culture conditions (10% $CO_2$ concentration and 37° C.). The next day, transfections are performed in separate dishes at 37° C. using Lipofectamine (Invitrogen Life Technologies) according to standard protocols provided by the manufacturer, with either 1-2 µg pUBS3000Neo and pUBS54-IgA. As a control for transfection efficiency, a few dishes are transfected with a LacZ control vector, while a few dishes are not transfected and serve as negative controls.

After four to five hours, cells are washed twice with DMEM and given fresh medium without selection. The next day, medium is replaced with fresh medium containing 500 µg/ml G418. Cells are refreshed every two or three days with medium containing the same concentrations of G418. About 20 to 22 days after seeding, a large number of colonies are visible and from each transfection, at least 300 are picked and grown via 96-well plates and/or 24-well plates via 6-well plates to T25 flasks. At this stage, cells are frozen (at least one, but usually four vials per sub-cultured colony) and production levels of recombinant human IgG and human IgA antibody are determined in the supernatant using an ELISA specific for human IgG1 as well as an ELISA specific for human IgA. Also, at this stage, G418 is removed from the culture medium and never re-applied again. For a representative number of colonies, larger volumes are cultured to purify the recombinant human IgG1 and human IgA fraction from the conditioned supernatant using, for instance, a combination of Protein L- or LA-affinity chromatography, cation exchange chromatography, hydrophobic interaction chromatography and gel filtration. Purified human immunoglobulins from the various clones are analyzed on SDS-PAGE, Iso-electric focusing (IEF) and binding to the target EPCAM using cell lines having a high expression of this molecule. The clones will also be screened by PCR on genomic DNA for the presence or absence of pUBS3000Neo and pUBS54-IgA. The identity of the PCR products is further confirmed by DNA sequencing.

A limited number of clones, which are screened positive for the production of both EPCAM IgG1 and EPCAM IgA, are subjected to single cell sorting using a fluorescence-activated cell sorter (FACS) (Becton Dickinson FACS VANTAGE SE™). Alternatively, colonies are seeded at 0.3 cells/well to guarantee clonal outgrowth. Clonal cell populations, hereafter designated as sub-clones, are refreshed once a week with fresh medium. Sub-clones are grown and transferred from 96-well plates via 24- and 6-well plates to T25 flasks. At this stage, sub-clones are frozen (at least one, but usually four vials per sub-clone) and production levels of recombinant human IgG1 and IgA antibody are determined in the supernatant using a human IgG1-specific ELISA and a human IgA-specific ELISA. For a representative number of sub-clones, larger volumes are cultured to purify the recombinant human IgG1 and human IgA1 fraction from the conditioned supernatant using, for instance, a combination of Protein L- or LA-affinity chromatography, cation exchange chromatography, hydrophobic interaction chromatography and gel filtration. Purified human immunoglobulins from the various clones are analyzed on SDS-PAGE, Iso-electric focusing (IEF) and binding to the target EPCAM using cell lines having a high expression of this molecule.

Sub-clones will also be screened by PCR on genomic DNA for the presence or absence of pUBS3000Neo and pUBS54-IgA. The identity of the PCR products is further confirmed by DNA sequencing.

Other methods such as Southern blot and/or FISH may also be used to determine whether both constructs are present in the clonal cell line.

Example 7

Production of a Human IgG1/IgG3 Mixture Against Multiple Targets in a Clonal PER.C6® Cell Line (Human Retina Cells that Express Adenovirus E1A and E1B Proteins)

Phage clone UBS-54 and Clone K53 (FIG. 3) were obtained as described in Example 1. The $V_H$ and $V_L$ of clone UBS-54 was inserted into an expression vector containing the HAVT20 leader sequence and all the coding sequences for the constant domains of a human IgG1 with a Kappa light chain by a method essentially as described (Boel et al., 2000). The resulting plasmid was designated as pUBS3000Neo (FIG. 4). It will be clear that expression vectors containing heavy chain constant domains of any desired isotype can be constructed by routine methods of molecular biology, using the sequences of these regions that are all available in the art. The $V_H$ and $V_L$ sequences of Phage clone K53 are cloned into an expression vector containing the HAVT20 leader sequence and all the coding sequences for the constant domains of a heavy chain of a human IgG3 with a Kappa light chain by a method essentially as described (Boel et al., 2000). This expression vector is designated as pK53IgG3.

These plasmids are transiently expressed, either alone or in combination, in PER.C6® cells (human retina cells that express adenovirus E1A and E1B proteins). In brief, each 80 cm² flask is transfected by incubation for four hours with 140 µl lipofectamine+10 µg DNA (either pUBS3000Neo, pK53IgG3 or 10 µg of both) in serum-free DMEM medium at 37° C. After four hours, this is replaced with DMEM+10% FBS and the cells are grown overnight at 37° C. Cells are then washed with PBS and the medium is replaced with Excell 525 medium (JRH Bioscience). The cells are allowed to grow at 37° C. for six days, after which the cell culture supernatant is harvested. Human IgG-specific ELISA analysis, i.e., measuring all IgG sub-types, is done to determine the IgG concentration in transfected and non-transfected PER.C6® cells (human retina cells that express adenovirus E1A and E1B proteins). Human IgG from each supernatant is subsequently purified using Protein A-affinity chromatography (Hightrap Protein A HP, cat. no. 1-040203) according to standard procedures, following recommendations of the manufacturer (Amersham Biosciences). After elution, samples are concentrated in a Microcon YM30 concentrator (Amicon) and buffer exchanged to 10 mM sodium phosphate, pH 6.7. Samples are analyzed for binding to the targets EPCAM and CD46 using cell lines having a high expression of these molecules such as LS174T cells. Twelve µg of purified IgG, either transiently expressed UBS-54 IgG1, K53 IgG3 or IgG from the cells in which both antibodies were co-transfected, is subsequently analyzed on iso-electric-focusing gels (Serva Pre-cast IEF gels, pH range 3-10, cat. no. 42866). Samples are loaded on the low pH side and, after focusing, stained with colloidal blue. The pI values of the major isoforms for each sample are determined to illustrate whether there has been expression of UBS-54 IgG1, K53 IgG3 or bispecific heterodimers, depending on how the cells were transfected. The identification of heterodimers would indicate that single cells have translated both the IgG3 heavy chain of K53 and the IgG1 heavy chain of UBS-54 and assembled these into a full-length IgG molecule together with the common light chain.

The absence of bispecific heterodimers indicates that it is possible to translate both the IgG3 heavy chain of K53 and the IgG1 heavy chain of UBS-54 in single cells, but that these do not assemble into a full-length IgG molecule together with the common light chain, i.e., there is preferential binding of IgG1 and IgG3 heavy chains. This could, however, also be explained by the lack of co-expression of UBS-54 IgG1 and K53 IgG3. Therefore, stable clonal cell lines expressing both pUBS3000Neo and pK53IgG3 are generated by procedures as such well known to persons skilled in the art. PER.C6® cells (human retina cells that express adenovirus E1A and E1B proteins) are seeded in DMEM plus 10% FBS in tissue culture dishes (10 cm diameter) or T80 flasks with approximately 2.5×10⁶ cells per dish and kept overnight under their normal culture conditions (10% CO₂ concentration and 37° C.). The next day, transfections are performed in separate dishes at 37° C. using Lipofectamine (Invitrogen Life Technologies) according to standard protocols provided by the manufacturer, with either 1-2 µg pUBS3000Neo, pK53IgG3 or both. As a control for transfection efficiency, a few dishes are transfected with a LacZ control vector, while a few dishes will be not transfected and serve as negative controls.

After four to five hours, cells are washed twice with DMEM and given fresh medium without selection. The next day, medium is replaced with fresh medium containing 500 µg/ml G418. Cells are refreshed every two or three days with medium containing the same concentrations of G418. About 20 to 22 days after seeding, a large number of colonies are visible and from each transfection, at least 300 are picked and grown via 96-well plates and/or 24-well plates via 6-well plates to T25 flasks. At this stage, cells are frozen (at least one, but usually four vials per sub-cultured colony) and production levels of recombinant human IgG antibody are determined in the supernatant using an ELISA specific for all sub-types of human IgG. Also, at this stage, G418 is removed from the culture medium and never re-applied again. For a representative number of colonies, larger volumes are cultured to purify the recombinant human IgG from the conditioned supernatant using Protein A-affinity chromatography (Hightrap Protein A HP, cat. no. 1-040203) according to standard procedures, following recommendations of the manufacturer (Amersham Biosciences). Purified human immunoglobulins from the various clones are analyzed on SDS-PAGE, Iso-electric focusing (IEF) and binding to the targets EPCAM and CD46 using cell lines having a high expression of these molecules such as LS174T cells. The clones are also screened by PCR on genomic DNA for the presence or absence of pUBS3000Neo and pK53IgG3. The identity of the PCR products is further confirmed by DNA sequencing.

A limited number of clones, which are screened positive for the production of both EPCAM IgG1 and K53 IgG3, are subjected to single cell sorting using a fluorescence-activated cell sorter (FACS) (Becton Dickinson FACS VANTAGE SE™). Alternatively, colonies are seeded at 0.3 cells/well to guarantee clonal outgrowth. Clonal cell populations, hereafter designated as sub-clones, are refreshed once a week with fresh medium. Sub-clones are grown and transferred from 96-well plates via 24- and 6-well plates to T25 flasks. At this stage, sub-clones are frozen (at least one, but usually four vials per sub-clone) and production levels of recombinant human IgG antibody are determined in the supernatant using a human IgG-specific ELISA. For a representative number of sub-clones, larger volumes are cultured to purify the recombinant human IgG fraction from the conditioned supernatant using Protein A-affinity chromatography (Hightrap Protein A HP, cat. no. 1-040203) according to standard procedures, following recommendations of the manufacturer (Amersham Biosciences). Purified human immunoglobulins from the various clones are analyzed on SDS-PAGE, Iso-electric focusing (IEF) and binding to the targets EPCAM and CD46 using cell lines having a high expression of this molecules, such as, for instance, LS174T cells, or transfectants expressing these molecules.

Sub-clones are also screened by PCR on genomic DNA for the presence or absence of pUBS3000Neo and pK53IgG3. The identity of the PCR products is further confirmed by DNA sequencing.

Other methods such as Southern blot and/or FISH may also be used to determine whether both constructs are present in the clonal cell line.

Once the clonal sub-clones are available and confirmed positive for the expression of both UBS-54 IgG1 and K53 IgG3, the presence of functional K53 and UBS-54 shows that it is possible to generate a mixture of functional IgGs with different isotypes with the common light chain in a single cell. Analysis of the expression of bispecific antibodies binding both EpCAM and CD46 will reveal to what extent the different heavy chains having a different sub-type will pair, which will influence the amount of bispecific antibodies produced. It is expected that no or very low levels of bispecific antibodies will be found in this case.

Example 8

Selection of Phage Carrying Single Chain Fv Fragments Specifically Recognizing Rabies Virus Glyco Protein (RVGP) Using RVGP-Ig Fusion Protein, and Expression of Mixtures of Antibodies Against the Rabies Virus This example describes the production of mixtures of antibodies against the rabies virus as another potential target. As an antigen, the Rabies Virus Glycoprotein (RVGP) is chosen, but other rabies antigens may be chosen or included as well for this purpose. Several monoclonal antibodies recognizing RVGP have already been described in the art, and polyclonal antibodies have been recognized to be useful in treatment of rabies infections as well (e.g., EP0402029; EP0445625, the entirety of which are incorporated herein by reference).

Antibody fragments are selected using antibody phage display libraries and MAbstract™ technology, essentially as described in U.S. Pat. No. 6,265,150 and in WO 98/15833, the entirety of which is incorporated herein by reference. All procedures are performed at room temperature unless stated otherwise. The sequence of RVGP is available to one of ordinary skill in the art for cloning purposes (e.g., Yelverton et al., 1983, the entirety of which is incorporated herein by reference). An RVGP-Ig fusion protein consisting of whole RVGP fused genetically to the CH2 and CH3 domains of human IgG1 is produced using vector pcDNA3.1 Zeo-CH2-CH3 expressed in PER.C6® (human retina cells that express adenovirus E1A and E1B proteins) and coated for two hours at 37° C. onto the surface of MAXISORP™ (polystyrene based modified surface with a high affinity for polar groups) plastic tubes (Nunc) at a concentration of 1.25 µg/ml. The tubes are blocked for one hour in 2% fat-free milk powder dissolved in PBS (MPBS). Simultaneously, 500 µl (approximately $10^{13}$ cfu) of a phage display library expressing single chain Fv fragments (scFvs) essentially prepared as described by De Kruif et al. (1995a, b) and references therein, is added to two volumes of 4% MPBS. In this experiment, selections are performed using fractions of the original library constructed using only one single variable light chain gene species (e.g., a "Vκ1"-library). In addition, human serum is added to a final concentration of 15% and blocking is allowed to proceed for 30 to 60 minutes. The RVGP-Ig-coated tubes are emptied and the blocked phage library is added. The tube is sealed and rotated slowly for one hour, followed by two hours of incubation without rotation. The tubes are emptied and washed ten times in PBS containing 0.1% Tween-20, followed by washing five times in PBS. One ml glycine-HCL, 0.05 M, pH 2.2 is added, and the tube is rotated slowly for ten minutes. The eluted phages are added to 500 µl 1 M Tris-HCl pH 7.4. To this mixture, 3.5 ml of exponentially growing XL-1 blue bacterial culture is added. The tubes are incubated for 30 minutes at 37° C. without shaking. Then, the bacteria are plated on 2TY agar plates containing ampicillin, tetracycline and glucose. After overnight incubation of the plates at 37° C., the colonies are scraped from the plates and used to prepare an enriched phage library, essentially as described by De Kruif et al. (1995a, b). Briefly, scraped bacteria are used to inoculate 2TY medium containing ampicillin, tetracycline and glucose and grown at a temperature of 37° C. to an $OD_{600nm}$ of ~0.3. Helper phages are added and allowed to infect the bacteria, after which the medium is changed to 2TY containing ampicillin, tetracycline and kanamycin. Incubation is continued overnight at 30° C. The next day, the bacteria are removed from the 2TY medium by centrifugation, after which the phages are precipitated using polyethylene glycol 6000/NaCl. Finally, the phages are dissolved in a small volume of PBS-1% BSA, filter-sterilized and used for a next round of selection. The selection/re-infection procedure is performed twice.

After the second round of selection, individual E. coli colonies are used to prepare monoclonal phage antibodies. Essentially, individual colonies are grown to log-phase and infected with helper phages, after which phage antibody production is allowed to proceed overnight. Phage antibody-containing supernatants are tested in ELISA for binding activity to human RVGP-Ig coated 96-well plates.

Selected phage antibodies that are obtained in the screen described above are validated in ELISA for specificity. For this purpose, human RVGP-Ig is coated to Maxisorp ELISA plates. After coating, the plates are blocked in 2% MPBS. The selected phage antibodies are incubated in an equal volume of 4% MPBS. The plates are emptied, washed once in PBS, after which the blocked phages are added. Incubation is allowed to proceed for one hour, the plates are washed in PBS 0.1% Tween-20 and bound phages are detected using an anti-M13 antibody conjugated to peroxidase. As a control, the procedure is performed simultaneously using a control phage antibody directed against thyroglobulin (De Kruif et al. 1995a, b), which serves as a negative control.

The phage antibodies that bind to human RVGP-Ig are subsequently tested for binding to human serum IgG to exclude the possibility that they recognized the Fc part of the fusion protein.

In another assay, the phage antibodies are analyzed for their ability to bind PER.C6® cells (human retina cells that express adenovirus E1A and E1B proteins) that express RVGP. To this purpose, PER.C6® cells (human retina cells that express adenovirus E1A and E1B proteins) are transfected with a plasmid carrying a cDNA sequence encoding RVGP or with the empty vector and stable transfectants are selected using standard techniques known to a person skilled in the art (e.g., J. E. Coligan et al. (2001), *Current Protocols In Protein Science*, volume I, John Wiley & Sons, Inc. New York, the entirety of which is incorporated herein by reference). For flow cytometry analysis, phage antibodies are first blocked in an equal volume of 4% MPBS for 15 minutes at 4° C. prior to the staining of the RVGP- and control-transfected PER.C6® cells (human retina cells that express adenovirus E1A and E1B proteins). The blocked phages are added to a mixture of unlabeled control-transfected PER.C6® cells (human retina cells that express adenovirus E1A and E1B proteins) and RGVP-transfected PER.C6® cells that have been labeled green using a lipophylic dye (PKH67, Sigma). The binding of the phage antibodies to the cells is visualized using a biotinylated anti-M13 antibody (Santa Cruz Biotechnology), followed by streptavidin-phycoerythrin (Caltag). Anti RVGP scFv selectively stains the PER.C6® RVGP transfectant while they do not bind the control transfectant.

An alternative way of screening for phages carrying single chain Fv fragments specifically recognizing human RVGP, is by use of RVGP-transfected PER.C6® cells (human retina cells that express adenovirus E1A and E1B proteins).

PER.C6® cells (human retina cells that express adenovirus E1A and E1B proteins) expressing membrane-bound RVGP are produced as described supra. Phage selection experiments are performed as described supra, using these cells as target. A fraction of the phage library comprised of scFv phage particles using only one single scFv species (500 μl, approximately $10^{13}$ cfu) is blocked with 2 ml RPMI/10% FCS/1% NHS for 15 minutes at RT. Untransfected PER.C6® cells (human retina cells that express adenovirus E1A and E1B proteins) (~$10\times10^6$ cells) are added to the PER.C6-RVGP cells (~$1.0\times10^6$ cells). This mixture is added to the blocked light chain restricted phage library and incubated for 2.5 hours while slowly rotating at 4° C. Subsequently, the cells are washed twice and were resuspended in 500 μl RPMI/10% FCS and incubated with a murine anti-RVGP antibody (Becton Dickinson) followed by a phycoerythrin (PE)-conjugated anti-mouse-IgG antibody (Caltag) for 15 minutes on ice. The cells are washed once and transferred to a 4 ml tube. Cell sorting is performed on a FACSvantage fluorescence-activated cell sorter (Becton Dickinson) and RVGP (PE positive) cells are sorted. The sorted cells are spun down, the supernatant is saved and the bound phages are eluted from the cells by resuspending the cells in 500 μl 50 mM Glycin pH2.2 followed by incubation for five minutes at room temperature. The mixture is neutralized with 250 μl 1 M Tris-HCl pH 7.4 and added to the rescued supernatant. Collectively, these phages are used to prepare an enriched phage library as described above. The selection/re-infection procedure is performed twice. After the second round of selection, monoclonal phage antibodies are prepared and tested for binding to RVGP-PER.C6® cells and untransfected PER.C6® cells (human retina cells that express adenovirus E1A and E1B proteins) as described supra. Phages that are positive on RVGP-transfected cells are subsequently tested for binding to the RVGP-IgG fusion protein in ELISA as described supra.

The selected scFv fragments are cloned in a human IgG1 format, according to methods known in the art (e.g., Boel et al., 2000). To this purpose, the $V_L$ fragment shared by the selected scFv is PCR amplified using oligos that add appropriate restriction sites. A similar procedure is used for the $V_H$ genes. Thus, modified genes are cloned in expression pCRU-K01 (ECACC deposit 03041601), which results in expression vectors encoding a complete huIgG1 heavy chain and a complete human light chain gene having the same specificity as the original phage clone. By this method, three different heavy chains are cloned into separate expression vectors, while only one of the vectors needs to comprise the common light chain sequence. These expression vectors are provisionally designated pCRU-RVGP-1, pCU-RVGP-2, and pCRU-RVGP-3. Alternatively, these three vectors may lack DNA encoding the $V_L$ region, which can then be encoded in a fourth, separate expression vector not encoding a heavy chain. It is also possible to have $V_L$ sequences present in all three or two of the three vectors comprising the different $V_H$ sequences.

Stable PER.C6® (human retina cells that express adenovirus E1A and E1B proteins)-derived cell lines are generated, according to methods known to one of ordinary skill in the art (see, e.g., WO 00/63403), the cell lines expressing antibodies encoded by genetic information on either pCRU-RVGP-1, pCRU-RVGP-2 or pCRU-RVGP-3 and a cell line expressing antibodies encoded by all three plasmids. Therefore, PER.C6® cells are seeded in DMEM plus 10% FBS in tissue culture dishes (10 cm diameter) or T80 flasks with approximately $2.5\times10^6$ cells per dish and kept overnight under their normal culture conditions (10% $CO_2$ concentration and 37° C.). The next day, transfections are performed in separate dishes at 37° C. using Lipofectamine (Invitrogen Life Technologies) according to standard protocols provided by the manufacturer, with either 1-2 μg pCRU-RVGP-1, 1-2 μg pCRU-RVGP-2, 1-2 μg pCRU-RVGP-3 or 1 μg of a mixture of pCRU-RVGP-1, pCRU-RVGP-2 and pCRU-RVGP-3. As a control for transfection efficiency, a few dishes are transfected with a LacZ control vector, while a few dishes will not be transfected and serve as negative controls.

After four to five hours, cells are washed twice with DMEM and given fresh medium without selection. The next day, the medium is replaced with fresh medium containing 500 μg/ml G418. Cells are refreshed every two or three days with medium containing the same concentrations of G418. About 20 to 22 days after seeding, a large number of colonies are visible and from each transfection, at least 300 are picked and grown via 96-well plates and/or 24-well plates via 6-well plates to T25 flasks. At this stage, cells are frozen (at least one, but usually four vials per sub-cultured colony) and production levels of recombinant human IgG antibody are determined in the supernatant using an ELISA specific for human IgG1 (described in WO 00/63403). Also, at this stage, G418 is removed from the culture medium and never re-applied again. For a representative number of colonies, larger volumes will be cultured to purify the recombinant human IgG1 fraction from the conditioned supernatant using Protein A-affinity chromatography according to standard procedures. Purified human IgG1 from the various clones is analyzed on SDS-PAGE, Iso-electric focusing (IEF) and binding to the target RVGP using an RVGP PER.C6-transfectant described above.

Colonies obtained from the co-transfection with pCRU-RVGP-1, pCRU-RVGP-2 and pCRU-RVGP-3 are screened by PCR on genomic DNA for the presence or absence of each of the three constructs. The identity of the PCR products is further confirmed by DNA sequencing.

A limited number of colonies, which screened positive for the production of each of the three binding specificities (both by PCR at the DNA level as well as in the specified binding assays against RVGP), are subjected to single cell sorting using a fluorescence-activated cell sorter (FACS) (Becton & Dickinson FACS VANTAGE SE™).

Alternatively, colonies are seeded at 0.3 cells/well to guarantee clonal outgrowth. Clonal cell populations, hereafter designated as sub-clones, are refreshed once a week with fresh medium. Sub-clones are grown and transferred from 96-well plates via 24- and 6-well plates to T25 flasks. At this stage, sub-clones are frozen (at least one, but usually four vials per sub-clone) and production levels of recombinant human IgG1 antibody are determined in the supernatant using a human IgG1-specific ELISA. For a representative number of sub-clones, larger volumes are cultured to purify the recombinant human IgG1 fraction from the conditioned supernatant using Protein A-affinity chromatography according to standard procedures.

Purified human IgG1 from the various sub-clones is subsequently analyzed as described above for human IgG1 obtained from the parental clones, i.e., by SDS-PAGE, Iso-electric focusing (IEF) and binding to the target RVGP.

Sub-clones are also screened by PCR on genomic DNA for the presence or absence of each of the three constructs pCRU-RVGP-1, pCRU-RVGP-2 and pCRU-RVGP-3. The identity of the PCR products is further confirmed by DNA sequencing.

Other methods such as Southern blot and/or FISH can also be used to determine whether each of the three constructs are present in the clonal cell line.

Sub-clones that are proven to be transgenic for each of the three constructs are brought into culture for an extensive period to determine whether the presence of the transgenes is stable and whether expression of the antibody mixture remains the same, not only in terms of expression levels, but also for the ratio between the various antibody isoforms that are secreted from the cell. Therefore, the sub-clone culture is maintained for at least 25 population doubling times, either as an adherent culture or as a suspension culture. At every four to six population doublings, a specific production test is performed using the human IgG-specific ELISA and larger volumes are cultured to obtain the cell pellet and the supernatant. The cell pellet is used to assess the presence of the three constructs in the genomic DNA, either via PCR, Southern blot and/or FISH. The supernatant is used to purify the recombinant human IgG1 fraction as described supra. Purified human IgG1 obtained at the various population doublings is analyzed as described, i.e., by SDS-PAGE, Iso-electric focusing (IEF) and binding to the target RVGP.

The efficacy of the antibody mixtures against rabies is tested in in vitro cell culture assays where the decrease in spread of rabies virus is measured, as well as in in vivo animal models infected by rabies. Such models are known to one of ordinary skill in the art and are, e.g., described in EP0402029.

Example 9

Production of a Mixture of Antibodies with a Common Light Chain and Three Different Heavy Chain-Variable Regions in a Single Cell A method for producing a mixture of antibodies according to the invention using expression in a recombinant host cell of a single light chain and three different heavy chains capable of pairing to the single light chain to form functional antibodies, is exemplified herein and is schematically shown in FIG. 6.

Human IgGs UBS54 and K53 against the EP-CAM homotypic adhesion molecule (Huls et al., 1999) and the membrane cofactor protein CD46 (WO 02/18948), respectively, are described in Example 1. Another clone that was identified to bind to cofactor protein CD46 was clone 02-237 (sequence of $V_H$ provided in FIG. 12, SEQ ID NO:10). DNA sequencing of this clone revealed that it contained the same light chain as UBS54 and K53 but a unique heavy chain-variable sequence (see alignment in FIG. 3). As a result, the CDR3 of the heavy chain of 02-237 differs at four positions from that of K53 (see alignment in FIG. 13). The heavy and light chain-variable sequences of phage 02-237 were cloned into the expression plasmid pCRU-K91 (pCRU-K01 is deposited at the European Collection of Cell Cultures (ECACC) under number 03041601), which contains the heavy and light chain constant domains for an IgG1 antibody.

The resulting plasmid was designated pgG102-237. Due to the cloning strategy followed, the resulting N-terminus of the light chain of 02-237 as encoded by pgG102-237 differed slightly from the N-terminus of UBS54 and K53 as present by pUBS3000Neo, pCD46_3000(Neo), respectively (FIG. 3). Plasmid pgG102-237 was transiently produced in human 293 (T) cells or stably in PER.C6® cells (human retina cells that express adenovirus E1A and E1B proteins). It appeared that purified 02-237 IgG had a much higher affinity for purified CD46 (FIG. 14) than K53 IgG, i.e., the affinity had increased from $9.1\times10^{-7}$ M to $2.2\times10^{-8}$ M for K53 and 02-237, respectively. Also, 02-237 bound much better to CD46 on human coloncarcinoma LS174T cells than K53 (FIG. 15).

Stable PER.C6® (human retina cells that express adenovirus E1A and E1B proteins)-derived cell lines expressing a combination of the plasmids pUBS3000Neo, pCD46_3000 (Neo) and pgG102-237 encoding human IgG 02-237 were generated according to methods known as such to one of ordinary skill in the art (see, e.g., WO 00/63403). Therefore, PER.C6® cells (human retina cells that express adenovirus E1A and E1B proteins) were seeded in DMEM plus 10% FBS in tissue culture dishes (10 cm diameter) with approximately $2.5\times10^6$ cells per dish and kept overnight under their normal culture conditions (10% $CO_2$ concentration and 37° C.). The next day, transfections were performed in separate dishes at 37° C. using Lipofectamine (Invitrogen Life Technologies) according to standard protocols provided by the manufacturer, with 2 μg of an equimolar mixture of pUBS3000Neo, pCD46_3000(Neo) and pgG102-237. As negative control for selection, a few dishes were not transfected.

After four to five hours, cells were washed twice with DMEM and given fresh medium without selection. The next day, medium was replaced with fresh medium containing 500 μg/ml G418. Cells were refreshed every two or three days with medium containing the same concentrations of G418. About 20 to 22 days after seeding, a large number of colonies were visible and about 300 were picked and grown via 96-well plates and/or 24-well plates via 6-well plates to T25 flasks. During sub-culturing, production levels of recombinant human IgG antibody were determined in the supernatant using an ELISA specific for human IgG1 (described in WO 00/63403). About 25% of all colonies appeared to be positive in this highly specific assay. The production levels measured at this stage were comparable to the levels when a single IgG is expressed in PER.C6® cells (human retina cells that express adenovirus E1A and E1B proteins) (expression of a single IgG described in Jones et al., 2003). It is important to stress that these high expression levels were obtained without any methods for amplification of the transgene and that they occur at a low copy number of the transgene.

The 30 best producing colonies were frozen down in vials and the 19 highest producing clones were selected for purification of the IgG (Table 1). They were sub-cultured in T80 flasks and human IgG from each clone was subsequently purified using Protein A-affinity chromatography. Therefore, 15 to 25 ml of conditioned medium was loaded on a 5 ml Protein A FF Sepharose column (Amersham Biosciences). The column was washed with 4 mM phosphate buffered saline, pH 7.4 (PBS) before elution with 0.1 M citrate pH 3.0. The eluted fraction was subsequently desalted on a Sephadex G25 Fine HiPrep Desalting column (Amersham Biotech) to PBS. The concentration of the purified IgG fraction was determined by absorbance measurement at 280 nm using a coefficient of 1.4 for a 0.1% (w/v) solution (Table 1).

Figure 16A:
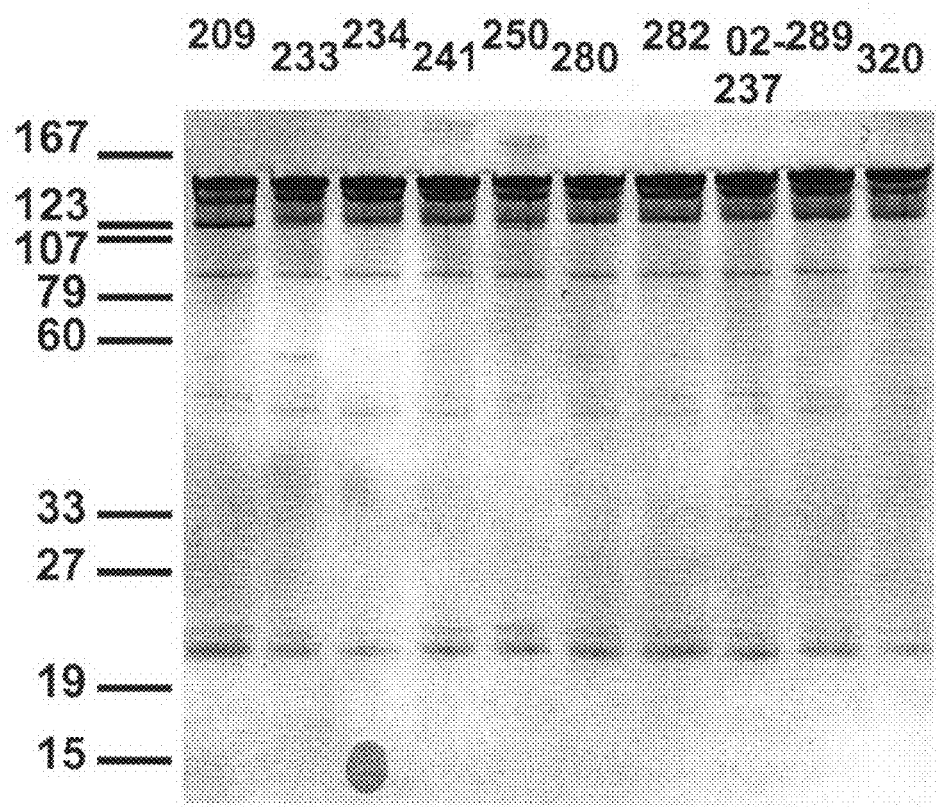
FIG. 16A is an SDS-PAGE analysis of purified IgG fractions. Three μg purified IgG was analyzed on a non-reduced 4-20% NUPAGE® gel (Novex) according to recommendations of the manufacturer. Proteins were visualized by staining with colloidal blue (Novex Cat. No LC6025) according to recommendations of the manufacturer. Clone identity is indicated on top of the SDS-PAGE. Each gel contains a control, which is either purified 02-237 or K53.
Figure 16B:
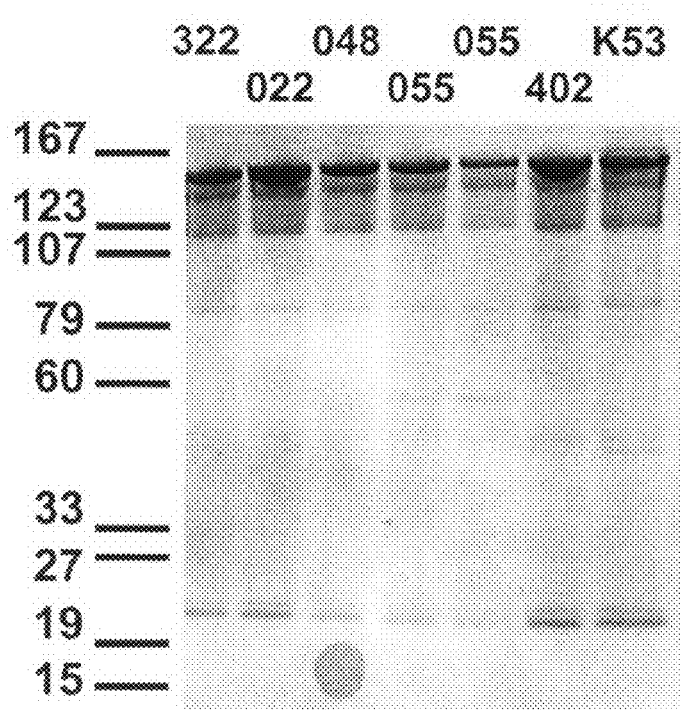
FIGS. 16B and 16C are continuations of the gel in FIG. 16A.
Figure 16C:
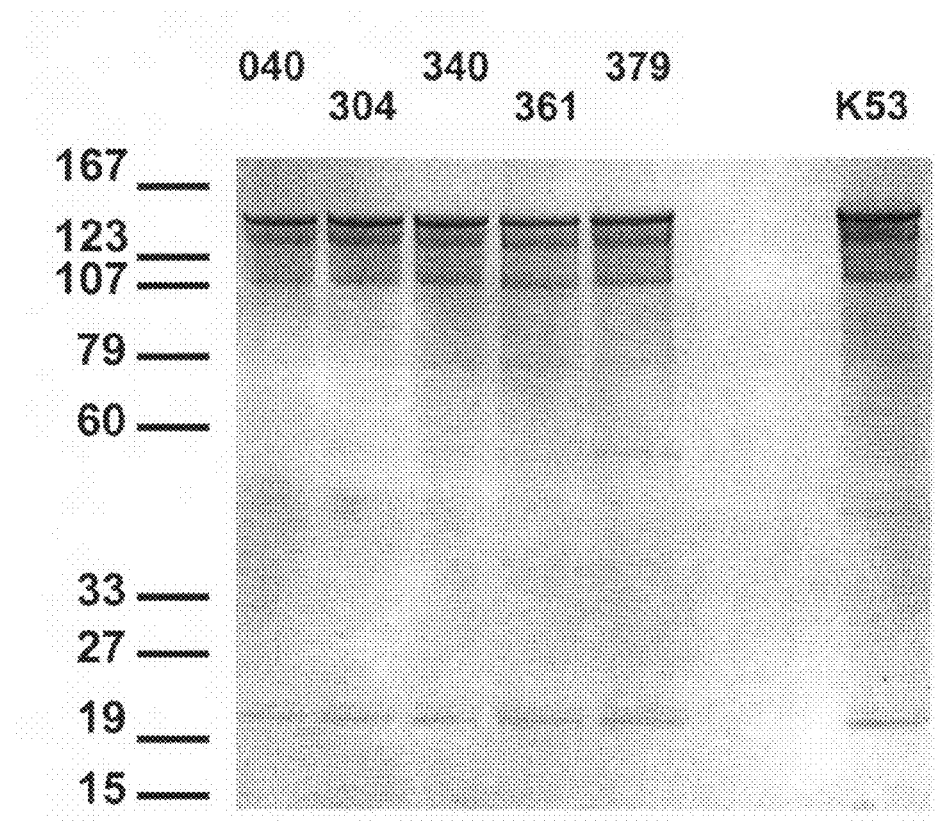
Figure 16D:
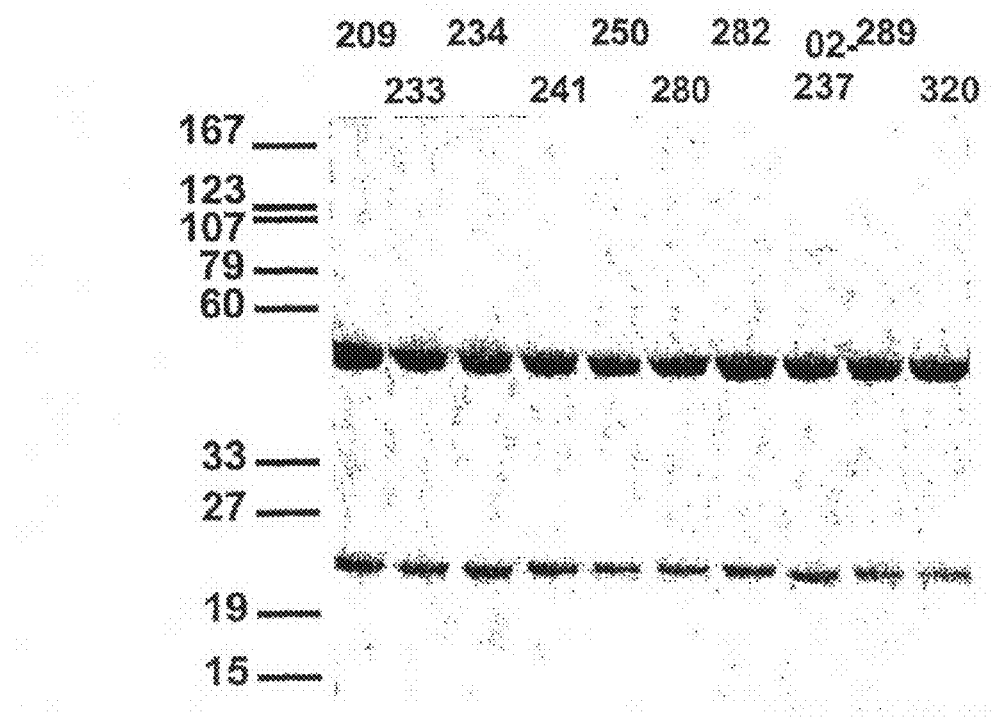
FIG. 16D is an SDS-PAGE analysis of purified IgG fractions. Three μg purified IgG was analyzed on a reduced 4-20% NUPAGE® gel according to recommendations of the manufacturer. Proteins were visualized by staining with colloidal blue (Novex cat. No LC6025) according to recommendations of the manufacturer. Clone identity is indicated on top of the SDS-PAGE. Each gel contains a control, which is either purified 02-237 or K53. NR, Non-reduced; R, reduced.
Figure 16E:
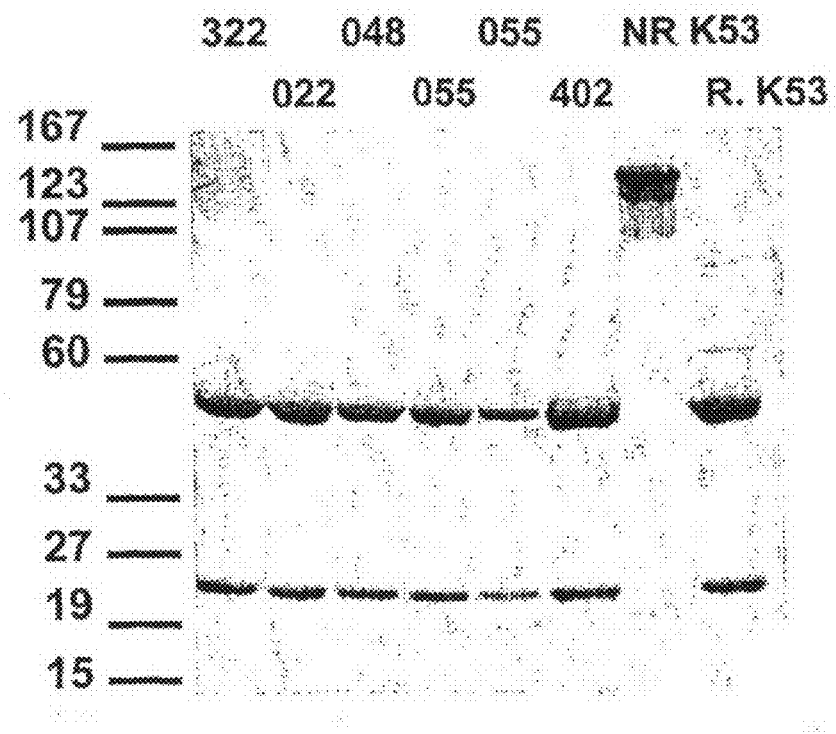
FIGS. 16E and 16F are continuations of the gel in FIG. 16D.
Figure 16F:
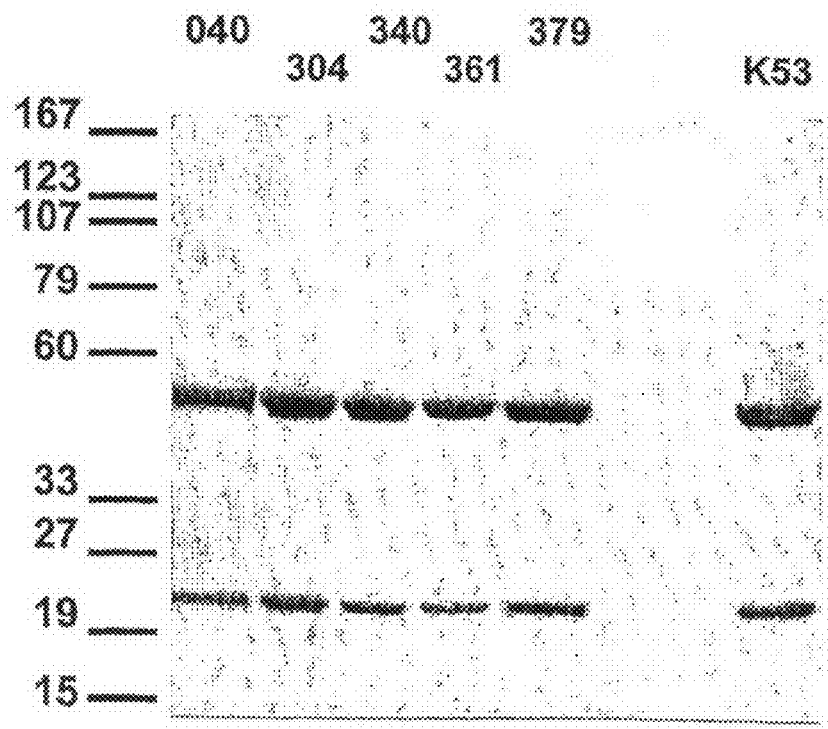
Figure 17A:
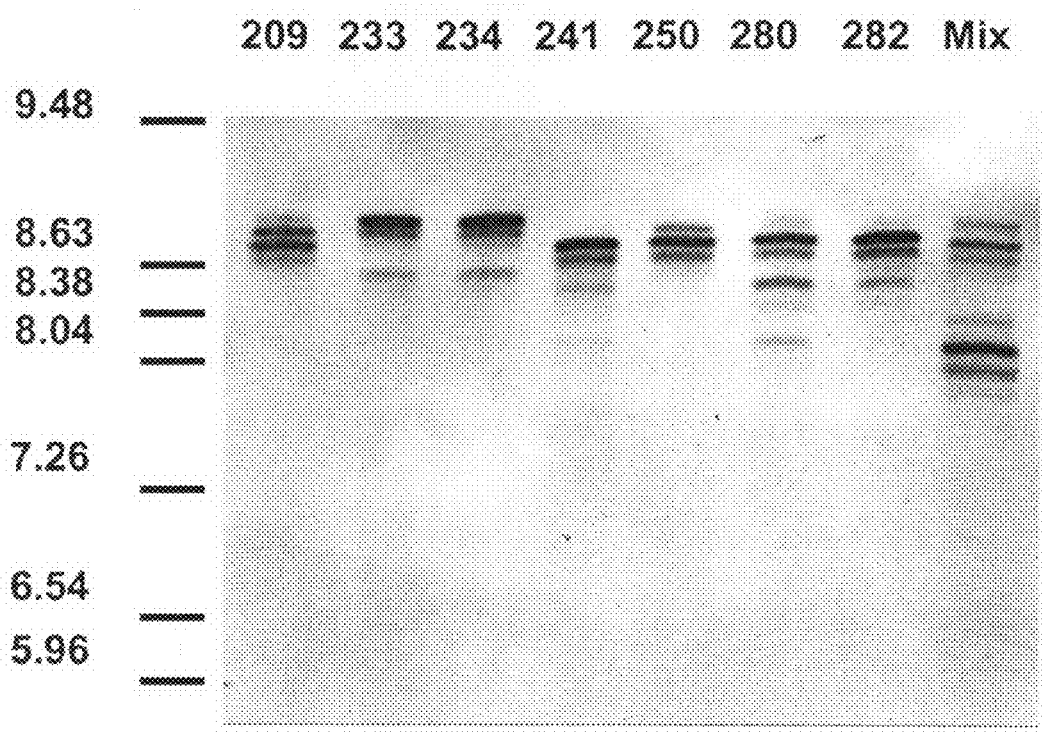
FIG. 17A shows an IEF analysis of purified IgG fractions. Ten μg purified IgG was analyzed on an Isogel 3-10 gel (BMA) according to recommendations of the manufacturer. Proteins were visualized by staining with colloidal blue according to recommendations of the manufacturer. Clone identity is indicated on top of the IEF. Each gel contains a control, consisting of a 1:1:1 mixture of 02-237, K53 and UBS54.
Figure 17B:
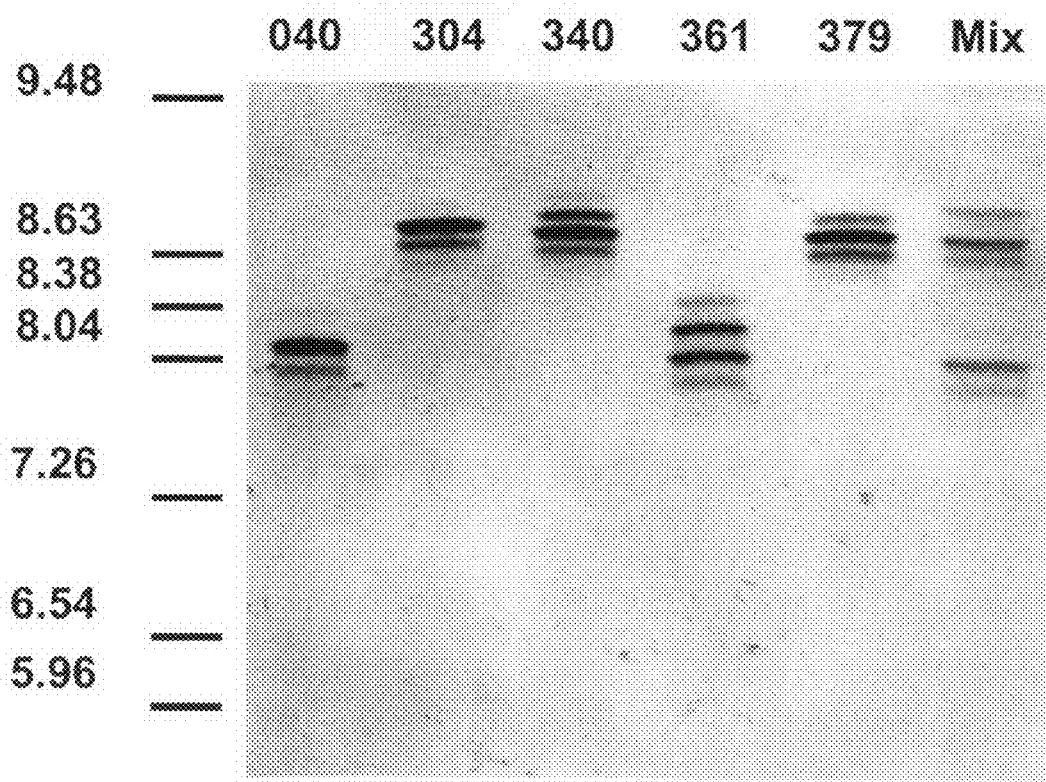
FIGS. 17B through 17D are continuations of the gel in FIG. 17A.
Figure 17C:
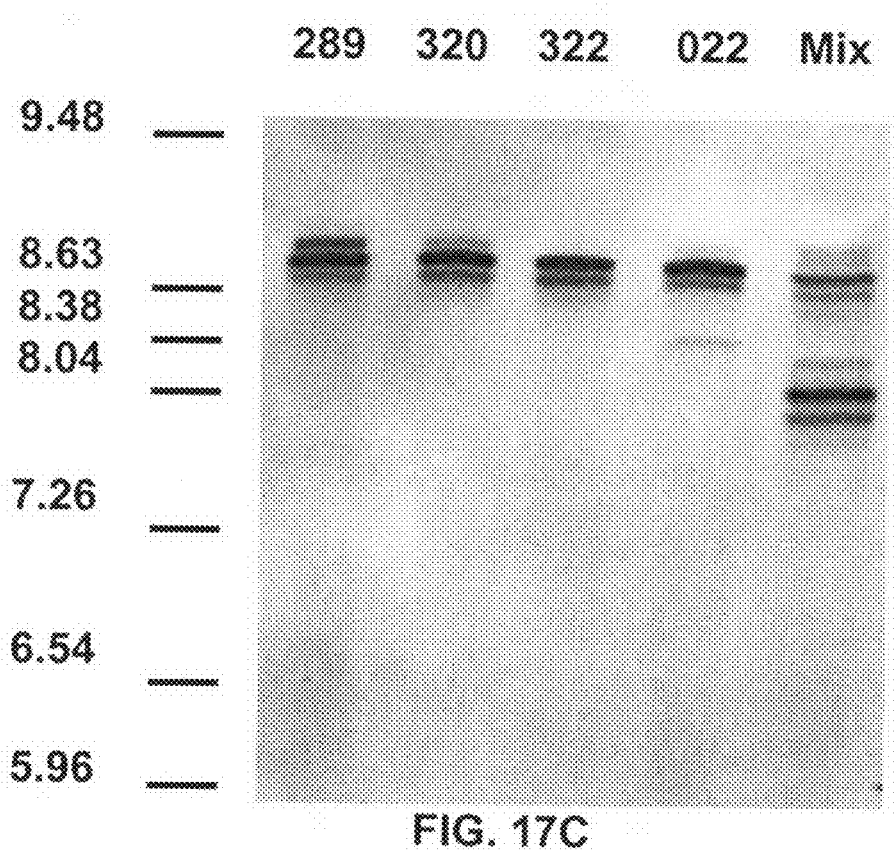
Figure 17D:
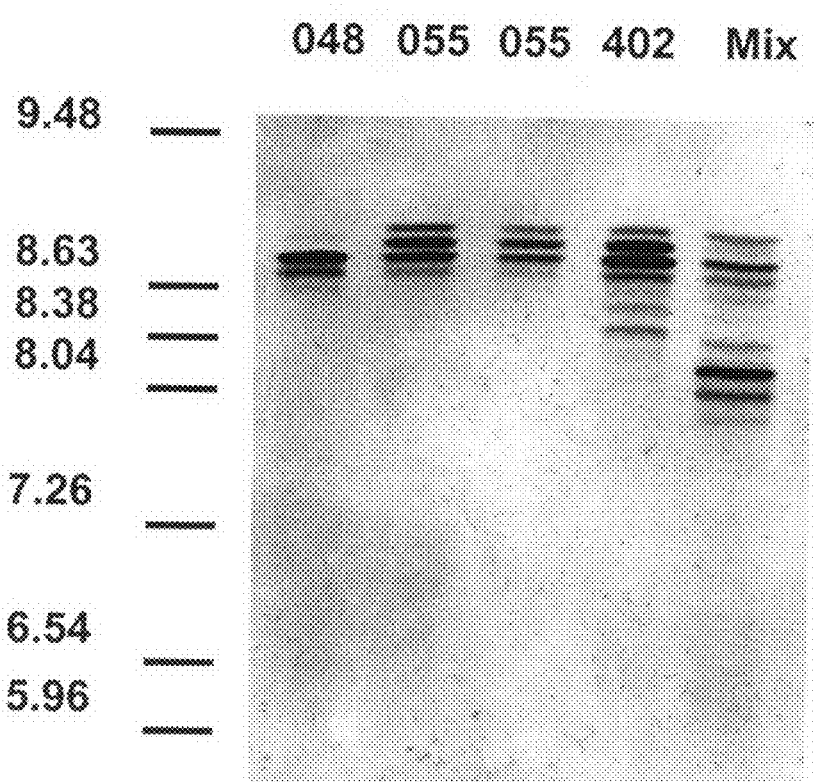

The purified IgG samples were analyzed on non-reduced and reduced SDS-PAGE and IEF. Non-reduced SDS-PAGE (FIG. 16A) showed that all IgG samples migrated comparable to the control K53 or 02-237 as an assembled, intact IgG molecule of approximately 150 kDa. On reduced SDS-PAGE (FIG. 16B), the IgG samples migrated as heavy and light chains of about 50 and 25 kDa, respectively, comparable to the heavy and light chain of the control K53 or 02-237.

Figure 18:
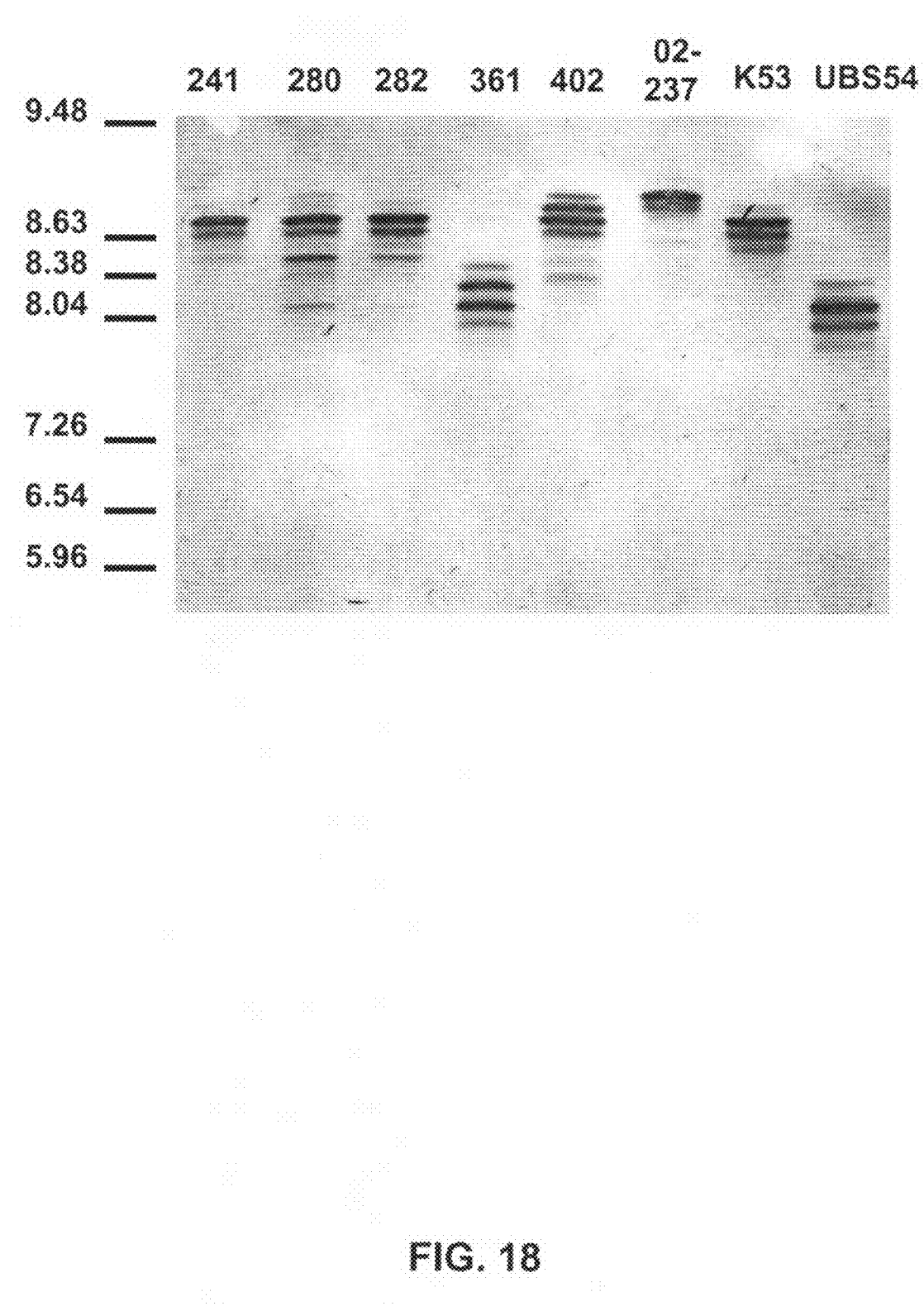
FIG. 18 is an IEF analysis of polyclonal mixtures 241, 280, 282, 361 and 402 in comparison to single K53, 02-237 and UBS54. Ten μg purified IgG was analyzed on an Isogel 3-10 gel (BMA) according to recommendations of the manufacturer. Proteins were visualized by staining with colloidal blue according to recommendations of the manufacturer. IgG identity is indicated on top of the IEF.

On IEF, the purified IgG fractions were first compared to a mixture of equal amounts of K53, UBS54 and 02-237 (FIG. 17). Clearly, some of the samples contained isoforms with a unique pI profile when compared to the mixture containing purified K53, UBS54 and 02-237. Some major unique isoforms have a pI in between the pI of K53 and 02-237 on one hand and UBS54 on the other hand. This is also anticipated on the basis of the theoretic pI when calculated with the Prot-Param tool provided on the Expasy homepage (expasy.ch; Appel et al., 1994). K53, 02-237 and UBS54 have a theoretic pI of 8.24, 8.36 and 7.65, respectively, whereas an isoform representing a heterodimer of one UBS54 heavy chain and one K53 heavy chain, has a theoretical pI of 8.01. Assembly of such a heterodimer can only occur when a single cell translates both the heavy chain of K53 and the heavy chain of UBS54 and assembles these into a full-length IgG molecule together with the common light chain. Hence, these results suggest that certain clones at least express two functional antibodies. To confirm the unique identity of some of the isoforms, samples of the most interesting clones were run in parallel with K53, UBS54 and 02-237, either alone or in a mixture (FIG. 18). This furthermore showed that some clones expressed at least two antibodies (241, 282, 361). Moreover, it provided evidence that some clones express all three functional antibodies (280 and 402).

To confirm that the clones expressed IgG mixtures comprising all three heavy chains, peptide mapping (Garnick, 1992; Gelpí, 1995, the entirety of which are incorporated herein by reference) was used to analyze the polyclonal IgG fraction. We previously employed peptide mapping to recover 99% of the protein sequence of K53.

Figure 19:
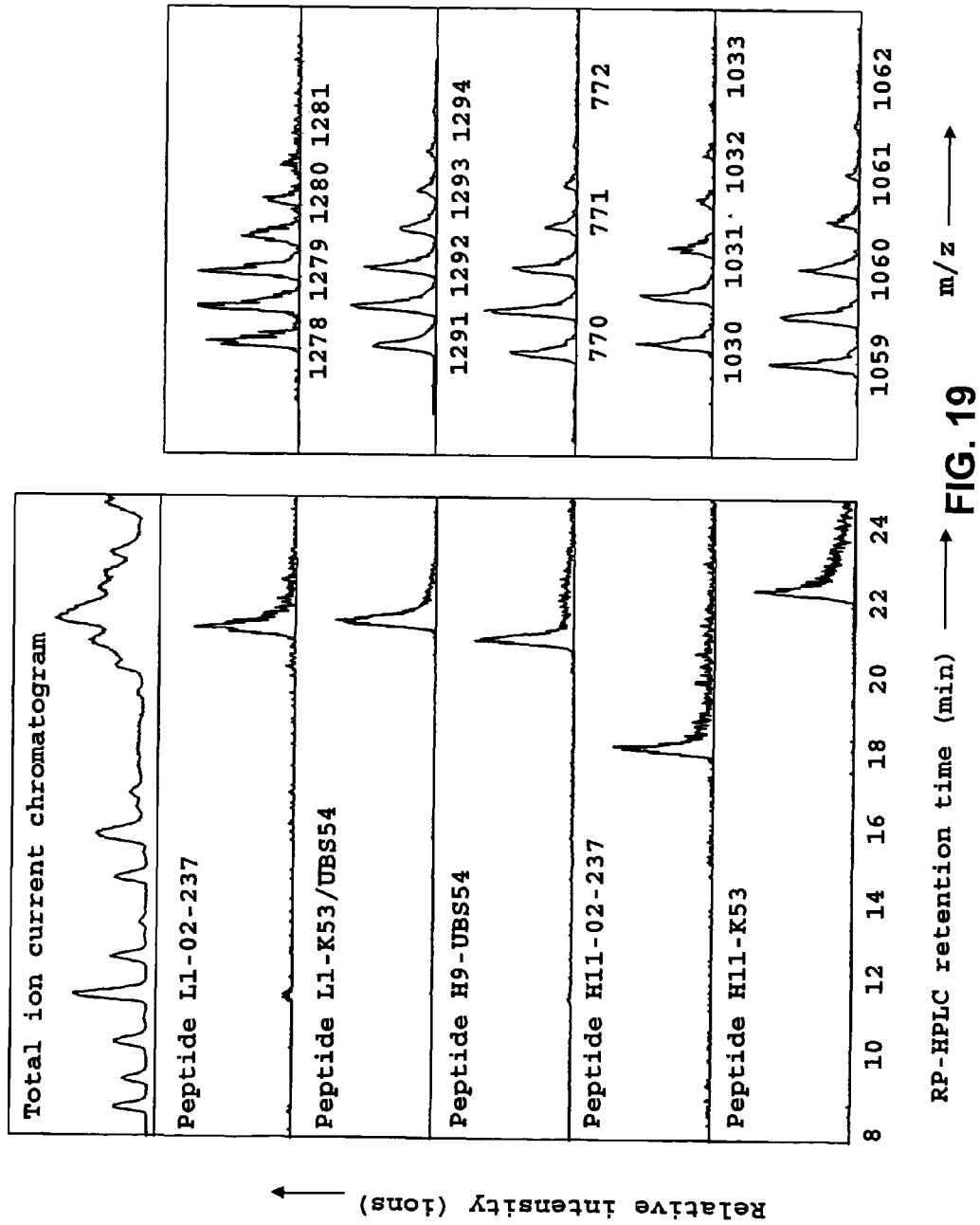
FIG. 19 contains mass chromatograms of CDR3 peptides of K53, 02-237, UBS54 and the two unique light chain peptides L1-K53/UBS54 and L1-237 in IgG fraction Poly1-280. On the right-hand side of each mass chromatogram, the isotopic pattern of the peptide is shown. The doubly charged ion at m/z 1058.98 (Mw 2115.96 Da) results from peptide H11-K53. The doubly charged ion at m/z 1029.96 (Mw 2057.92 Da) results from peptide H11-02-237. The triply charged ion at m/z 770.03 (Mw 2307.09 Da) results from peptide H9-UBS54. The doubly charged ion at m/z 1291.08 (Mw 2580.16 Da) results from peptide L1-K53/UBS54. The doubly charged ion at m/z 1278.11 (Mw 2554.22 Da) results from peptide L1-02-237.

Based on the protein sequence provided in FIG. 12, the mass of the theoretical tryptic peptides of K53, UBS54 and 02-237 was calculated (Table II and III). A few unique peptides for each IgG could be identified, for instance, the CDR3 peptides for K53, 02-237 and UBS54 with a Mw of 2116.05, 2057.99 and 2307.15 Da, respectively. Next, a tryptic digest of Poly1-280 was prepared and this was analyzed using LC-MS (FIG. 19).

Peptides with Mw of 2116, 2057 and 2308 Da, representing the unique CDR3 peptides of K53, 02-237 and UBS54, respectively, were detected. The precise amino acid sequence of these peptides (as listed in Table III) was confirmed by MS-MS analysis (Tables IV, V and VI). The presence of the two unique N-terminal light chain peptides with Mw of 2580 and 2554 Da, respectively, was also confirmed. The peptide mapping data unequivocally showed that a mixture of antibodies comprising a common light chain and three different heavy chains was expressed by PER.C6® (human retina cells that express adenovirus E1A and E1B proteins) clone Poly1-280. Also, clones 055, 241 and 402 were screened by peptide mapping. Clones 241 and 402 were confirmed positive for all three heavy chain sequences, whereas clone 055 only showed expression of the heavy chains of K53 and 02-237, and not of UBS54. This confirms the IEF screening (FIG. 18) where no UBS54-related band was seen in sample 055.

Poly1-280 was analyzed by BIACORE™ (surface plasmon resonance) for binding to CD46 (FIG. 20). The affinity of poly1-280 for CD46 was $2.1 \times 10^{-8}$ M, which shows that the IgG mixture contains CD46-binding molecules having the same affinity as 02-237 IgG alone.

Taken together, this experiment shows that it is possible to express a mixture of functional IgG molecules comprising three unique heavy chains in a single cell and that next to the homodimers, heterodimers consisting of two binding specificities are also formed. Furthermore, the frequency of clones expressing three different heavy chains suggests that it will also be possible to obtain clones expressing at least 4, 5, or more, heavy chains, using the same procedure. In the case where it would be difficult to obtain clones expressing higher numbers of heavy chains, a clone expressing at least three heavy chains according to the invention can be used to introduce more heavy chains in a separate round of transfection, for instance by using a different selection marker.

Next, it was demonstrated that a single cell is able to produce a mixture of more than two functional human IgGs. Therefore, clones 241, 280 and 402, which were screened positive for the production of each of the three IgGs, both by IEF and MS, were subjected to limiting dilution, i.e., seeded at 0.3 cells/well in 96-well plates to guarantee clonal outgrowth.

Clonal cell populations, hereafter designated as sub-clones, were refreshed once a week with fresh medium. Sub-clones were grown and transferred from 96-well plates via 24- and 6-well plates, T25, T80 and T175 flasks. At the T80 stage, sub-clones were frozen. Production levels of recombinant human IgG1 antibody were determined in the supernatant using a human IgG1-specific ELISA. For each parental clone, three sub-clones were chosen and cultured in a few T175 flasks to obtain sufficient conditioned medium for purification using Protein A-affinity chromatography as described above.

Purified human IgG1 from the sub-clones was subsequently analyzed as described above for human IgG1 obtained from the parental clone by iso-electric focusing (IEF). The result is shown in FIG. 21. Sub-clones from clone poly 1-241 each have the same pattern, but differ from the parental clone in that they appear to miss certain bands.

Sub-clones from clone poly 1-280 all appear to differ from each other and from the parental clone. Patterns obtained by IEF for sub-clones from parental clone poly 1-402 are identical for all three sub-clones and the parent clone.

From these data, it can be concluded that clone 402 is stably producing a mixture of antibodies. This demonstrates that it is feasible to produce a mixture of antibodies according to the invention from a single cell clone. The clones have undergone about 25 population doublings (cell divisions) from the transfection procedure up to the first analysis (shown in FIG. 18) under selection pressure and, from that point on, have undergone about 30 population doublings during the sub-cloning procedure in the absence of selection pressure before the material analyzed in FIG. 21 was harvested. Therefore, the production of a mixture of antibodies from a clone from a single cell can be stable over at least 30 generations.

Purified IgG1 from the parental 241, 280 and 402 clones, and sub-clones, were also analyzed for binding reactivity towards the CD46 and EpCAM antigens. To this end, cDNA of EpCAM, CD46, and control antigen CD38 were cloned into expression vectors pcDNA (Invitrogen). These vectors were transfected into CHO (dhfr-) cells using Fugene (Roche) according to the protocol supplied by the manufacturer. Cells were cultured in Iscove's medium containing 10% FBS and HT supplement (Gibco). After culturing for two days, cells were harvested by trypsinization and suspended in PBS-1% BSA (PBSB) for use in FACS analysis.

Purified IgG1 of the clones producing the mixtures of antibodies and control IgG1 samples of anti-GBSIII, an anti-CD72 antibody (02-004), as well as antibodies from anti-EpCAM clone UBS54 and anti-CD46 clones K53 and 02-237, were diluted in PBSB to a concentration of 20 µg IgG1/ml. Twenty µl of each was added to 200,000 transfected cells and incubated on ice for one hour. Thereafter, cells were washed once in ice-cold PBSB. Bound IgG was then detected using incubation with goat-anti-human IgG-biotin followed by streptavidin-PE. After a final washing step, cells were suspended in PBSB containing 1 µg/ml propidium iodide. The samples were analyzed on a FACS (FACSvantage, Becton Dickinson). Live cells were gated and Mean Fluorescent Intensities (MFI) were calculated from the FACS plots. The results are represented in FIG. 22. As expected, UBS54 bound selectively to EpCAM-transfected cells and 02-237 and K53 bound selectively to CD46 transfectants, while unrelated antibodies did not bind to these transfectants.

The results demonstrate that binding activities towards both EpCAM and CD46 were present in the purified IgG1 preps of most clones expressing a mixture of antibodies according to the invention, demonstrating that a mixture of functional antibodies was produced by sub-clones that have undergone more than 30 cell divisions and that result from a single cell. In sub-clone 280-015, binding patterns towards CD46 and EpCAM were similar as in the parent clone poly 1-280, in contrast to the other clones.

It should be stated that the quantitative aspect of this assay is not completely clear. Routine screening, for example, by a functional test, can be used to find a clone with the desired expression profile. Quantitative aspects may also be included in such screens. Such screening allows for the identification of desired clones, which express the mixture of antibodies with a given functionality in a quantitatively stable manner.

All references, including publications, patents, and patent applications, cited herein are hereby incorporated by reference to the same extent as if each reference were individually and specifically indicated to be incorporated by reference and were set forth in its entirety herein.

TABLE I

Overview of the clones used for purification of IgG.

| Clone Poly1- | Screening ELISA (µg/ml) | Purification Conc. in feed (µg/ml) | Purified (mg) |
|---|---|---|---|
| 209 | 6.1 | 98 | 1.37 |
| 233 | 10.0 | 53 | 0.75 |
| 234 | 8.0 | 51 | 0.71 |
| 241 | 6.6 | 91 | 1.42 |
| 250 | 12.5 | 117 | 2.10 |
| 280 | 6.3 | 36 | 0.80 |
| 282 | 8.5 | 67 | 1.48 |
| 289 | 8.2 | 33 | 0.64 |
| 304 | 7.2 | 161 | 3.91 |
| 320 | 6.3 | 43 | 0.83 |
| 322 | 15.2 | 168 | 3.27 |
| 340 | 6.0 | 109 | 2.64 |
| 361 | 10.4 | 71 | 1.73 |
| 379 | 9.5 | 78 | 1.75 |
| 402 | 39.9 | 135 | 3.14 |
| 022 | 16.2 | 83 | 1.69 |
| 040 | 7.8 | 67 | 1.43 |
| 048 | 6.5 | 43 | 0.94 |
| 055 | 11 | 55 | 1.04 |

TABLE II

Tryptic peptides of the variable domains of the light chain of K53/UBS54 and 02-237.

| Peptide | First AA[1] | Last AA | Monoisotopic $M_W$ (Da) K53/UBS54 | Monoisotopic $M_W$ (Da) 02-237 |
|---|---|---|---|---|
| L1 | 1 | 24 | 2580.31[2] | 2554.28[2] |
| L2 | 25 | 59 | 4039.02 | 4039.02 |
| L3 | 60 | 66 | 700.35 | 700.35 |
| L4 | 67 | 79 | 1302.61 | 1302.61 |
| L5 | 80 | 82 | 374.23 | 374.23 |
| L6 | 83 | 107 | 2810.29[2] | 2810.29[2] |
| L7 | 108 | 111 | 487.30 | 487.30 |
| L8 | 112 | 112 | 174.11 | 174.11 |

[1] AA, amino acid
[2] One Cysteine residue alkylated

TABLE III

Tryptic peptides of variable domains of heavy chains of K53, 02-237 and UBS54.

| | K53 | | | | 02-237 | | | | UBS54 | | | |
|---|---|---|---|---|---|---|---|---|---|---|---|---|
| | A | B | C | D | A | B | C | D | A | B | C | D |
| | H1 | 1 | 12 | 1267.68 | H1 | 1 | 12 | 1267.68 | H1 | 1 | 12 | 1267.68 |
| | H2 | 13 | 19 | 685.41 | H2 | 13 | 19 | 685.41 | *H2* | *13* | *19* | *729.41* |
| | H3 | 20 | 23 | 492.24 | H3 | 20 | 23 | 492.24 | H3 | 20 | 23 | 492.24 |
| | H4 | 24 | 38 | 1693.81 | H4 | 24 | 38 | 1693.81 | *H4* | *24* | *38* | *1587.77* |
| | H5 | 39 | 63 | 2783.28 | H5 | 39 | 63 | 2783.28 | *H5* | *39* | *63* | *2646.33* |
| | H6 | 64 | 67 | 472.28 | H6 | 64 | 67 | 472.28 | *H6* | *64* | *67* | *506.26* |
| | H7 | 68 | 84 | 1906.87 | H7 | 68 | 84 | 1906.87 | *H7* | *68* | *87* | *2174.04* |
| | H8 | 85 | 87 | 374.23 | H8 | 85 | 87 | 374.23 | — | — | — | — |
| | H9 | 88 | 98 | 1319.55 | H9 | 88 | 98 | 1319.55 | *H8* | *88* | *98* | *1333.56* |
| | *H10* | *99* | *102* | *493.21* | *H10* | *99* | *102* | *475.25* | *H9* | *99* | *119* | *2307.15* |
| | *H11* | *103* | *122* | *2116.05* | *H11* | *103* | *122* | *2057.99* | — | — | — | — |

Key:
A: peptide
B: first amino acid
C: last amino acid
D: monoisotopic $M_w$ (Da)
Remarks:
1) for H1, amino acid residue 1 is a pyroglutamic acid
2) peptides H3 and H9 from K53 and 02-237, and peptides H3 and H8 of UBS54 contain one alkylated cysteine residue
3) Unique peptides that can be used to confirm the presence of the respective IgGs are indicated in bold italics

TABLE IV

MS/MS-data of CDR3 peptide (H11) of K53, obtained by collision induced dissociation of doubly charged m/z 1059.06.

| Ion | m/z |
|---|---|
| $Y''_1$ | 147.12 |
| $Y''_2$ | 248.18 |
| $Y''_3$ | <u>335.21</u>[1] |
| $Y''_4$ | 406.25 |
| $Y''_5$ | 507.30 |
| $Y''_6$ | <u>594.33</u> |
| $Y''_7$ | 693.40 |
| $Y''_8$ | <u>794.46</u> |
| $Y''_9$ | <u>893.54</u> |
| $Y''_{10}$ | 1006.63 |
| $Y''_{11}$ | 1107.67 |
| $Y''_{12}$ | <u>1164.68</u> |
| $Y''_{13}$ | 1292.81 |
| $Y''_{14}$ | <u>1349.77</u> |
| $Y''_{15}$ | <u>1535.85</u> |
| $Y''_{16}$ | 1698.95 |
| $Y''_{17}$ | 1813.95 |
| $Y''_{18}$ | 1960.97 |
| $Y''_{19}$ | n.d.[2] |
| $B_1$ | n.d. |
| $B_2$ | 157.10 |
| $B_3$ | 304.18 |
| $B_4$ | 419.22 |
| $B_5$ | <u>582.31</u> |
| $B_6$ | 768.38 |
| $B_7$ | 825.39 |
| $B_8$ | 953.43 |
| $B_9$ | n.d. |
| $B_{10}$ | n.d. |
| $B_{11}$ | 1224.65 |
| $B_{12}$ | 1323.68 |
| $B_{13}$ | 1424.79 |
| $B_{14}$ | 1523.86 |
| $B_{15}$ | n.d. |
| $B_{16}$ | n.d. |
| $B_{17}$ | 1782.96 |
| $B_{18}$ | n.d. |
| $B_{19}$ | n.d. |

[1] Underlined m/z-values are main peaks in the MS/MS-spectrum.
[2] n.d. is not detected.

TABLE V

MS/MS-data of CDR3 peptide (H11) of 02-237, obtained by collision induced dissociation of doubly charged m/z 1030.02.

| Ion | m/z |
|---|---|
| $Y''_1$ | 147.12 |
| $Y''_2$ | 248.18 |
| $Y''_3$ | <u>335.20</u> |
| $Y''_4$ | 406.24 |
| $Y''_5$ | 493.30 |
| $Y''_6$ | <u>580.32</u> |
| $Y''_7$ | 679.40 |
| $Y''_8$ | <u>780.44</u> |
| $Y''_9$ | <u>879.53</u> |
| $Y''_{10}$ | 992.60 |
| $Y''_{11}$ | 1093.65 |
| $Y''_{12}$ | <u>1150.67</u> |
| $Y''_{13}$ | 1278.80 |
| $Y''_{14}$ | <u>1335.80</u> |
| $Y''_{15}$ | 1521.83 |
| $Y''_{16}$ | 1608.90 |
| $Y''_{17}$ | 1724.00 |
| $Y''_{18}$ | n.d. |
| $Y''_{19}$ | n.d. |
| $B_1$ | n.d. |
| $B_2$ | 189.09 |
| $B_3$ | n.d. |
| $B_4$ | 451.22 |
| $B_5$ | n.d. |
| $B_6$ | n.d. |
| $B_7$ | n.d. |
| $B_8$ | n.d. |
| $B_9$ | n.d. |
| $B_{10}$ | n.d. |
| $B_{11}$ | n.d. |
| $B_{12}$ | n.d. |
| $B_{13}$ | n.d. |
| $B_{14}$ | n.d. |
| $B_{15}$ | n.d. |
| $B_{16}$ | n.d. |
| $B_{17}$ | n.d. |
| $B_{18}$ | n.d. |
| $B_{19}$ | n.d. |

[1] Underlined m/z-values are main peaks in the MS/MS-spectrum.
[2] n.d. is not detected.

TABLE VI

MS/MS-data of CDR3 peptide (H9) of UBS54, obtained by collision induced dissociation of triply charged m/z 770.09.

| Ion | m/z |
|---|---|
| $Y''_1$ | n.d. |
| $Y''_2$ | 248.17 |
| $Y''_3$ | <u>335.20</u> |
| $Y''_4$ | 406.25 |
| $Y''_5$ | <u>507.30</u> |
| $Y''_6$ | <u>594.33</u> |
| $Y''_7$ | <u>693.42</u> |
| $Y''_8$ | <u>794.45</u> |
| $Y''_9$ | <u>893.53</u> |
| $Y''_{10}$ | <u>1006.64</u> |
| $Y''_{11}$ | 1107.67 |
| $Y''_{12}$ | 1164.68 |
| $Y''_{13}$ | n.d. |
| $Y''_{14}$ | n.d. |
| $Y''_{15}$ | n.d. |
| $Y''_{16}$ | n.d. |
| $Y''_{17}$ | n.d. |
| $Y''_{18}$ | n.d. |
| $Y''_{19}$ | n.d. |
| $Y''_{20}$ | n.d. |
| $B_1$ | n.d. |
| $B_2$ | 213.17 |
| $B_3$ | 360.16 |
| $B_4$ | 473.27 |
| $B_5$ | 610.32 |
| $B_6$ | 773.41 |
| $B_7$ | <u>959.48</u> |
| $B_8$ | <u>1016.50</u> |
| $B_9$ | <u>1144.57</u> |
| $B_{10}$ | <u>1201.59</u> |
| $B_{11}$ | <u>1302.68</u> |
| $B_{12}$ | <u>1415.72</u> |
| $B_{13}$ | 1514.78 |
| $B_{14}$ | n.d. |
| $B_{15}$ | n.d. |
| $B_{16}$ | n.d. |
| $B_{17}$ | n.d. |
| $B_{18}$ | n.d. |
| $B_{19}$ | n.d. |
| $B_{20}$ | n.d. |

[1] Underlined m/z-values are main peaks in the MS/MS-spectrum.
[2] n.d. is not detected.

REFERENCES

Appel R. D., Bairoch A. and Hochstrasser D. F. (1994) A new generation of information retrieval tools for biologists: the example of the ExPASy WWW server. *Trends Biochem. Sci.* 19:258-260.

Bendig M. M. (1988) The production of foreign proteins in mammalian cells. *Genet. Eng.* 7:91-127.

Boel E., Verlaan S., Poppelier M. J., Westerdaal N. A., Van Strijp J. A. and Logtenberg T. (2000) Functional human monoclonal antibodies of all isotypes constructed from phage display library-derived single-chain Fv antibody fragments. *J. Immunol. Methods* 239:153-166.

Brink M. F., Bishop M. D. and Pieper F. R. (2000) Developing efficient strategies for the generation of transgenic cattle which produce biopharmaceuticals in milk. *Theriogenology* 53:139-148.

Campbell K. H., McWhir J., Ritchie W. A. and Wilmut I. (1996) Sheep cloned by nuclear transfer from a cultured cell line. *Nature* 380:64-66.

Casellas R., Shih T. A., Kleinewietfelt M., Rakoniac J., Nemazee D., Rajewski K. and Nussenzweig M. C. (2001) Contribution of receptor editing to the antibody repertoire. *Science* 291:1541-1544.

Cockett M. I., Bebbington C. R. and Yarranton G. T. (1990) High level expression of tissue inhibitor of metalloproteinases in Chinese hamster ovary cells using glutamate synthetase gene amplification. *Bio/technology* 8:662-667.

De Kruif J., Terstappen L., Boel E. and Logtenberg T. (1995a) Rapid selection of cell sub-population-specific human monoclonal antibodies from a synthetic phage antibody library. *Proc. Natl. Acad. Sci. U.S.A.* 92:3938

De Kruif J., Boel E. and Logtenberg T. (1995b) Selection and application of human single chain Fv antibody fragments from a semi-synthetic phage antibody display library with designed CDR3 regions. *J. Mol. Biol.* 248:97

Dinnyes A., De Sousa P., King T. and Wilmut I. (2002) Somatic cell nuclear transfer: recent progress and challenges. *Cloning Stem Cells* 4:81-90.

Flavell D. J., Noss A., Pulford K. A., Ling N. and Flavell S. U. (1997) Systemic therapy with 3BIT, a triple combination cocktail of anti-CD19, -CD22, and -CD38-saporin immunotoxins, is curative of human B-cell lymphoma in severe combined immunodeficient mice. *Cancer Res.* 57:4824-4829.

Fishwild D. M., O'Donnell S. L., Bengoechea T., Hudson D. V., Harding F., Bernhard S. L., Jones D., Kay R. M., Higgins K. M., Schramm S. R. and Lonberg N. (1996) High-avidity human IgG kappa monoclonal antibodies from a novel strain of minilocus transgenic mice. *Nat. Biotechnol.* 14:845-51.

Garnick R L. (1992) Peptide mapping for detecting variants in protein products. *Develop. Biol. Standard* 76:117-130.

GelpiE. (1995) Biomedical and biochemical applications of liquid chromatography-mass spectrometry. *J. Chromatography A* 703:59-80.

Ghetie M.-A., Podar E. M., Ilgen A., Gordon B. E., Uhr J. W. and Vitetta E S. (1997) Homodimerization of tumor-reactive monoclonal antibodies markedly increases their ability to induce growth arrest or apoptosis of tumor cells. *Proc. Natl. Acad. Sci. U.S.A.* 94:7509-7514.

Giddings G., Allison G., Brooks D. and Carter A. (2000) Transgenic plants as factories for biopharmaceuticals. *Nat. Biotechnol.* 18:1151-1155.

Gorman C. and Bullock C. (2000) Site-specific gene targeting for gene expression in eukaryotes. *Curr. Opin. Biotechnol.* 11:455-460.

Hiatt A., Cafferkey R. and Bowdish K. (1989) Production of antibodies in transgenic plants. *Nature* 342:76-78.

Huls G. A., Heijnen I. A., Cuomo M. E., Koningsberger J. C., Wiegman L., Boel E., van der Vuurst de Vries A. R., Loyson S. A., Helfrich W., van Berge Henegouwen G. P., van Meijer M., de Kruif J. and Logtenberg T. (1999) A recombinant, fully human monoclonal antibody with antitumor activity constructed from phage-displayed antibody fragments. *Nat. Biotechnol.* 17:276-281.

Jespers L. S., Roberts A., Mahler S. M., Winter G. and Hoogenboom H. R. (1994) Guiding the selection of human antibodies from phage display repertoires to a single epitope of an antigen. *Biotechnology* (N Y) 12:899-903.

Jones D., Kroos N., Anema R., Van Montfort B., Vooys A., Van Der Kraats S., Van Der Helm E., Smits S., Schouten J., Brouwer K., Lagerwerf F., Van Berkel P., Opstelten D-J., Logtenberg T. and Bout A. (2003) High-level expression of recombinant IgG in the human cell line PER.C6®. *Biotechnol. Prog.* 19, 163-168.

Kim S. J., Kim N. S., Ryu C. J., Hong H. J. and Lee G. M. (1998) Characterization of chimeric antibody producing CHO cells in the course of dihydrofolate reductase-mediated gene amplification and their stability in the absence of selective pressure. *Biotechnol. Bioeng.* 58:73-84.

Kohler G. and Millstein C. (1975) Continuous cultures of fused cells secreting antibody of predefined specificity. *Nature* 256:495-497.

Koopman G., Reutelingsperger C. P., Kuijten G. A., Keehnen R. M., Pals S. T. and van Oers M. H. (1994) Annexin V for flow cytometric detection of phosphatidylserine expression on B cells undergoing apoptosis. *Blood* 84:1415-1420.

Larrick J. W. and Thomas D. W. (2001) Producing proteins in transgenic plants and animals. *Curr. Opin. Biotechnol.* 12:411-418.

Massengale W. T., McBurney E. and Gurtler J. (2002) CD20-negative relapse of cutaneous B-cell lymphoma after anti-CD20 monoclonal antibody therapy. *J. Am. Acad. Dermatol.* 46:441-443.

Mendez M. J., Green L. L., Corvalan J. R., Jia X. C., Maynard-Currie C. E., Yang X. D., Gallo M. L., Louie D. M., Lee D. V., Erickson K. L., Luna J., Roy C. M., Abderrahim H., Kirschenbaum F., Noguchi M., Smith D. H., Fukushima A., Hales J. F., Klapholz S., Finer M. H., Davis C. G., Zsebo K. M. and Jakobovits A. (1997) Functional transplant of megabase human immunoglobulin loci recapitulates human antibody response in mice. *Nat. Genet.* 15:146-56.

Merchant A. M., Zhu Z., Yuan J. Q., Goddard A., Adams C. W., Presta L. G. and Carter P. (1998) An efficient route to human bispecific IgG. *Nat. Biotech.* 16:677-681.

Nemazee D. (2000) Receptor editing in B cells. *Adv. Immunol.* 74:89-126.

Nissim A., Hoogenboom H. R., Tomlinson I. M., Flynn G., Midgley C., Lane D. and Winter G. (1994) Antibody fragments from a "single pot" phage display library as immunological reagents. *EMBO. J.* 13:692-698.

Nowakowski A., Wang C., Powers D. B., Amersdorfer P., Smith T. J., Montgomery V. A., Sheridan R., Blake R., Smith L. A. and Marks J. D. (2002) Potent neutralization of botulinum neurotoxin by recombinant oligoclonal antibody. *Proc. Natl. Acad. Sci. U.S.A.* 99:11346-11350.

Patel A. K. and Boyd P. N. (1995) An improved assay for antibody-dependent cellular cytotoxicity based on time resolved fluorometry. *Journal of Immunological Methods* 184:29-38.

Peeters K., De Wilde C., De Jaeger G., Angenon G. and Depicker A. (2001) Production of antibodies and antibody fragments in plants. *Vaccine* 19:2756-2761.

Pollock D. P., Kutzko J. P., Birck-Wilson E., Williams J. L., Echelard Y. and Meade H. M. (1999) Transgenic milk as a method for the production of recombinant antibodies. *J. Immunol. Methods* 231:147-157.

Radic M. C., Mascelli M. A., Shan H. and Weigert M. (1991) Ig H and L chain contributions to auto-immune specificities. *J. Immunol.* 146:176-182.

Schnieke A. E., Kind A. J., Ritchie W. A., Mycock K., Scott A. R., Ritchie M., Wilmut I., Colman A. and Campbell K. H. (1997) Human factor IX transgenic sheep produced by transfer of nuclei from transfected fetal fibroblasts. *Science* 278:2130-2133.

Segal D. M., Weiner G. J. and Weiner L. M. (2001) Introduction: bispecific antibodies. *J. Immunol. Methods* 248:1-6.

Shields R. L., Namenuk A. K., Hong K., Gloria Meng Y., Rae J., Biggs J., Xie D., Lai J., Stadlen A., Li B., Fox J. A. and Presta L. G. (2001) High resolution mapping of the binding site on human IgG1 for FcgRI, FcgRII, FcgRIII and FcRn and design of IgG1 variants with improved binding to the FcgR. *J. Biol. Chem.* 276:6591-6604.

Spiridon C. I., Ghetie M. A., Uhr J., Marches R., Li J. L., Shen G. L. and Vitetta E. S. (2002) Targeting multiple her-2 epitopes with monoclonal antibodies results in improved antigrowth activity of a human breast cancer cell line in vitro and in vivo. *Clin. Cancer Res.* 8:1720-1730.

Van der Vuurst de Vries A. and Logtenberg T. (1999) Dissecting the human peripheral B-cell compartment with phage display-derived antibodies. *Immunology* 98:55-62.

Vaughan T. J., Williams A. J., Pritchard K., Osbourn J. K., Pope A. R., Earnshaw J. C., McCafferty J., Hodits R. A., Wilton J. and Johnson K. S. (1996) Human antibodies with sub-nanomolar affinities isolated from a large non-immunized phage display library. *Nat. Biotech.* 14:309-314.

Wilmut I. and Clark A. J. (1991) Basic techniques for transgenesis. *J. Reprod. Fertil. Suppl.* 43:265-275.

Wilmut I., Schnieke A. E., McWhir J., Kind A. J. and Campbell K. H. (1997) Viable offspring derived from fetal and adult mammalian cells. *Nature* 385:810-813.

Wilson T. J. and Kola I. (2001) The LoxP/CRE system and genome modification. *Methods Mol. Biol.* 158:83-94.

Yelverton E., Norton S., Obijeski J. F. and Goeddel D. V. (1983) Rabies virus glycoprotein analogs: biosynthesis in *Escherichia coli*. *Science* 219:614-620.

Yoo E. M., Coloma M. J., Trinh K. R., Nguyen T. Q., Vuong L. U., Morrison S. L. and Chintalacharuvu K. R. (1999) Structural requirements for polymeric immunoglobulin assembly and association with J chain. *J. Biol. Chem.* 274: 33771-33777.

What is claimed is:

1. A method of producing a host cell, said method comprising:
   introducing into a host cell at least one nucleic acid sequence encoding an immunoglobulin light chain and nucleic acid sequences encoding at least three different immunoglobulin heavy chains,
   wherein said at least three different immunoglobulin heavy chains are capable of pairing with said immunoglobulin light chain to form functional antigen binding domains of three or more non-identical antibodies.

2. The method according to claim 1, wherein said three or more non-identical antibodies have differing specificities for the same target antigen.

3. The method according to claim 1, wherein said three or more non-identical antibodies have differing affinities for the same target epitope.

4. The method according to claim 1, wherein said at least one nucleic acid sequence is present on a low copy number vector and said host cell produces 1 to 20 picograms per cell per day of said three or more non-identical antibodies.

5. The method according to claim 1, wherein said host cell comprises a human embryonic retina cell, and wherein said host cell has been immortalized or transformed by adenoviral E1 nucleic acid sequences.

6. The method according to claim 1, wherein said three or more non-identical antibodies are of different isotypes.

7. The method according to claim 6, wherein said different isotypes comprise at least an IgG and an IgA.

8. The method according to claim 6, wherein said different isotypes comprise at least an IgG1 and an IgG3 antibody.

9. The method according to claim 1, wherein said three or more non-identical antibodies are independently selected from the group consisting of IgG1, IgG2, IgG3, IgG4, IgA1, IgA2, IgD, IgE and IgM.

10. The method according to claim 1, wherein said at least three different immunoglobulin heavy chains are of IgM isotype.

11. The method according to claim 1, wherein said at least three different immunoglobulin heavy chains are of an IgA isotype, and wherein at least two of said three or more non-identical antibodies form a dimeric IgA antibody, said dimeric IgA antibody having non-identical binding sites.

12. The method according to claim 1, wherein said three or more non-identical antibodies bind to different epitopes of at least one target antigen.

13. The method according to claim 1, wherein at least one of said at least one nucleic acid sequence is stably expressed in said host cell.

14. The method according to claim 1, wherein said three or more non-identical antibodies are produced by said host cell in vitro.

15. The method according to claim 1, wherein said at least three different immunoglobulin heavy chains differ in at least one constant region, said difference in at least one constant region reducing non-functional antibody chain pairing.

16. The method according to claim 1, wherein said three or more non-identical antibodies comprise at least one bispecific antibody.

17. The method according to claim 1, wherein said three or more non-identical antibodies bind to different antigens.

18. The method according to claim 1, wherein said three or more non-identical antibodies bind synergistically to a target antigen.

19. The method according to claim 1, wherein a first antibody of the three or more non-identical antibodies binds CD22, a second antibody of the three or more non-identical antibodies binds CD72, and a third antibody of the three or more non-identical antibodies binds HLA-DR.

20. The method according to claim 1, wherein a first antibody of the three or more non-identical antibodies binds an EP-CAM homotypic adhesion molecule, and wherein a second antibody and a third antibody of the three or more non-identical antibodies each bind CD46.

21. The method according to claim 1, wherein at least three of the three or more non-identical antibodies bind to non-overlapping epitopes on Her-2.

22. The method according to claim 1, wherein the three or more non-identical antibodies bind to targets selected from the group consisting of a Her-2/Neu receptor, a VEGFR1 receptor, a VEGFR2 receptor, a B-cell marker, a T-cell marker, cytokines, interleukins, and cytokine receptors.

23. A method of producing a host cell, said method comprising:
   providing a host cell comprising a nucleic acid sequence encoding an immunoglobulin light chain;
   introducing nucleic acid sequences encoding at least three different immunoglobulin heavy chains into said host cell,
   wherein said at least three different immunoglobulin heavy chains are capable of pairing with said immunoglobulin light chain to form functional antigen binding domains of the three or more non-identical antibodies.

* * * * *

UNITED STATES PATENT AND TRADEMARK OFFICE
CERTIFICATE OF CORRECTION

PATENT NO. : 7,927,834 B2  
APPLICATION NO. : 12/221021  
DATED : April 19, 2011  
INVENTOR(S) : Patricius Hendrikus Van Berkel et al.

Page 1 of 1

It is certified that error appears in the above-identified patent and that said Letters Patent is hereby corrected as shown below:

On the title page:
In ITEM (75) INVENTORS
 change "Patrick H.C. Van Berkel" to --Patricius Hendrikus Van Berkel--
 change "Ultrecht" to --Berkel en Rodenrijs--
 change "Driebergen" to --Werkhoven--

Signed and Sealed this
Twenty-sixth Day of July, 2011

David J. Kappos
*Director of the United States Patent and Trademark Office*

UNITED STATES PATENT AND TRADEMARK OFFICE
CERTIFICATE OF CORRECTION

PATENT NO. : 7,927,834 B2  
APPLICATION NO. : 12/221021  
DATED : April 19, 2011  
INVENTOR(S) : Patrick Hendrikus Van Berkel et al.

Page 1 of 1

It is certified that error appears in the above-identified patent and that said Letters Patent is hereby corrected as shown below:

On the title page:
In ITEM (75) INVENTORS

Change "Werkhoven" to --Driebergen--.

Signed and Sealed this
Sixth Day of September, 2011

David J. Kappos
*Director of the United States Patent and Trademark Office*

UNITED STATES PATENT AND TRADEMARK OFFICE
CERTIFICATE OF CORRECTION

PATENT NO. : 7,927,834 B2  
APPLICATION NO. : 12/221021  
DATED : April 19, 2011  
INVENTOR(S) : Patricius Hendrikus Cornelis Van Berkel et al.

Page 1 of 1

It is certified that error appears in the above-identified patent and that said Letters Patent is hereby corrected as shown below:

On the title page:
In ITEM (75) INVENTORS should read:

-- Patricius Hendrikus Cornelis Van Berkel, Berkel en Rodenrijs (NL); Ronald Hendrik Peter Brus, Voorschoten (NL); Ton Logtenberg, Driebergen (NL); Abraham Bout, Moerkapelle (NL) --

This certificate supersedes the Certificates of Correction issued July 26, 2011 and September 6, 2011.

Signed and Sealed this
First Day of October, 2013

Teresa Stanek Rea
*Deputy Director of the United States Patent and Trademark Office*